US008460647B2

(12) United States Patent
Gaffen et al.

(10) Patent No.: US 8,460,647 B2
(45) Date of Patent: *Jun. 11, 2013

(54) PRE-LIGAND ASSEMBLY DOMAIN OF THE IL-17 RECEPTOR

(75) Inventors: Sarah L. Gaffen, Amherst, NY (US); Fang Shen, Amherst, NY (US); Walter Hanel, Stony Brook, NY (US); Jill Kramer, Glen Oaks, MA (US); James P. Malone, Buffalo, NY (US); Michael Wittekind, Bainbridge Island, WA (US); Raymond Paxton, Bellevue, WA (US)

(73) Assignees: Amgen Inc., Thousand Oaks, CA (US); Research Foundation of the State University of New York, Amherst, NY (US)

( * ) Notice: Subject to any disclaimer, the term of this patent is extended or adjusted under 35 U.S.C. 154(b) by 202 days.

This patent is subject to a terminal disclaimer.

(21) Appl. No.: 12/595,585

(22) PCT Filed: Apr. 20, 2008

(86) PCT No.: PCT/US2008/060953
§ 371 (c)(1),
(2), (4) Date: Mar. 25, 2010

(87) PCT Pub. No.: WO2008/131315
PCT Pub. Date: Oct. 30, 2008

(65) Prior Publication Data
US 2012/0009190 A1 Jan. 12, 2012

Related U.S. Application Data

(60) Provisional application No. 60/925,367, filed on Apr. 20, 2007.

(51) Int. Cl.
C07K 14/7155 (2006.01)
C07K 2319/00 (2006.01)
C07K 2319/33 (2006.01)

(52) U.S. Cl.
USPC .......... 424/85.2; 530/300; 530/350; 514/18.7

(58) Field of Classification Search
None
See application file for complete search history.

(56) References Cited

U.S. PATENT DOCUMENTS
6,096,305 A 8/2000 Yao et al.
7,115,398 B2 * 10/2006 Chen et al. ................. 435/69.52

FOREIGN PATENT DOCUMENTS
WO WO-2004/002519 1/2004
WO WO-2005/063290 7/2005
WO WO2005123778 * 12/2005
WO WO-2006/059110 6/2006
WO WO-2007/038703 4/2007

OTHER PUBLICATIONS

Lazar et al (Mol. Cell. Biol., vol. 8, pp. 1247-1252, 1988.*
Wells, 1990, Biochemistry 29:8509-8517.*
Bork, 2000, Genome Research 10:398-400.*
Skolnick et al., 2000, Trends in Biotech. 18(1):34-39.*
Doerks et al., 1998, Trends in Genetics 14:248-250.*
Tokuriki and Tawflik, (Current Opinion in Structural Biology 2009, 19: 596-604.*
Cannetti et al., IL-18 enhances collagen-induced arthritis by recruiting neutrophils via TNF-alpha and leukotriene B4. J. Immunl. 171(2): 1009-15 (2003).
Chabaud et al., The combination of tumor necrosis factor alpha blockade with interleukin-1 and interleukin-17 blockade is more effective for controlling synovial inflammation and bone resorption in an ex vivo model. Arthritis Rheum. 44(6): 1293 (2001).
Charles et al., Regulation of cytokines, cytokine inhibitors, and acute-phase proteins following anti-TNF-alpha therapy in rheumatoid arthritis. J. Immunol. 163(3): 1521-8 (1999).
Cunnane et al., Serum amyloid A in the assessment of early inflammatory arthritis. J. Rheumatol. 27: 58-63 (2000).
Deng et al., Amelioration of inflammatory arthritis by targeting the pre-ligand assembly domain of tumor necrosis factor receptors. Nat. Med. 11(10): 1066-72 (2005).
Gaffen, Signaling domains of the interleukin 2 receptor. Cytokine, 14: 63-77 (2001).
Kikly et al., the IL-23/Th17 axis: Therapeutic targets for autoimmune inflammation. Curr. Opin. Immunol. 18(6): 670-5 (2006).
Konishi et al., IL-18 contributes to the spontaneous development of atopic dermatitis-like inflammatory skin lesion independently of IgE/stat6 under specific pathogen-free conditions. Proc. Natl. Acad. Sci. USA, 99(17): 11340-5 (2002).
Kramer et al., 78 dissecting the IL-17 receptor: Identification of a pre-ligand assembly domain (PLAD) and ligand binding site in IL-17RA. Cytokine, 39(1): 22 (2007).
Kramer et al., Cutting edge: Evidence for ligand-independent multimerization of the IL-17 receptor. J. Immunol. 176(2): 711-5 (2006).
Kramer et al., Cutting edge: Identification of a pre-ligand assembly domain (PLAD) and ligand binding site in the IL-17 receptor. J. Immunol. 179(10): 6379-83 (2007).

(Continued)

Primary Examiner — Bridget E Bunner
Assistant Examiner — Fozia Hamud
(74) Attorney, Agent, or Firm — Marshall, Gerstein & Borun LLP

(57) ABSTRACT

The invention provides isolated Pre-Ligand Assembly Domain (PLAD) polypeptides comprising an amino acid sequence of a domain (e.g., a Fibronectin III-like domain) of an IL-17 Receptor (IL-17R) family member, wherein the PLAD polypeptide inhibits multimerization of a receptor complex comprising an IL-17R family member. Also provided are isolated PLAD-binding polypeptides, e.g., antibodies and avimers, which specifically bind to a PLAD polypeptide described herein. Related chimeric proteins, conjugates, nucleic acids, vectors, and host cells are provided herein. Further provided are methods of treating an inflammatory or autoimmune disease, methods of inhibiting IL-17-mediated signal transduction, methods of inhibiting IL-17 ligand binding, methods of inhibiting multimerization of IL-17R complexes, and methods of inhibiting the production of at least one cytokine, chemokine, matrix metalloproteinase, or other molecule associated with IL-17 signal transduction are provided.

8 Claims, 17 Drawing Sheets

OTHER PUBLICATIONS

Livnah et al., Crystallographic evidence for preformed dimers of erythropoietin receptor before ligand activation. *Science*, 283(5404): 987-90 (1999).

Miossec, Interleukin-17 in rheumatoid arthritis: if T cells were to contribute to inflammation and destruction through synergy. P. *Arthritis Rheum*. 48(3): 594-601 (2003).

Neiditch et al., Ligand-induced asymmetry in histidine sensor kinase complex regulates quorum sensing. *Cell*, 126(6): 1095-108 (2006).

Niederau et al., Inflammatory mediators and acute phase proteins in patients with Crohn's disease and ulcerative colitis. *Hepato-Gastroenterol*. 44: 90-107 (1997).

Remy et al., Erythropoietin receptor activation by a ligand-induced conformation change. *Science*, 283(5404): 990-3 (1999).

Romani et al., IL-17 and therapeutic kynurenines in pathogenic inflammation to fungi. *J. Immunol*. 180(8): 5157-62 (2008).

Rutitzsky, IL-23 is required for the development of severe egg-induced immunopathology in schistosomiasis and for lesional expression of IL-17. *J. Immunol*. 180(4): 2486-95 (2008).

Shen et al., Structure-function relationships in the IL-17 receptor: Implications for signal transduction and therapy. *Cytokine*, 41(2): 92-104 (2008).

Toy et al., Cutting edge: interleukin 17 signals through a heteromeric receptor complex. *J. Immunol*. 177(1): 36-9 (2006).

Yoshimoto et al., IL-12 up-regulates IL-18 receptor expression on T cells, Th1 cells, and B cells: synergism with IL-18 for IFN-gamma production. *J. Immunol*. 161(7): 3400-7 (1998).

* cited by examiner

FIG. 1A
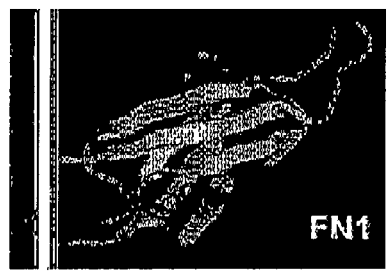
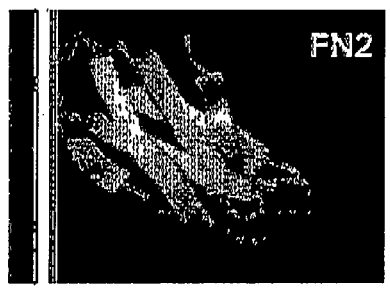
IL-17RA-FN1:
59-TPSSPK...NHKSKIIFVP-183
IL-17RA linker:
184-DCECSKMKMTTSCVSSGSLWD-204
IL-17RA-FN2:
205-PNITVETLD...CCHHHVQV-282

FIG. 1B
Yeast 2-hybrid constructs
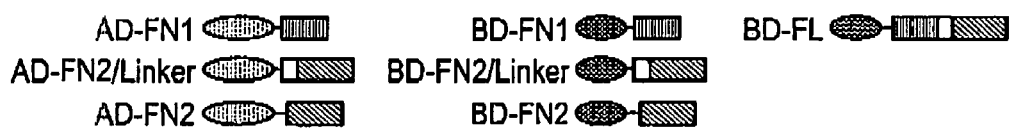
FRET constructs
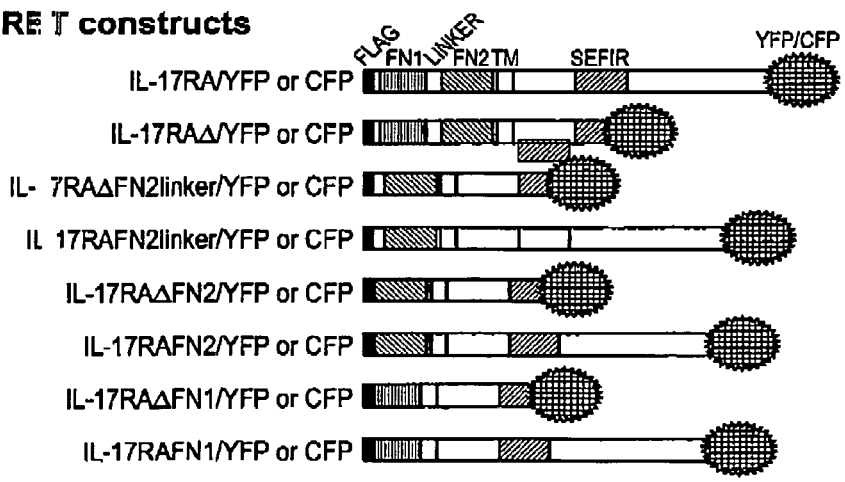

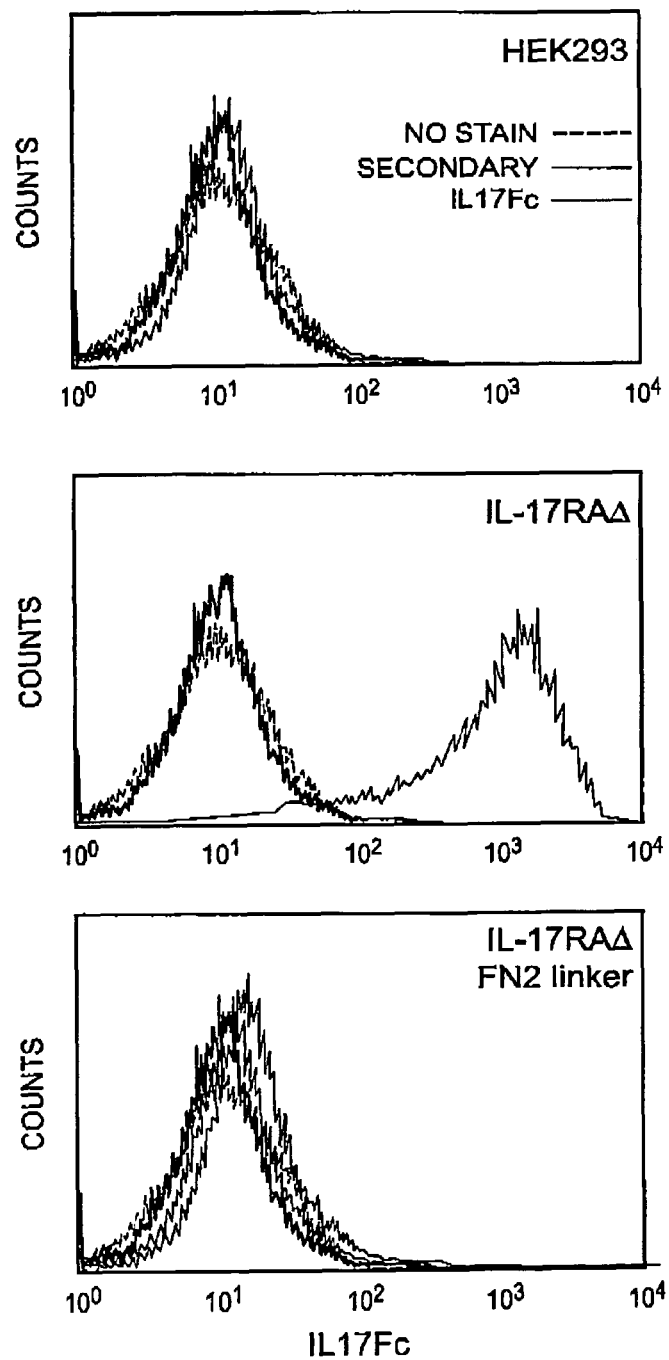

FIG. 5A

Red= leader  Purple= SEFIR
Pink = FN1  Underline = TILL
Green= linker
Blue = FN2
Red = TM

MOUSE IL-17RA
NM_008359

```
1/1                                                                                  31/11                                                                                    61/21
atg gcg att cgg cgc tgc cca cgg gtc ccc ggg ccc gcg ctg gga tgg ctg ctt ctg ctg aac gtt ctg gcc ccg ggc cgc
 M   A   I   R   R   C   P   R   V   P   G   P   A   L   G   W   L   L   L   L   N   V   L   A   P   G   R 91/31                                                                                121/41                                                                                  151/51
gcc tcc ccg cgc ctc ctc gac ttc ccg gct ccg gtc tgc gcg cag gag ggg ctg agc tgc aga gtc aag aat agt act tgt gat gac
 A   S   P   R   L   L   D   F   P   A   P   V   C   A   Q   E   G   L   S   C   R   V   K   N   S   T   C   D   D 181/61                                                                               211/71                                                                                  241/81
agc tgg atc cac ccc aaa aac ctg acc ccg tct tcc cca aaa aac atc atc tat atc aat ctt acc cag cac tct acc gga gaa tta
 S   W   I   H   P   K   N   L   T   P   S   S   P   K   N   I   I   Y   I   N   L   T   Q   H   S   T   G   E   L 271/91                                                                               301/101                                                                                 331/111
gtc cct gtg cat gtt gag tgg gag gtg acg ctg cag aca gat gcc agc atc ctg tac ctc gag ggt gca gag ctg tcc gtc aac cgc
 V   P   V   H   V   E   W   E   V   T   L   Q   T   D   A   S   I   L   Y   L   E   G   A   E   L   S   V   N   R 361/121                                                                              391/131                                                                                 421/141
acc aat gag cgg ctg tgt ctg tgt gtc aag ttc cag tac ctc tgc atg ctg cag cat cac cgt aag cgg tgg cgg ttt cgg ttt tcc
 T   N   E   R   L   C   L   C   V   K   F   Q   Y   L   C   M   L   Q   H   H   R   K   R   W   R   F   R   F   S 451/151                                                                              481/161                                                                                 511/171
gta gat cct ggc cag gag tgt gag cct tat gaa act atc aag atg act aac ccc ccg aag cca ccg atc gat ccc aac cac cca aag
 V   D   P   G   Q   E   C   E   P   Y   E   T   I   K   M   T   N   P   P   K   P   P   I   D   P   N   H   P   K 541/181                                                                              571/191                                                                                 601/201
ttt gtg cct gac tgt gag gac agc agc gac atg aag aag atg act gtc gag agc ctt tgg gac cca aac cac tgg ctt ttg tac
 F   V   P   D   C   E   D   S   S   D   M   K   K   M   T   V   E   S   L   W   D   P   N   H   W   L   L   Y 631/211                                                                              661/221                                                                                 691/231
acc ttg gac aca cag cat ctg cga gtt gac ttc acc ctg tgg aat gaa tcc acc ccc tac tcc gtc ctg ctc ttt agc acc ctg cag aac
 T   L   D   T   Q   H   L   R   V   D   F   T   L   W   N   E   S   T   P   Y   Q   V   L   L   E   S   F   S   T   Q 721/241                                                                              751/251                                                                                 781/261
acc ttg gac aca cag cat ctg cga gtt gac ttc acc ctg tgg aat gaa tcc acc ccc tac cag gtg ctg ctt gaa agt ttc tcc gac tca
 T   L   D   T   Q   H   L   R   V   D   F   T   L   W   N   E   S   T   P   Y   Q   V   L   L   E   S   F   S   D   S
```

```
       gag aac cac agc ttt gat gtc gtt aaa caa ata ttt gcg ccc agg caa gaa ttc cat cag gct aat gtc aca act cta
        E   N   H   S   F   D   V   V   K   Q   I   F   A   P   R   Q   E   F   H   Q   A   N   V   T   T   L
   811/271                                     841/281                              871/291
       agc aag ttt cac tgg tgc cat cac gtg cag gtc cac ttc agc agc tgc cta aat gac tgt gct gta act
        S   K   F   H   W   C   H   H   V   Q   V   H   F   S   S   C   L   N   D   C   A   V   T
                                              931/311
       gtg ccc tgc cca gta atc tca aat aca acc gtt ccc aag cca gtt cca gac tac ggc tat gtg ctc atc aca ctc att
        V   P   C   P   V   I   S   N   T   T   V   P   K   P   V   P   D   Y   G   Y   V   L   I   T   L   I
   901/301                                                                         961/321
                                              1021/341
       gcc att ctg ctg gga tct gtc atc gtg atc atc tgt atg acc tgg agg ctt cct ggc gcc gat caa gag aaa cat ggt gat gac
        A   I   L   L   G   S   V   I   V   I   I   C   M   T   W   R   L   P   G   A   D   Q   E   K   H   G   D   D
   991/331                                     1081/361                             1141/381
       tcc aaa atc aat ggc atc ttg ccc gta gca gat ctg act ccc cca cca agg ccc cag aag gtc tgg gtt aga cac gcc cac
        S   K   I   N   G   I   L   P   V   A   D   L   T   P   P   P   R   P   Q   K   V   W   V   R   H   A   D   H
   1171/391                                    1201/401                             1231/411
       ccc ctc tat gtg gag gta ctg gtc atg gtc gga gtg gta gac gca gtc ctt gtc atc ctg gac ctg gaa gag cag
        P   L   Y   V   E   V   L   V   M   V   G   V   V   D   A   V   L   V   I   L   D   L   E   E   Q
                                              1291/431                              1321/441
       gtt atc tct gag gtg ggg gtc atg acc aaa tgg aaa gct tgg tgg gct gag cct aag cca ttc tgt tgt tcc
        V   I   S   E   V   G   V   M   T   K   W   K   A   W   W   A   E   P   K   P   F   C   C   S
   1351/451                                    1381/461                             1411/471
       cga ggc acc caa gca gcc atg aac atg atc ctg gtg agc cga cag gct gag cct tgg cac gtt tac ttc agt ggc gac
        R   G   T   Q   A   A   M   N   M   I   L   V   S   R   Q   A   E   P   W   H   V   Y   F   S   G   D
   1441/481                                    1471/491                             1501/501
       ctt ttc act gca gcc atg aac atc ctg ccc gac ttc aag agg cca ttc tgg ccc acc gac tac gtt gtt tgc tac tgg cac
        L   F   T   A   A   M   N   I   L   P   D   F   K   R   P   F   W   P   T   D   Y   V   V   C   Y   W   H
   1531/511                                    1561/521                             1591/531
       tgt agt gag agg gat gtc ccc ccc ctc ttc aac atc atc acc tcc agg tac cca ctc atg gac aga ttt gag gac gtt tac ttc cgg atc cag
        C   S   E   R   D   V   P   P   L   F   N   I   I   T   S   R   Y   P   L   M   D   R   F   E   D   V   Y   F   R   I   Q
                                              1651/551                              1681/561
       gac ctg cag atg ttt gaa ccc ggc atg cat cac gtc aga gag ctc aca ggg gac aat tac ctg cag agc cgg cag ctc
        D   L   Q   M   F   E   P   G   M   H   H   V   R   E   L   T   G   D   N   Y   L   Q   S   R   Q   L
   1711/571                                    1741/581                             1771/591
```

FIG. 5C

```
aag gag gct gtg ctt agg ttc cag gag tgg caa acc cag tgc ccc gac tgg ttc gag cgt gag aac ctc tgc tta gct gat ggc caa gat
 K   E   A   V   L   R   F   Q   E   W   Q   T   Q   C   P   D   W   F   E   R   E   N   L   C   L   A   D   G   Q   D
1801/601                                                                             1861/621 ctt ccc tcc ctg gat gaa gaa gtg ttt gac cca cca ctg cca ggg gga gga att gtc aaa cag ccc ctg gtg ctg gtg cgg gaa ctc
 L   P   S   L   D   E   E   V   F   E   D   P   L   P   G   G   G   I   V   K   Q   P   L   V   L   V   R   E   L
1891/631                                                                             1951/651 cca tct gac ggc tgc ctt gta gat gtc tgt gta agt gag gaa gaa agt aga atg gca aag ctg gac cct cag cta tgg cca cag aga
 P   S   D   G   C   L   V   D   V   C   V   S   E   E   E   S   R   M   A   K   L   D   P   Q   L   W   P   Q   R
1981/661                                                                             2041/681 gag cta gtg gct cac acc caa agc atg ccc gtg ctg cca gag cag cat gtg gtg cag agg aac agc atc ctt tgc cca gac
 E   L   V   A   H   T   Q   S   M   P   V   L   P   E   Q   H   V   V   Q   R   N   S   I   L   C   P   D
2071/691                                                                             2131/711 ggc agt gga gca gct gcc cag ctg ccg ctg ctg gtc ccc gct gcc gct ctg ctg ggg gtc cag agg cag agg cct ctc cat ctc cca gac
 G   S   G   A   A   A   Q   L   P   L   L   V   P   A   A   A   L   L   G   V   Q   R   Q   R   P   L   H   L   P   D
2161/721                                                                             2221/741 ccc gtg gac tca gat ttg cca atg aca gag gac gac agc ctg ccg cct ccg atg tca atg tac atc cca gac cac ctc caa ggc gat gca gaa gag
 P   V   D   S   D   L   P   M   T   E   D   D   S   L   P   P   P   M   S   M   Y   I   P   D   H   L   Q   G   D   A   E   E
2251/751                                                                             2311/771 cta atg ctc tcg gtg ctg cag agc cag agt gga gag cag ccc cta ggg agc ctg tgg ccg agg cca gag gtg ctc cag agg cca aca ccc
 L   M   L   S   V   L   Q   S   Q   S   G   E   Q   P   L   G   S   L   W   P   R   P   E   V   L   Q   R   P   T   P
2341/781                                                                             2401/801 tct gag gag gag cag cgg gtg cag gat gac agc ctc cag ggg gag gtg gta agg gca ccc gag gca gag gag
 S   E   E   E   Q   R   V   Q   D   D   S   L   Q   G   E   V   V   R   A   P   E   A   E   E
2431/811                                                                             2491/831 gaa gag cta gag gtg gag gag tac atc ccc tac tac atc tcc gag gaa cta cag tgg gag aag cgg gag aag cta cca gag gag
 E   E   L   E   V   E   E   Y   I   P   Y   Y   I   S   E   E   L   Q   W   E   K   R   E   K   L   P   E   E
2521/841                                                                             2581/861 gag ctc gag aag aac cct tgg aac agc cag gag gag cca cca acc cga aga ccc tag gcc tcc tga gcc tgc
 E   L   E   K   N   P   W   N   S   Q   E   E   P   P   T   R   R   P   *
```

FIG. 6A

Red= leader          Red = TM
Pink = FN1           Purple = SEFIR
Green = linker       underline = TILL
Blue = FN2

HUMAN IL-17RA
NM_014339

```
1/1                                                                    61/21
atg ggg gcc gca cgc agc ccg ccg tcc gct gtc ccg ggg ccc ctg ctg ctg ctg ctg ggc
 M   G   A   A   R   S   P   P   S   A   V   P   G   P   L   L   L   L   L   G 91/31                                                                  151/51
gcc tcc ctg cga ctc cac ctg gac cac cgg gcg ctg gtc tgc tcc cag ccg ggg ctg gcc
 A   S   L   R   L   H   L   D   H   R   A   L   V   C   S   Q   P   G   L   A 181/61                                                                 241/81
agc tgg att cac cct cga aac ctg acc cca aag gac cta cag cag atc cag cat ttt gcc
 S   W   I   H   P   R   N   L   T   P   K   D   L   Q   Q   I   Q   H   F   A 271/91                                                                 331/111
ttc ccc gtg gct cac gaa atc cat gag tgg aca cag cta ggt gtc ttt tac ctc gag gag
 F   P   V   A   H   E   I   H   E   W   T   Q   L   G   V   F   Y   L   E   E 361/121                                                                421/141
acc aat gaa cgt ctg ttt tgc ctg ctc cac tac aga agg cat cac ccc aag ctg cgg tgg
 T   N   E   R   L   F   C   L   L   H   Y   R   R   H   H   P   K   L   R   W 451/151                                                                511/171
gtt gac cct gac cag cag gaa tat gag gtg acc gcc atc cct gat ggg gac cca aac cac
 V   D   P   D   Q   Q   E   Y   E   V   T   A   I   P   D   G   D   P   N   H 541/181                                                                601/201
ctt gtg cct cct gac tgt gag cag cat gag gcc aag gta acc atg agc tgg ctg tgg gac
 L   V   P   P   D   C   E   Q   H   E   A   K   V   T   M   S   W   L   W   D 631/211                                                                691/231
acc ctg gag gcc cac cac cag ctg cgt gtg cgt ctc acc ttc agc ctg tgg gac agc ctg
 T   L   E   A   H   H   Q   L   R   V   R   L   T   F   S   L   W   D   S   L 721/241                                751/251                        781/261
acc cac cag ctg gag cca cgg cag cag ctg gtg gtg ctg ggc ctg cag ctg ctg ctg ctg atg
 T   H   Q   L   E   P   R   Q   Q   L   V   V   L   G   L   Q   L   L   L   L   M 661/221
ttc acc agc ttt ccg cac atg
 F   T   S   F   P   H   M
```

```
     gag aac cac agt tgc ttt gag cac atg cac ata cct gcg ccc aga gaa gag ttc cac cag cga aac gtc aca ctc act cta
 811/271 E   N   H   S   C   F   E   H   M   H   I   P   A   P   R   E   E   F   H   Q   R   S   N   V   T   L   T   L
                                                                                    841/281                     871/291
     cgc aac ctt aaa ggg tgc tgt cgc gac act cag caa atc cag att ccc ttc agc agc tgc ctc aat gac tgc aga cac tcc gcg act
 901/301 R   N   L   K   G   C   C   R   D   T   Q   Q   I   Q   I   P   F   F   S   S   C   L   N   D   C   R   H   S   A   T
                         931/311                                                    961/321
     gtt tcc tgc gaa atg cca gac act ccg gac tac atg cct tgg ttc atc acg ggc atc tcc atc
 991/331 V   S   C   E   M   P   D   T   P   D   Y   M   P   W   F   I   T   G   I   S   I
                                                                                   1051/351
     ctg ctg gtg ggc tcc ctg atc ctg tgc atg acc tgg agg cta gct ggg cct gga agt gaa aaa tac agt gat gac acc aaa
1021/341 L   L   V   G   S   L   I   L   C   M   T   W   R   L   A   G   P   G   S   E   K   Y   S   D   D   T   K
                                                                                   1111/371                    1141/381
     tac acc gat ggc gtc cct gcg gct ctg gac ttc atc ccc cca ccg ctg aag gtc aag gtt gtg tgg atc atc tac gcc cac ccc ctc
1171/391 Y   T   D   G   V   P   A   A   L   D   F   I   P   P   P   L   K   V   K   V   V   W   I   I   Y   A   H   P   L
                                                                                   1231/411
     tac gac gac gtc aaa ttc gcc cag ttc ctc acc gcc cag cag atg gaa acg gtt gag cgg ctg ctg ctg tgc cac cag gag cag gcg atc
1261/421 Y   D   D   V   K   F   A   Q   F   L   T   A   Q   Q   M   E   T   V   E   R   L   L   L   C   S   H   Q   E   Q   A   I
                                                                                   1321/441
     tcg gag gca gga gtc atg tgg gtg ccg gag cag aag gtg gcc agc aag atc atc att gtc acc gga aag ccc gtg gtg agc gag tgt ggc
1351/451 S   E   A   G   V   M   W   V   P   E   Q   K   V   A   S   K   I   I   I   V   T   G   K   P   V   V   S   E   C   G
                                                                                   1411/471
     acg cgc gcc gat ctg ctc tcg ggg ggc gcg gag atg gac gcc aac tac tac cgc atc cag gac ctg ttc act
1441/481 T   R   A   D   L   L   S   G   G   A   E   M   D   A   N   Y   Y   R   I   Q   D   L   F   T
                                                                                   1501/501
     gca gcc atg aac ctc ccg gac ttc aag agg cca ttc cag tgc tac acc tgc tac ttc tgc agc gag gtc agt tgt gac
1471/491 A   A   M   N   L   P   D   F   K   R   P   F   Q   C   Y   T   C   Y   F   C   S   E   V   S   C   D
                                                                                   1591/531
     ggc gtc ccc gcg gcg ccg cgg tcg ctg agc ccg agg cag ctc cgc agg cag ctg ggc cgg ccg ggc cgc ctg cgc gcg gcc
1531/511 G   V   P   A   A   P   R   S   L   S   P   R   Q   L   R   R   Q   L   G   R   P   G   R   L   R   A   A
       1561/521                                                                    1681/561
     atg ttc cag ccg ggg cgg atg cac cgc gta ggg gag ctg tcg gac aac tac ctg cgg agc ccg ggc cgg cag cgc cag gat gac gcg gcc
1621/541 M   F   Q   P   G   R   M   H   R   V   G   E   L   S   D   N   Y   L   R   S   P   G   R   Q   R   Q   D   D   A   A
                                                                                   1771/591
     ctg gac agg ttc cgg gac gtc cgc gtc ccc gac tgg cag ttc gaa aac ctc tac tca gca gat gac cag gat gcc ccg tcc
1711/581 L   D   R   F   R   D   V   R   V   P   D   W   Q   F   E   N   L   Y   S   A   D   D   Q   D   A   P   S
```

FIG. 6C

```
       L    D    R    F    R    D    W    Q    V    R    C    P    D    W    F    E    C    E    N    L    Y    S    A    D    D    Q    D    A    P    S
1801/601
       ctg  gac  gag  ttt  gag  gag  gtg  cca  cgg  ctg  cct  ccg  gga  acc  ggc  atc  gtg  aag  cgg  ctg  ccc  gtg  cgc  gag  cct  ggc  tcc  cag
       L    D    E    F    E    E    V    P    R    L    P    P    G    T    G    I    V    K    R    L    P    V    R    E    P    G    S    Q
1891/631
       gcc  tgc  ctg  gcc  ata  gac  ccg  ctg  gtc  ggg  gag  gaa  gga  gca  gca  gtg  aag  ctg  cac  cct  cac  ctg  cag  ccc  cgg  ggt  cag  cca
       A    C    L    A    I    D    P    L    V    G    E    E    G    A    A    V    K    L    H    P    H    L    Q    P    R    G    Q    P
1981/661
       gcg  ccg  cag  ccc  ctc  cac  acc  ctg  gca  gag  gag  gcc  gag  ggg  gcc  gtg  gcc  ccc  ggg  ccc  ggt  gac  ttc  ctc  ccc
       A    P    Q    P    L    H    T    L    A    E    E    A    E    G    A    V    A    P    G    P    G    D    F    L    P
2071/691
       gca  gtc  cag  cag  ctg  gca  ctc  ctg  gca  gag  gag  gtg  gcc  agc  ccg  ggc  gga  aat  agc  gag  gtc  acc  gac  cca  cac  acg
       A    V    Q    Q    L    A    L    L    A    E    E    V    A    S    P    G    G    N    S    E    V    T    D    P    H    T
2161/721
       gtg  gtc  ccc  gag  gca  gcc  tgc  ccg  ctg  agc  ggc  ccg  tct  cct  gac  ctt  gct  ggg  cga  ggc  atg  gtc  ttc  ctc  gaa
       V    V    P    E    A    A    C    P    L    S    G    P    S    P    D    L    A    G    R    G    M    V    F    L    E
2191/731
       gtg  gac  ccc  gag  gag  tcg  gag  cag  ggc  atg  gcg  ccc  atc  tct  cct  gac  ctt  ttc  ttc  ctc  gaa
       V    D    P    E    E    S    E    Q    G    M    A    P    I    S    P    D    L    F    L    E
2251/751
       gtg  gac  ccc  gag  gag  tcg  gag  cag  agc  ctg  cag  agt  aga  ccc  gcc  atg  gtc  ctc  aca  gac  cca  cac  acg
       V    D    P    E    E    S    E    Q    S    L    Q    S    R    P    A    M    V    L    T    D    P    H    T
2281/761
       agc  tgc  cag  gcc  cag  tgc  agt  aga  ccc  gcc  atg  gtc  ctc  aca  gac  cca  cac  acg
       S    C    Q    A    Q    C    S    R    P    A    M    V    L    T    D    P    H    T
2341/781
       ttg  atg  ctc  tcg  ctc  ttc  gag  cag  agt  cag  agt  aga  ccc  gcc  atg  gtc  ctc  aca  gac  cca  cac  acg
       L    M    L    S    L    F    E    Q    S    Q    S    R    P    A    M    V    L    T    D    P    H    T
2371/791
       agc  ctg  cag  gcc  cag  tgc  agt  aga  ccc  gcc  atg  gtc  ctc  aca  gac  cca  cac  acg
       S    L    Q    A    Q    C    S    R    P    A    M    V    L    T    D    P    H    T
2401/801
       ccc  gcc  atg  gtc  ctc  aca  gac  cca  cac  acg
       P    A    M    V    L    T    D    P    H    T
2431/811
       atg  gag  gag  gag  gag  cag  cag  gag  gag  cag  gag  gag  cag  gag  gag
       M    E    E    E    E    Q    Q    E    E    Q    E    E    Q    E    E
2461/821
       gac  gac  gac  gac  gac  gac  gac  gac
       D    D    D    D    D    D    D    D
2491/831
       gag  gac  ctg  gag  agc  ctg  agg  agc  ctc  cag
       E    D    L    E    S    L    R    S    L    Q
2521/841
       atg  gag  gag  gag  gag  cag  cag  gag  gag  cag
       M    E    E    E    E    Q    Q    E    E    Q
2551/851
       aac  tcg  ggc  tgg  gac  acg  atg  ggg  tca  gag  ccc  agt  gca  tga  ggg  cgg  ctc
       N    S    G    W    D    T    M    G    S    E    P    S    A    *    G    R    L
```

GEAR construct 3808 – pTT5:IgkL-huIL17RA-LinkerPlad-GSS-F-H Residues 152-250 (of mature IL-17R sequence) – 5 Cys res.

DCEHARMKVTTPCMSSGSLWDPNITVETLEAHQLRVSFTLWNEST
HYQILLTSFPHMENHSCFEHMHHIPAPRPEEFHQRSNVTLTRNLK
GCCRHQVQGSSDYKDDDDKGSSHHHHHH (tag underlined)
SEQ ID NO: 37

GEAR construct 3808 – pTT5:IgkL-huIL17RA-Plad-GSS-F-H Residues 173-250 (of mature IL-17R sequence) – 3 Cys res.

PNITVETLEAHQLRVSFTLWNESTHYQILLTSFPHMENHSCFEHMH
HIPAPRPEEFHQRSNVTLTRNLKGCCRHQVQGSSDYKDDDDKHH
HHHHHH (tag underlined)
SEQ ID NO: 38

FIGURE 10

SPRRLLDFPAPVCAQEGLSCRVKNSTCLDDSWIHPKNLTPSSPKNIYINLS
VSSTQHGELVPVLHVEWTLQTDASILYLEGAELSVLQLNTNERLCVKFQF
LSMLQHHRKRWRFSFSHFVVDPGQEYEVTVHHLPKPIPDGDPNHKSKIIF
VP DCEDSKMKMTTSCVSSGSLWDPNITVETLDTQHLRVDFTLWNESTPYQ
   OLD END                                    NEW END →
VLLESFSDSENHSCFDVVKQIFAPRQEEFHQRANVTFTLSKFHWCCHHHV
QVQPFFSSCLNDCLRHAVTVPCPVISNTTVPKPVAD YIPLWEPRSH
      OLD END                              NEW END

SEQ ID NO: 40

Linker Underlined

Both made with IgK leader: METDTLLLWVLLLLWVPGSTG     SEQ ID NO: 16

C-terminal tag: GSSDYKDDDDKHHHHHHHH     SEQ ID NO: 41

SEQUENCE LISTING

```
<160> NUMBER OF SEQ ID NOS: 41

<210> SEQ ID NO 1
<211> LENGTH: 833
<212> TYPE: PRT
<213> ORGANISM: Mus musculus
<220> FEATURE:
<221> NAME/KEY: MISC_FEATURE
<223> OTHER INFORMATION: Interleukin 17 receptor A

<400> SEQUENCE: 1

Ser Pro Arg Leu Leu Asp Phe Pro Ala Pro Val Cys Ala Gln Glu Gly
1               5                   10                  15

Leu Ser Cys Arg Val Lys Asn Ser Thr Cys Leu Asp Asp Ser Trp Ile
            20                  25                  30

His Pro Lys Asn Leu Thr Pro Ser Ser Pro Lys Asn Ile Tyr Ile Asn
        35                  40                  45

Leu Ser Val Ser Ser Thr Gln His Gly Glu Leu Val Pro Val Leu His
    50                  55                  60

Val Glu Trp Thr Leu Gln Thr Asp Ala Ser Ile Leu Tyr Leu Glu Gly
65                  70                  75                  80

Ala Glu Leu Ser Val Leu Gln Leu Asn Thr Asn Glu Arg Leu Cys Val
                85                  90                  95

Lys Phe Gln Phe Leu Ser Met Leu Gln His His Arg Lys Arg Trp Arg
            100                 105                 110

Phe Ser Phe Ser His Phe Val Val Asp Pro Gly Gln Glu Tyr Glu Val
        115                 120                 125

Thr Val His His Leu Pro Lys Pro Ile Pro Asp Gly Asp Pro Asn His
    130                 135                 140

Lys Ser Lys Ile Ile Phe Val Pro Asp Cys Glu Asp Ser Lys Met Lys
145                 150                 155                 160

Met Thr Thr Ser Cys Val Ser Ser Gly Ser Leu Trp Asp Pro Asn Ile
                165                 170                 175

Thr Val Glu Thr Leu Asp Thr Gln His Leu Arg Val Asp Phe Thr Leu
            180                 185                 190

Trp Asn Glu Ser Thr Pro Tyr Gln Val Leu Leu Glu Ser Phe Ser Asp
```

```
                195                 200                 205
Ser Glu Asn His Ser Cys Phe Asp Val Val Lys Gln Ile Phe Ala Pro
210                 215                 220

Arg Gln Glu Glu Phe His Gln Arg Ala Asn Val Thr Phe Thr Leu Ser
225                 230                 235                 240

Lys Phe His Trp Cys Cys His His Val Gln Val Gln Pro Phe Phe
                245                 250                 255

Ser Ser Cys Leu Asn Asp Cys Leu Arg His Ala Val Thr Val Pro Cys
            260                 265                 270

Pro Val Ile Ser Asn Thr Thr Val Pro Lys Pro Val Ala Asp Tyr Ile
        275                 280                 285

Pro Leu Trp Val Tyr Gly Leu Ile Thr Leu Ile Ala Ile Leu Leu Val
    290                 295                 300

Gly Ser Val Ile Val Leu Ile Ile Cys Met Thr Trp Arg Leu Ser Gly
305                 310                 315                 320

Ala Asp Gln Glu Lys His Gly Asp Ser Lys Ile Asn Gly Ile Leu
                325                 330                 335

Pro Val Ala Asp Leu Thr Pro Pro Leu Arg Pro Arg Lys Val Trp
            340                 345                 350

Ile Val Tyr Ser Ala Asp His Pro Leu Tyr Val Glu Val Val Leu Lys
        355                 360                 365

Phe Ala Gln Phe Leu Ile Thr Ala Cys Gly Thr Glu Val Ala Leu Asp
    370                 375                 380

Leu Leu Glu Glu Gln Val Ile Ser Glu Val Gly Val Met Thr Trp Val
385                 390                 395                 400

Ser Arg Gln Lys Gln Glu Met Val Glu Ser Asn Ser Lys Ile Ile Ile
                405                 410                 415

Leu Cys Ser Arg Gly Thr Gln Ala Lys Trp Lys Ala Ile Leu Gly Trp
            420                 425                 430

Ala Glu Pro Ala Val Gln Leu Arg Cys Asp His Trp Lys Pro Ala Gly
        435                 440                 445

Asp Leu Phe Thr Ala Ala Met Asn Met Ile Leu Pro Asp Phe Lys Arg
    450                 455                 460

Pro Ala Cys Phe Gly Thr Tyr Val Val Cys Tyr Phe Ser Gly Ile Cys
465                 470                 475                 480

Ser Glu Arg Asp Val Pro Asp Leu Phe Asn Ile Thr Ser Arg Tyr Pro
                485                 490                 495

Leu Met Asp Arg Phe Glu Glu Val Tyr Phe Arg Ile Gln Asp Leu Glu
            500                 505                 510

Met Phe Glu Pro Gly Arg Met His His Val Arg Glu Leu Thr Gly Asp
        515                 520                 525

Asn Tyr Leu Gln Ser Pro Ser Gly Arg Gln Leu Lys Glu Ala Val Leu
    530                 535                 540

Arg Phe Gln Glu Trp Gln Thr Gln Cys Pro Asp Trp Phe Glu Arg Glu
545                 550                 555                 560

Asn Leu Cys Leu Ala Asp Gly Gln Asp Leu Pro Ser Leu Asp Glu Glu
                565                 570                 575

Val Phe Glu Asp Pro Leu Leu Pro Pro Gly Gly Ile Val Lys Gln
            580                 585                 590

Gln Pro Leu Val Arg Glu Leu Pro Ser Asp Gly Cys Leu Val Val Asp
        595                 600                 605

Val Cys Val Ser Glu Glu Glu Ser Arg Met Ala Lys Leu Asp Pro Gln
610                 615                 620
```

```
Leu Trp Pro Gln Arg Glu Leu Val Ala His Thr Leu Gln Ser Met Val
625                 630                 635                 640

Leu Pro Ala Glu Gln Val Pro Ala Ala His Val Val Glu Pro Leu His
            645                 650                 655

Leu Pro Asp Gly Ser Gly Ala Ala Gln Leu Pro Met Thr Glu Asp
            660                 665                 670

Ser Glu Ala Cys Pro Leu Leu Gly Val Gln Arg Asn Ser Ile Leu Cys
675                 680                 685

Leu Pro Val Asp Ser Asp Leu Pro Leu Cys Ser Thr Pro Met Met
690                 695                 700

Ser Pro Asp His Leu Gln Gly Asp Ala Arg Glu Gln Leu Glu Ser Leu
705                 710                 715                 720

Met Leu Ser Val Leu Gln Gln Ser Leu Ser Gly Gln Pro Leu Glu Ser
                725                 730                 735

Trp Pro Arg Pro Glu Val Val Leu Glu Gly Cys Thr Pro Ser Glu Glu
            740                 745                 750

Glu Gln Arg Gln Ser Val Gln Ser Asp Gln Gly Tyr Ile Ser Arg Ser
            755                 760                 765

Ser Pro Gln Pro Pro Glu Trp Leu Thr Glu Glu Glu Leu Glu Leu
770                 775                 780

Gly Glu Pro Val Glu Ser Leu Ser Pro Glu Glu Leu Arg Ser Leu Arg
785                 790                 795                 800

Lys Leu Gln Arg Gln Leu Phe Phe Trp Glu Leu Glu Lys Asn Pro Gly
                805                 810                 815

Trp Asn Ser Leu Glu Pro Arg Arg Pro Thr Pro Glu Glu Gln Asn Pro
            820                 825                 830

Ser

<210> SEQ ID NO 2
<211> LENGTH: 835
<212> TYPE: PRT
<213> ORGANISM: Homo sapiens
<220> FEATURE:
<221> NAME/KEY: MISC_FEATURE
<223> OTHER INFORMATION: Interleukin 17 receptor A

<400> SEQUENCE: 2

Ser Leu Arg Leu Leu Asp His Arg Ala Leu Val Cys Ser Gln Pro Gly
1               5                   10                  15

Leu Asn Cys Thr Val Lys Asn Ser Thr Cys Leu Asp Asp Ser Trp Ile
                20                  25                  30

His Pro Arg Asn Leu Thr Pro Ser Ser Pro Lys Asp Leu Gln Ile Gln
            35                  40                  45

Leu His Phe Ala His Thr Gln Gln Gly Asp Leu Phe Pro Val Ala His
    50                  55                  60

Ile Glu Trp Thr Leu Gln Thr Asp Ala Ser Ile Leu Tyr Leu Glu Gly
65                  70                  75                  80

Ala Glu Leu Ser Val Leu Gln Leu Asn Thr Asn Glu Arg Leu Cys Val
                85                  90                  95

Arg Phe Glu Phe Leu Ser Lys Leu Arg His His His Arg Arg Trp Arg
            100                 105                 110

Phe Thr Phe Ser His Phe Val Val Asp Pro Asp Gln Glu Tyr Glu Val
        115                 120                 125

Thr Val His His Leu Pro Lys Pro Ile Pro Asp Gly Asp Pro Asn His
    130                 135                 140

Gln Ser Lys Asn Phe Leu Val Pro Asp Cys Glu His Ala Arg Met Lys
```

```
                145                 150                 155                 160
Val Thr Thr Pro Cys Met Ser Ser Gly Ser Leu Trp Asp Pro Asn Ile
                165                 170                 175

Thr Val Glu Thr Leu Glu Ala His Gln Leu Arg Val Ser Phe Thr Leu
                180                 185                 190

Trp Asn Glu Ser Thr His Tyr Gln Ile Leu Leu Thr Ser Phe Pro His
                195                 200                 205

Met Glu Asn His Ser Cys Phe Glu His Met His Ile Pro Ala Pro
210                 215                 220

Arg Pro Glu Glu Phe His Gln Arg Ser Asn Val Thr Leu Thr Leu Arg
225                 230                 235                 240

Asn Leu Lys Gly Cys Cys Arg His Gln Val Gln Ile Gln Pro Phe Phe
                245                 250                 255

Ser Ser Cys Leu Asn Asp Cys Leu Arg His Ser Ala Thr Val Ser Cys
                260                 265                 270

Pro Glu Met Pro Asp Thr Pro Glu Pro Ile Pro Asp Tyr Met Pro Leu
                275                 280                 285

Trp Val Tyr Trp Phe Ile Thr Gly Ile Ser Ile Leu Leu Val Gly Ser
                290                 295                 300

Val Ile Leu Leu Ile Val Cys Met Thr Trp Arg Leu Ala Gly Pro Gly
305                 310                 315                 320

Ser Glu Lys Tyr Ser Asp Asp Thr Lys Tyr Thr Asp Gly Leu Pro Ala
                325                 330                 335

Ala Asp Leu Ile Pro Pro Pro Leu Lys Pro Arg Lys Val Trp Ile Ile
                340                 345                 350

Tyr Ser Ala Asp His Pro Leu Tyr Val Asp Val Val Leu Lys Phe Ala
                355                 360                 365

Gln Phe Leu Leu Thr Ala Cys Gly Thr Glu Val Ala Leu Asp Leu Leu
                370                 375                 380

Glu Glu Gln Ala Ile Ser Glu Ala Gly Val Met Thr Trp Val Gly Arg
385                 390                 395                 400

Gln Lys Gln Glu Met Val Glu Ser Asn Ser Lys Ile Ile Val Leu Cys
                405                 410                 415

Ser Arg Gly Thr Arg Ala Lys Trp Gln Ala Leu Leu Gly Arg Gly Ala
                420                 425                 430

Pro Val Arg Leu Arg Cys Asp His Gly Lys Pro Val Gly Asp Leu Phe
                435                 440                 445

Thr Ala Ala Met Asn Met Ile Leu Pro Asp Phe Lys Arg Pro Ala Cys
450                 455                 460

Phe Gly Thr Tyr Val Val Cys Tyr Phe Ser Glu Val Ser Cys Asp Gly
465                 470                 475                 480

Asp Val Pro Asp Leu Phe Gly Ala Ala Pro Arg Tyr Pro Leu Met Asp
                485                 490                 495

Arg Phe Glu Glu Val Tyr Phe Arg Ile Gln Asp Leu Glu Met Phe Gln
                500                 505                 510

Pro Gly Arg Met His Arg Val Gly Glu Leu Ser Gly Asp Asn Tyr Leu
                515                 520                 525

Arg Ser Pro Gly Gly Arg Gln Leu Arg Ala Ala Leu Asp Arg Phe Arg
                530                 535                 540

Asp Trp Gln Val Arg Cys Pro Asp Trp Phe Glu Cys Glu Asn Leu Tyr
545                 550                 555                 560

Ser Ala Asp Asp Gln Asp Ala Pro Ser Leu Asp Glu Glu Val Phe Glu
                565                 570                 575
```

```
Glu Pro Leu Leu Pro Pro Gly Thr Gly Ile Val Lys Arg Ala Pro Leu
            580                 585                 590

Val Arg Glu Pro Gly Ser Gln Ala Cys Leu Ala Ile Asp Pro Leu Val
        595                 600                 605

Gly Glu Glu Gly Gly Ala Ala Val Ala Lys Leu Glu Pro His Leu Gln
    610                 615                 620

Pro Arg Gly Gln Pro Ala Pro Gln Pro Leu His Thr Leu Val Leu Ala
625                 630                 635                 640

Ala Glu Glu Gly Ala Leu Val Ala Ala Val Glu Pro Gly Pro Leu Ala
                    645                 650                 655

Asp Gly Ala Ala Val Arg Leu Ala Leu Ala Gly Glu Glu Ala Cys
            660                 665                 670

Pro Leu Leu Gly Ser Pro Gly Ala Gly Arg Asn Ser Val Leu Phe Leu
                675                 680                 685

Pro Val Asp Pro Glu Asp Ser Pro Leu Gly Ser Ser Thr Pro Met Ala
            690                 695                 700

Ser Pro Asp Leu Leu Pro Glu Asp Val Arg Glu His Leu Glu Gly Leu
705                 710                 715                 720

Met Leu Ser Leu Phe Glu Gln Ser Leu Ser Cys Gln Ala Gln Gly Gly
                    725                 730                 735

Cys Ser Arg Pro Ala Met Val Leu Thr Asp Pro His Thr Pro Tyr Glu
            740                 745                 750

Glu Glu Gln Arg Gln Ser Val Gln Ser Asp Gln Gly Tyr Ile Ser Arg
                755                 760                 765

Ser Ser Pro Gln Pro Pro Glu Gly Leu Thr Glu Met Glu Glu Glu Glu
        770                 775                 780

Glu Glu Glu Gln Asp Pro Gly Lys Pro Ala Leu Pro Leu Ser Pro Glu
785                 790                 795                 800

Asp Leu Glu Ser Leu Arg Ser Leu Gln Arg Gln Leu Leu Phe Arg Gln
                    805                 810                 815

Leu Gln Lys Asn Ser Gly Trp Asp Thr Met Gly Ser Glu Ser Glu Gly
            820                 825                 830

Pro Ser Ala
        835

<210> SEQ ID NO 3
<211> LENGTH: 79
<212> TYPE: PRT
<213> ORGANISM: Mus musculus
<220> FEATURE:
<221> NAME/KEY: MISC_FEATURE
<223> OTHER INFORMATION: Mouse FN2

<400> SEQUENCE: 3

Pro Asn Ile Thr Val Glu Thr Leu Asp Thr Gln His Leu Arg Val Asp
1               5                   10                  15

Phe Thr Leu Trp Asn Glu Ser Thr Pro Tyr Gln Val Leu Leu Glu Ser
            20                  25                  30

Phe Ser Asp Ser Glu Asn His Ser Cys Phe Asp Val Val Lys Gln Ile
        35                  40                  45

Phe Ala Pro Arg Gln Glu Glu Phe His Gln Arg Ala Asn Val Thr Phe
    50                  55                  60

Thr Leu Ser Lys Phe His Trp Cys Cys His His Val Gln Val
65                  70                  75

<210> SEQ ID NO 4
<211> LENGTH: 78
```

```
<212> TYPE: PRT
<213> ORGANISM: Homo sapiens
<220> FEATURE:
<221> NAME/KEY: MISC_FEATURE
<223> OTHER INFORMATION: Human FN2

<400> SEQUENCE: 4

Pro Asn Ile Thr Val Glu Thr Leu Glu Ala His Gln Leu Arg Val Ser
1               5                   10                  15

Phe Thr Leu Trp Asn Glu Ser Thr His Tyr Gln Ile Leu Leu Thr Ser
            20                  25                  30

Phe Pro His Met Glu Asn His Ser Cys Phe Glu His Met His His Ile
        35                  40                  45

Pro Ala Pro Arg Pro Glu Glu Phe His Gln Arg Ser Asn Val Thr Leu
    50                  55                  60

Thr Leu Arg Asn Leu Lys Gly Cys Cys Arg His Gln Val Gln
65                  70                  75

<210> SEQ ID NO 5
<211> LENGTH: 21
<212> TYPE: PRT
<213> ORGANISM: Mus musculus
<220> FEATURE:
<221> NAME/KEY: MISC_FEATURE
<223> OTHER INFORMATION: Mouse linker

<400> SEQUENCE: 5

Asp Cys Glu Asp Ser Lys Met Lys Met Thr Thr Ser Cys Val Ser Ser
1               5                   10                  15

Gly Ser Leu Trp Asp
            20

<210> SEQ ID NO 6
<211> LENGTH: 21
<212> TYPE: PRT
<213> ORGANISM: Homo sapiens
<220> FEATURE:
<221> NAME/KEY: MISC_FEATURE
<223> OTHER INFORMATION: Human linker

<400> SEQUENCE: 6

Asp Cys Glu His Ala Arg Met Lys Val Thr Thr Pro Cys Met Ser Ser
1               5                   10                  15

Gly Ser Leu Trp Asp
            20

<210> SEQ ID NO 7
<211> LENGTH: 100
<212> TYPE: PRT
<213> ORGANISM: Mus musculus
<220> FEATURE:
<221> NAME/KEY: MISC_FEATURE
<223> OTHER INFORMATION: Mouse FN2 + linker

<400> SEQUENCE: 7

Asp Cys Glu Asp Ser Lys Met Lys Met Thr Thr Ser Cys Val Ser Ser
1               5                   10                  15

Gly Ser Leu Trp Asp Pro Asn Ile Thr Val Glu Thr Leu Asp Thr Gln
            20                  25                  30

His Leu Arg Val Asp Phe Thr Leu Trp Asn Glu Ser Thr Pro Tyr Gln
        35                  40                  45

Val Leu Leu Glu Ser Phe Ser Asp Ser Glu Asn His Ser Cys Phe Asp
    50                  55                  60
```

Val Val Lys Gln Ile Phe Ala Pro Arg Gln Glu Phe His Gln Arg
65                  70                  75                  80

Ala Asn Val Thr Phe Thr Leu Ser Lys Phe His Trp Cys Cys His
                85                  90                  95

His Val Gln Val
            100

<210> SEQ ID NO 8
<211> LENGTH: 99
<212> TYPE: PRT
<213> ORGANISM: Homo sapiens
<220> FEATURE:
<221> NAME/KEY: MISC_FEATURE
<223> OTHER INFORMATION: Human FN2 + linker

<400> SEQUENCE: 8

Asp Cys Glu His Ala Arg Met Lys Val Thr Thr Pro Cys Met Ser Ser
1               5                   10                  15

Gly Ser Leu Trp Asp Pro Asn Ile Thr Val Glu Thr Leu Glu Ala His
            20                  25                  30

Gln Leu Arg Val Ser Phe Thr Leu Trp Asn Glu Ser Thr His Tyr Gln
        35                  40                  45

Ile Leu Leu Thr Ser Phe Pro His Met Glu Asn His Ser Cys Phe Glu
50                  55                  60

His Met His His Ile Pro Ala Pro Arg Pro Glu Phe His Gln Arg
65                  70                  75                  80

Ser Asn Val Thr Leu Thr Leu Arg Asn Leu Lys Gly Cys Cys Arg His
                85                  90                  95

Gln Val Gln

<210> SEQ ID NO 9
<211> LENGTH: 34
<212> TYPE: PRT
<213> ORGANISM: Mus musculus
<220> FEATURE:
<221> NAME/KEY: MISC_FEATURE
<223> OTHER INFORMATION: Mouse C-terminal extension

<400> SEQUENCE: 9

Gln Pro Phe Phe Ser Ser Cys Leu Asn Asp Cys Leu Arg His Ala Val
1               5                   10                  15

Thr Val Pro Cys Pro Val Ile Ser Asn Thr Thr Val Pro Lys Pro Val
            20                  25                  30

Ala Asp

<210> SEQ ID NO 10
<211> LENGTH: 33
<212> TYPE: PRT
<213> ORGANISM: Homo sapiens
<220> FEATURE:
<221> NAME/KEY: MISC_FEATURE
<223> OTHER INFORMATION: Human C-terminal extension

<400> SEQUENCE: 10

Ile Gln Pro Phe Phe Ser Ser Cys Leu Asn Asp Cys Leu Arg His Ser
1               5                   10                  15

Ala Thr Val Ser Cys Pro Glu Met Pro Asp Thr Pro Glu Pro Ile Pro
            20                  25                  30

Asp

<210> SEQ ID NO 11

```
<211> LENGTH: 113
<212> TYPE: PRT
<213> ORGANISM: Mus musculus
<220> FEATURE:
<221> NAME/KEY: MISC_FEATURE
<223> OTHER INFORMATION: Mouse FN2 + C-terminal extension

<400> SEQUENCE: 11

Pro Asn Ile Thr Val Glu Thr Leu Asp Thr Gln His Leu Arg Val Asp
1               5                   10                  15

Phe Thr Leu Trp Asn Glu Ser Thr Pro Tyr Gln Val Leu Leu Glu Ser
            20                  25                  30

Phe Ser Asp Ser Glu Asn His Ser Cys Phe Asp Val Val Lys Gln Ile
        35                  40                  45

Phe Ala Pro Arg Gln Glu Glu Phe His Gln Arg Ala Asn Val Thr Phe
    50                  55                  60

Thr Leu Ser Lys Phe His Trp Cys Cys His His Val Gln Val Gln
65                  70                  75                  80

Pro Phe Phe Ser Ser Cys Leu Asn Asp Cys Leu Arg His Ala Val Thr
                85                  90                  95

Val Pro Cys Pro Val Ile Ser Asn Thr Thr Val Pro Lys Pro Val Ala
            100                 105                 110

Asp

<210> SEQ ID NO 12
<211> LENGTH: 111
<212> TYPE: PRT
<213> ORGANISM: Homo sapiens
<220> FEATURE:
<221> NAME/KEY: MISC_FEATURE
<223> OTHER INFORMATION: Human FN2 + C-terminal extension

<400> SEQUENCE: 12

Pro Asn Ile Thr Val Glu Thr Leu Glu Ala His Gln Leu Arg Val Ser
1               5                   10                  15

Phe Thr Leu Trp Asn Glu Ser Thr His Tyr Gln Ile Leu Leu Thr Ser
            20                  25                  30

Phe Pro His Met Glu Asn His Ser Cys Phe Glu His Met His His Ile
        35                  40                  45

Pro Ala Pro Arg Pro Glu Phe His Gln Arg Ser Asn Val Thr Leu
    50                  55                  60

Thr Leu Arg Asn Leu Lys Gly Cys Cys Arg His Gln Val Gln Ile Gln
65                  70                  75                  80

Pro Phe Phe Ser Ser Cys Leu Asn Asp Cys Leu Arg His Ser Ala Thr
                85                  90                  95

Val Ser Cys Pro Glu Met Pro Asp Thr Pro Gly Pro Ile Pro Asp
            100                 105                 110

<210> SEQ ID NO 13
<211> LENGTH: 134
<212> TYPE: PRT
<213> ORGANISM: Mus musculus
<220> FEATURE:
<221> NAME/KEY: MISC_FEATURE
<223> OTHER INFORMATION: Mouse FN2 + linker + C-terminal extension

<400> SEQUENCE: 13

Asp Cys Glu Asp Ser Lys Met Lys Met Thr Thr Ser Cys Val Ser Ser
1               5                   10                  15

Gly Ser Leu Trp Asp Pro Asn Ile Thr Val Glu Thr Leu Asp Thr Gln
            20                  25                  30
```

```
His Leu Arg Val Asp Phe Thr Leu Trp Asn Glu Ser Thr Pro Tyr Gln
        35                  40                  45

Val Leu Leu Glu Ser Phe Ser Asp Ser Glu Asn His Ser Cys Phe Asp
 50                  55                  60

Val Val Lys Gln Ile Phe Ala Pro Arg Gln Glu Phe His Gln Arg
 65                  70                  75                  80

Ala Asn Val Thr Phe Thr Leu Ser Lys Phe His Trp Cys His His
                85                  90                  95

His Val Gln Val Gln Pro Phe Phe Ser Ser Cys Leu Asn Asp Cys Leu
                100                 105                 110

Arg His Ala Val Thr Val Pro Cys Pro Val Ile Ser Asn Thr Thr Val
                115                 120                 125

Pro Lys Pro Val Ala Asp
        130

<210> SEQ ID NO 14
<211> LENGTH: 132
<212> TYPE: PRT
<213> ORGANISM: Homo sapiens
<220> FEATURE:
<221> NAME/KEY: MISC_FEATURE
<223> OTHER INFORMATION: Human FN2 + linker + C-terminal extension

<400> SEQUENCE: 14

Asp Cys Glu His Ala Arg Met Lys Val Thr Thr Pro Cys Met Ser Ser
 1               5                  10                  15

Gly Ser Leu Trp Asp Pro Asn Ile Thr Val Thr Leu Glu Ala His
                20                  25                  30

Gln Leu Arg Val Ser Phe Thr Leu Trp Asn Glu Ser Thr His Tyr Gln
        35                  40                  45

Ile Leu Leu Thr Ser Phe Pro His Met Glu Asn His Ser Cys Phe Glu
 50                  55                  60

His Met His His Ile Pro Ala Pro Arg Pro Glu Glu Phe His Gln Arg
 65                  70                  75                  80

Ser Asn Val Thr Leu Thr Leu Arg Asn Leu Lys Gly Cys Cys Arg His
                85                  90                  95

Gln Val Gln Ile Gln Pro Phe Phe Ser Ser Cys Leu Asn Asp Cys Leu
                100                 105                 110

Arg His Ser Ala Thr Val Ser Cys Pro Glu Met Pro Asp Thr Pro Glu
                115                 120                 125

Pro Ile Pro Asp
        130

<210> SEQ ID NO 15
<211> LENGTH: 3
<212> TYPE: PRT
<213> ORGANISM: Artificial sequence
<220> FEATURE:
<223> OTHER INFORMATION: N-terminal extension for FN2 without linker

<400> SEQUENCE: 15

Leu Trp Asp
 1

<210> SEQ ID NO 16
<211> LENGTH: 20
<212> TYPE: PRT
<213> ORGANISM: Artificial sequence
<220> FEATURE:
<223> OTHER INFORMATION: Secretion signal of IgK
```

<400> SEQUENCE: 16

Met Glu Thr Asp Thr Leu Leu Leu Trp Val Leu Leu Trp Val Pro
1               5                   10                  15

Gly Ser Thr Gly
            20

<210> SEQ ID NO 17
<211> LENGTH: 31
<212> TYPE: PRT
<213> ORGANISM: Homo sapiens
<220> FEATURE:
<221> NAME/KEY: MISC_FEATURE
<223> OTHER INFORMATION: Secretion signal of human IL-17RA

<400> SEQUENCE: 17

Met Gly Ala Ala Arg Ser Pro Pro Ser Ala Val Pro Gly Pro Leu Leu
1               5                   10                  15

Gly Leu Leu Leu Leu Leu Leu Gly Val Leu Ala Pro Gly Gly Ala
            20                  25                  30

<210> SEQ ID NO 18
<211> LENGTH: 3288
<212> TYPE: DNA
<213> ORGANISM: Mus musculus
<220> FEATURE:
<221> NAME/KEY: misc_feature
<223> OTHER INFORMATION: Interleukin 17 receptor A (IL17RA)

<400> SEQUENCE: 18

| | | | | | |
|---|---|---|---|---|---|
| gtcgactgga | acgagacgac | ctgctgccga | cgagcgccag | tcctcggccg | ggaaagccat | 60 |
| cgcgggccct | cgctgtcgcg | cggagccagc | tgcgagcgct | ccgcgaccgg | gccgagggct | 120 |
| atggcgattc | ggcgctgctg | ccacgggtc | gtccccgggc | ccgcgctggg | atggctgctt | 180 |
| ctgctgctga | acgttctggc | cccggccgc | gcctccccgc | gcctcctcga | cttcccggct | 240 |
| ccggtctgcg | cgcaggaggg | gctgagctgc | agagtcaaga | atagtacttg | tctggatgac | 300 |
| agctggatcc | accccaaaaa | cctgaccccg | tcttccccaa | aaacatcta | tatcaatctt | 360 |
| agtgttttcct | ctacccagca | cggagaatta | gtccctgtgt | tgcatgttga | gtggaccctg | 420 |
| cagacagatg | ccagcatcct | gtacctcgag | ggtgcagagc | tgtccgtcct | gcagctgaac | 480 |
| accaatgagc | ggctgtgtgt | caagttccag | tttctgtcca | tgctgcagca | tcaccgtaag | 540 |
| cggtggcggt | tttccttcag | ccactttgtg | gtagatcctg | gccaggagta | tgaagtgact | 600 |
| gttcaccacc | tgccgaagcc | catccctgat | ggggacccaa | accacaaatc | caagatcatc | 660 |
| tttgtgcctg | actgtgagga | cagcaagatg | aagatgacta | cctcatgcgt | gagctcaggc | 720 |
| agcctttggg | atcccaacat | cactgtggag | accttggaca | cacagcatct | gcgagtggac | 780 |
| ttcaccctgt | ggaatgaatc | cacccccttac | caggtcctgc | tggaaagttt | ctccgactca | 840 |
| gagaaccaca | gctgctttga | tgtcgttaaa | caaatatttg | cgcccaggca | agaagaattc | 900 |
| catcagcgag | ctaatgtcac | attcactcta | agcaagtttc | actggtgctg | ccatcaccac | 960 |
| gtgcaggtcc | agcccttctt | cagcagctgc | ctaaatgact | gttgagaca | cgctgtgact | 1020 |
| gtgccctgcc | cagtaatctc | aaataccaca | gttcccaagc | cagttgcaga | ctacattccc | 1080 |
| ctgtgggtgt | atggcctcat | cacactcatc | gccattctgc | tggtgggatc | tgtcatcgtg | 1140 |
| ctgatcatct | gtatgaccctg | gaggctttct | ggcgccgatc | aagagaaaca | tggtgatgac | 1200 |
| tccaaaatca | atggcatctt | gcccgtagca | gacctgactc | ccccaccct | gaggcccagg | 1260 |
| aaggtctgga | tcgtctactc | ggccgaccac | ccctctatg | tggaggtggt | cctaaagttc | 1320 |

```
gcccagttcc tgatcactgc ctgtggcact gaagtagccc ttgacctcct ggaagagcag    1380
gttatctctg aggtgggggt catgacctgg gtgagccgac agaagcagga gatggtggag    1440
agcaactcca aaatcatcat cctgtgttcc cgaggcaccc aagcaaagtg gaaagctatc    1500
ttgggttggg ctgagcctgc tgtccagcta cggtgtgacc actggaagcc tgctggggac    1560
cttttcactg cagccatgaa catgatcctg ccagacttca gaggccagc ctgcttcggc     1620 acctacgttg tttgctactt cagtggcatc tgtagtgaga gggatgtccc cgacctcttc    1680
aacatcacct ccaggtaccc actcatggac agatttgagg aggtttactt ccggatccag    1740
gacctggaga tgtttgaacc cggccggatg caccatgtca gagagctcac agggacaat    1800 tacctgcaga gccctagtgg ccggcagctc aaggaggctg tgcttaggtt ccaggagtgg    1860
caaacccagt gccccgactg gttcgagcgt gagaacctct gcttagctga tggccaagat    1920
cttccctccc tggatgaaga agtgtttgaa gacccactgc tgccaccagg gggaggaatt    1980
gtcaaacagc agcccctggt gcgggaactc ccatctgacg gctgccttgt ggtagatgtc    2040
tgtgtcagtg aggaagaaag tagaatggca aagctggacc ctcagctatg ccacagaga    2100 gagctagtgg ctcacaccct ccaaagcatg gtgctgccag cagagcaggt ccctgcagct    2160
catgtggtgg agcctctcca tctcccagac ggcagtggag cagctgccca gctgcccatg    2220
acagaggaca gcgaggcttg cccgctgctg ggggtccaga ggaacagcat cctttgcctc    2280
cccgtggact cagatgactt gccactctgt agcaccccaa tgatgtcacc tgaccacctc    2340
caaggcgatg caagagagca gctagaaagc ctaatgctct cggtgctgca gcagagcctg    2400
agtggacagc ccctggagag ctggccgagg ccagaggtgg tcctcgaggg ctgcacaccc    2460
tctgaggagg agcagcggca gtcggtgcag tcggaccagg gctacatctc caggagctcc    2520
ccgcagcccc ccgagtggct cacggaggag gaaagagctag aactgggtga gcccgttgag    2580
tctctctctc ctgaggaact acggagcctg aggaagctcc agaggcagct tttcttctgg    2640
gagctcgaga agaaccctgg ctggaacagc ttggagccac ggagacccac cccagaagag    2700
cagaatccct cctaggcctc ctgagcctgc tacttaagag ggtgtatatt gtactctgtg    2760
tgtgcgtgcg tgtgtgtgtg tgtgtgtgtg tgtgtgtgcg tgtgtgtgtg tgtgtgtgtg    2820
tgtgtgtgtg tgtagtgccc ggcttagaaa tgtgaacatc tgaatctgac atagtgttgt    2880
atacctgaag tcccagcact tgggaactga gacttgatga tctcctgaag ccaggtgttc    2940
agggccagtg tgaaaacata gcaagacctc agagaaatca atgcagacat cttggtactg    3000
atccctaaac acaccccttt ccctgataac ccgacatgag catctggtca tcattgcaca    3060
agaatccaca gcccgttccc agagctcata gccaagtgtg ttgctcattc cttgaatatt    3120
tattctgtac ctactattca tcagacattt ggaattcaaa aacaagttac atgacacagc    3180
cttagccact aagaagctta aaattcggta aggatgtaaa attagccagg atgaatagag    3240
ggctgctgcc ctggctgcag aagagcaggt cgtctcgttc cagtcgac                 3288
```

<210> SEQ ID NO 19
<211> LENGTH: 8
<212> TYPE: PRT
<213> ORGANISM: Artificial sequence
<220> FEATURE:
<223> OTHER INFORMATION: Expression marker -- FLAG tag

<400> SEQUENCE: 19

Asp Tyr Lys Asp Asp Asp Asp Lys
1               5

```
<210> SEQ ID NO 20
<211> LENGTH: 6
<212> TYPE: PRT
<213> ORGANISM: Artificial sequence
<220> FEATURE:
<223> OTHER INFORMATION: Purification tag

<400> SEQUENCE: 20

His His His His His His
1               5

<210> SEQ ID NO 21
<211> LENGTH: 20
<212> TYPE: PRT
<213> ORGANISM: Artificial sequence
<220> FEATURE:
<223> OTHER INFORMATION: Spacer/Tag

<400> SEQUENCE: 21

Gly Ser Ser Asp Tyr Lys Asp Asp Asp Lys Gly Ser His His
1               5                   10                  15

His His His His
            20

<210> SEQ ID NO 22
<211> LENGTH: 115
<212> TYPE: PRT
<213> ORGANISM: Mus musculus
<220> FEATURE:
<221> NAME/KEY: MISC_FEATURE
<223> OTHER INFORMATION: Mouse FN1

<400> SEQUENCE: 22

Thr Pro Ser Ser Pro Lys Asn Ile Tyr Ile Asn Leu Ser Val Ser Ser
1               5                   10                  15

Thr Gln His Gly Glu Leu Val Pro Val Leu His Val Glu Trp Thr Leu
            20                  25                  30

Gln Thr Asp Ala Ser Ile Leu Tyr Leu Glu Gly Ala Glu Leu Ser Val
        35                  40                  45

Leu Gln Leu Asn Thr Asn Glu Arg Leu Cys Val Lys Phe Gln Phe Leu
    50                  55                  60

Ser Met Leu Gln His His Arg Lys Arg Trp Arg Phe Ser Phe Ser His
65                  70                  75                  80

Phe Val Val Asp Pro Gly Gln Glu Tyr Glu Val Thr Val His Leu
                85                  90                  95

Pro Lys Pro Ile Pro Asp Gly Asp Pro Asn His Lys Ser Lys Ile Ile
            100                 105                 110

Phe Val Pro
        115

<210> SEQ ID NO 23
<211> LENGTH: 115
<212> TYPE: PRT
<213> ORGANISM: Homo sapiens
<220> FEATURE:
<221> NAME/KEY: MISC_FEATURE
<223> OTHER INFORMATION: Human FN1

<400> SEQUENCE: 23

Thr Pro Ser Ser Pro Lys Asp Leu Gln Ile Gln Leu His Phe Ala His
1               5                   10                  15

Thr Gln Gln Gly Asp Leu Phe Pro Val Ala His Ile Glu Trp Thr Leu
            20                  25                  30
```

```
Gln Thr Asp Ala Ser Ile Leu Tyr Leu Glu Gly Ala Glu Leu Ser Val
            35                  40                  45

Leu Gln Leu Asn Thr Asn Glu Arg Leu Cys Val Arg Phe Glu Phe Leu
 50                  55                  60

Ser Lys Leu Arg His His His Arg Arg Trp Arg Phe Thr Phe Ser His
 65                  70                  75                  80

Phe Val Val Asp Pro Asp Gln Glu Tyr Glu Val Thr Val His His Leu
                 85                  90                  95

Pro Lys Pro Ile Pro Asp Gly Asp Pro Asn His Gln Ser Lys Asn Phe
                100                 105                 110

Leu Val Pro
       115

<210> SEQ ID NO 24
<211> LENGTH: 3429
<212> TYPE: DNA
<213> ORGANISM: Homo sapiens
<220> FEATURE:
<221> NAME/KEY: misc_feature
<223> OTHER INFORMATION: Interleukin 17 receptor A (IL17RA)

<400> SEQUENCE: 24
ctgggcccgg gctggaagcc ggaagcgagc aaagtggagc cgactcgaac tccaccgcgg     60
aaaagaaagc ctcagaacgt tcgttcgctg cgtccccagc cggggccgag ccctccgcga    120
cgccagccgg ccatgggggg ccgcacgcag cccgccgtcc gctgtcccgg ggcccctgct    180
ggggctgctc ctgctgctcc tgggcgtgct ggccccgggt ggcgcctccc tgcgactcct    240
ggaccaccgg cgctggtct  gctcccagcc ggggctaaac tgcacggtca agaatagtac    300
ctgcctggat gacagctgga ttcaccctcg aaacctgacc cctcctccc  caaaggacct    360 gcagatccag ctgcactttg cccacaccca acaaggagac ctgttccccg tggctcacat    420
cgaatggaca ctgcagacag acgccagcat cctgtacctc gagggtgcag agttatctgt    480
cctgcagctg aacaccaatg aacgtttgtg cgtcaggttt gagtttctgt ccaaactgag    540
gcatcaccac aggcggtggc gttttacctt cagccacttt gtggttgacc ctgaccagga    600
atatgaggtg accgttcacc acctgcccaa gccatccct  gatgggggacc caaaccacca    660 gtccaagaat ttccttgtgc ctgactgtga gcacgccagg atgaaggtaa ccacgccatg    720
catgagctca ggcagcctgt gggaccccaa catcaccgtg gagaccctgg aggcccacca    780
gctgcgtgtg agcttcaccc tgtggaacga atctacccat taccagatcc tgctgaccag    840
ttttccgcac atggagaacc acagttgctt tgagcacatg caccacatac ctgcgcccag    900
accagaagag ttccaccagc gatccaacgt cacactcact ctacgcaacc ttaaagggtg    960
ctgtcgccac caagtgcaga tccagccctt cttcagcagc tgcctcaatg actgcctcag   1020
acactccgcg actgtttcct gcccagaaat gccagacact ccagaaccaa ttccggacta   1080
catgcccctg tgggtgtact ggttcatcac gggcatctcc atcctgctgg tgggctccgt   1140
catcctgctc atcgtctgca tgaccctgga gctagctggg cctggaagtg aaaaatacag   1200
tgatgacacc aaatacaccg atggcctgcc tgcggctgac ctgatccccc caccgctgaa   1260
gcccaggaag gtctgatca  tctactcagc cgaccacccc ctctacgtgg acgtggtcct   1320
gaaattcgcc cagttcctgc tcaccgcctg cggcacggaa gtggccctgg acctgctgga   1380
agagcaggcc atctcggagg caggagtcat gacctgggtg gccgtcaga  agcaggagat   1440 ggtggagagc aactctaaga tcatcgtcct gtgctcccgc ggcacgcgcg ccaagtggca   1500
```

```
ggcgctcctg ggccggggg  cgcctgtgcg gctgcgctgc gaccacggaa agcccgtggg   1560
ggacctgttc actgcagcca tgaacatgat cctcccggac ttcaagaggc cagcctgctt   1620
cggcacctac gtagtctgct acttcagcga ggtcagctgt gacggcgacg tccccgacct   1680
gttcggcgcg cgccgcggt  acccgctcat ggacaggttc gaggaggtgt acttccgcat   1740
ccaggacctg gagatgttcc agccgggccg catgcaccgc gtaggggagc tgtcggggga   1800
caactacctg cggagcccgg gcggcaggca gctccgcgcc gccctggaca ggttccggga   1860
ctggcaggtc cgctgtcccg actggttcga atgtgagaac ctctactcag cagatgacca   1920
ggatgccccg tccctggacg aagaggtgtt tgaggagcca ctgctgcctc cgggaaccgg   1980
catcgtgaag cgggcgcccc tggtgcgcga gcctggctcc caggcctgcc tggccataga   2040
cccgctggtc ggggaggaag gaggagcagc agtggcaaag ctggaacctc acctgcagcc   2100
ccggggtcag ccagcgccgc agcccctcca caccctggtg ctcgccgcag aggaggggc    2160 cctggtggcc gcggtggagc ctgggcccct ggctgacggt gccgcagtcc ggctggcact   2220
ggcgggggag ggcgaggcct gcccgctgct gggcagcccg ggcgctgggc gaaatagcgt   2280
cctcttcctc cccgtggacc ccgaggactc gccccttggc agcagcaccc ccatggcgtc   2340
tcctgacctc cttccagagg acgtgaggga gcacctcgaa ggcttgatgc tctcgctctt   2400
cgagcagagt ctgagctgcc aggcccaggg gggctgcagt agacccgcca tggtcctcac   2460
agacccacac acgccctacg aggaggagca gcggcagtca gtgcagtctg accagggcta   2520
catctccagg agctccccgc agcccccgga gggactcacg gaaatggagg aagaggagga   2580
agaggagcag gacccaggga gccggccct  gccactctct cccgaggacc tggagagcct   2640
gaggagcctc cagcggcagc tgcttttccg ccagctgcag aagaactcgg gctgggacac   2700
gatggggtca gagtcagagg ggcccagtgc atgagggcgg ctccccaggg accgcccaga   2760
tcccagcttt gagagaggag tgtgtgtgca cgtattcatc tgtgtgtaca tgtctgcatg   2820
tgtatatgtt cgtgtgtgaa atgtaggctt taaaatgtaa atgtctggat tttaatccca   2880
ggcatccctc ctaactttc  tttgtgcagc ggtctggtta tcgtctatcc ccaggggaat   2940
ccacacagcc cgctcccagg agctaatggt agagcgtcct tgaggctcca ttattcgttc   3000
attcagcatt tattgtgcac ctactatgtg gcgggcattt gggataccaa gataaattgc   3060
atgcggcatg gccccagcca tgaaggaact taaccgctag tgccgaggac acgttaaacg   3120
aacaggatgg gccgggcacg gtggctcacg cctgtaatcc cagcacactg ggaggccgag   3180
gcaggtggat cactctgagg tcaggagttt gagccagcct ggccaacatg gtgaaacccc   3240
atctccacta aaaatagaaa aattagccgg gcatggtgac acatgcctgt agtcctagct   3300
acttgggagg ctgaggcagg agaattgctt gaatctggga ggcagaggtt gcagtgagcc   3360
gagattgtgc cattgcactg cagcctggat gacagagcga gactctatct caaaaaaaaa   3420
aaaaaaaaa                                                           3429
```

<210> SEQ ID NO 25
<211> LENGTH: 312
<212> TYPE: PRT
<213> ORGANISM: Homo sapiens
<220> FEATURE:
<221> NAME/KEY: MISC_FEATURE
<223> OTHER INFORMATION: Full length -- human

<400> SEQUENCE: 25

Leu Arg Leu Leu Asp His Arg Ala Leu Val Cys Ser Gln Pro Gly Leu
1               5                   10                  15

```
Asn Cys Thr Val Lys Asn Ser Thr Cys Leu Asp Asp Ser Trp Ile His
         20                  25                  30

Pro Arg Asn Leu Thr Pro Ser Ser Pro Lys Asp Leu Gln Ile Gln Leu
         35                  40                  45

His Phe Ala His Thr Gln Gln Gly Asp Leu Phe Pro Val Ala His Ile
 50                  55                  60

Glu Trp Thr Leu Gln Thr Asp Ala Ser Ile Leu Tyr Leu Glu Gly Ala
 65                  70                  75                  80

Glu Leu Ser Val Leu Gln Leu Asn Thr Asn Glu Arg Leu Cys Val Arg
                 85                  90                  95

Phe Glu Phe Leu Ser Lys Leu Arg His His Arg Arg Trp Arg Phe
                100                 105                 110

Thr Phe Ser His Phe Val Val Asp Pro Asp Gln Glu Tyr Glu Val Thr
                115                 120                 125

Val His His Leu Pro Lys Pro Ile Pro Asp Gly Asp Pro Asn His Gln
130                 135                 140

Ser Lys Asn Phe Leu Val Pro Asp Cys Glu His Ala Arg Met Lys Val
145                 150                 155                 160

Thr Thr Pro Cys Met Ser Ser Gly Ser Leu Trp Asp Pro Asn Ile Thr
                165                 170                 175

Val Glu Thr Leu Glu Ala His Gln Leu Arg Val Ser Phe Thr Leu Trp
                180                 185                 190

Asn Glu Ser Thr His Tyr Gln Ile Leu Leu Thr Ser Phe Pro His Met
                195                 200                 205

Glu Asn His Ser Cys Phe Glu His Met His His Ile Pro Ala Pro Arg
210                 215                 220

Pro Glu Glu Phe His Gln Arg Ser Asn Val Thr Leu Thr Leu Arg Asn
225                 230                 235                 240

Leu Lys Gly Cys Cys Arg His Gln Val Gln Ile Gln Pro Phe Phe Ser
                245                 250                 255

Ser Cys Leu Asn Asp Cys Leu Arg His Ser Ala Thr Val Ser Cys Pro
                260                 265                 270

Glu Met Pro Asp Thr Pro Glu Pro Ile Pro Asp Tyr Met Pro Leu Trp
                275                 280                 285

Glu Pro Arg Ser Gly Ser Ser Asp Tyr Lys Asp Asp Asp Lys Gly
290                 295                 300

Ser Ser His His His His His His
305                 310

<210> SEQ ID NO 26
<211> LENGTH: 280
<212> TYPE: PRT
<213> ORGANISM: Homo sapiens
<220> FEATURE:
<221> NAME/KEY: MISC_FEATURE
<223> OTHER INFORMATION: New end -- human

<400> SEQUENCE: 26

Leu Arg Leu Leu Asp His Arg Ala Leu Val Cys Ser Gln Pro Gly Leu
 1               5                   10                  15

Asn Cys Thr Val Lys Asn Ser Thr Cys Leu Asp Asp Ser Trp Ile His
                 20                  25                  30

Pro Arg Asn Leu Thr Pro Ser Ser Pro Lys Asp Leu Gln Ile Gln Leu
                 35                  40                  45

His Phe Ala His Thr Gln Gln Gly Asp Leu Phe Pro Val Ala His Ile
 50                  55                  60
```

```
Glu Trp Thr Leu Gln Thr Asp Ala Ser Ile Leu Tyr Leu Glu Gly Ala
 65                  70                  75                  80

Glu Leu Ser Val Leu Gln Leu Asn Thr Asn Glu Arg Leu Cys Val Arg
                 85                  90                  95

Phe Glu Phe Leu Ser Lys Leu Arg His His His Arg Arg Trp Arg Phe
                100                 105                 110

Thr Phe Ser His Phe Val Val Asp Pro Asp Gln Glu Tyr Glu Val Thr
            115                 120                 125

Val His His Leu Pro Lys Pro Ile Pro Asp Gly Asp Pro Asn His Gln
        130                 135                 140

Ser Lys Asn Phe Leu Val Pro Asp Cys Glu His Ala Arg Met Lys Val
145                 150                 155                 160

Thr Thr Pro Cys Met Ser Ser Gly Ser Leu Trp Asp Pro Asn Ile Thr
                165                 170                 175

Val Glu Thr Leu Glu Ala His Gln Leu Arg Val Ser Phe Thr Leu Trp
            180                 185                 190

Asn Glu Ser Thr His Tyr Gln Ile Leu Leu Thr Ser Phe Pro His Met
        195                 200                 205

Glu Asn His Ser Cys Phe Glu His Met His His Ile Pro Ala Pro Arg
210                 215                 220

Pro Glu Glu Phe His Gln Arg Ser Asn Val Thr Leu Thr Leu Arg Asn
225                 230                 235                 240

Leu Lys Gly Cys Cys Arg His Gln Val Gln Ile Gln Pro Phe Phe Ser
                245                 250                 255

Ser Cys Leu Asn Asp Cys Leu Arg His Ser Ala Thr Val Ser Cys Pro
            260                 265                 270

Glu Met Pro Asp Thr Pro Glu Pro
            275                 280

<210> SEQ ID NO 27
<211> LENGTH: 250
<212> TYPE: PRT
<213> ORGANISM: Homo sapiens
<220> FEATURE:
<221> NAME/KEY: MISC_FEATURE
<223> OTHER INFORMATION: Old end -- human

<400> SEQUENCE: 27

Leu Arg Leu Leu Asp His Arg Ala Leu Val Cys Ser Gln Pro Gly Leu
  1               5                  10                  15

Asn Cys Thr Val Lys Asn Ser Thr Cys Leu Asp Asp Ser Trp Ile His
                 20                  25                  30

Pro Arg Asn Leu Thr Pro Ser Ser Pro Lys Asp Leu Gln Ile Gln Leu
             35                  40                  45

His Phe Ala His Thr Gln Gln Gly Asp Leu Phe Pro Val Ala His Ile
 50                  55                  60

Glu Trp Thr Leu Gln Thr Asp Ala Ser Ile Leu Tyr Leu Glu Gly Ala
 65                  70                  75                  80

Glu Leu Ser Val Leu Gln Leu Asn Thr Asn Glu Arg Leu Cys Val Arg
                 85                  90                  95

Phe Glu Phe Leu Ser Lys Leu Arg His His His Arg Arg Trp Arg Phe
                100                 105                 110

Thr Phe Ser His Phe Val Val Asp Pro Asp Gln Glu Tyr Glu Val Thr
            115                 120                 125

Val His His Leu Pro Lys Pro Ile Pro Asp Gly Asp Pro Asn His Gln
        130                 135                 140
```

```
Ser Lys Asn Phe Leu Val Pro Asp Cys Glu His Ala Arg Met Lys Val
145                 150                 155                 160

Thr Thr Pro Cys Met Ser Ser Gly Ser Leu Trp Asp Pro Asn Ile Thr
                165                 170                 175

Val Glu Thr Leu Glu Ala His Gln Leu Arg Val Ser Phe Thr Leu Trp
            180                 185                 190

Asn Glu Ser Thr His Tyr Gln Ile Leu Leu Thr Ser Phe Pro His Met
        195                 200                 205

Glu Asn His Ser Cys Phe Glu His Met His His Ile Pro Ala Pro Arg
    210                 215                 220

Pro Glu Glu Phe His Gln Arg Ser Asn Val Thr Leu Thr Leu Arg Asn
225                 230                 235                 240

Leu Lys Gly Cys Cys Arg His Gln Val Gln
                245                 250

<210> SEQ ID NO 28
<211> LENGTH: 296
<212> TYPE: PRT
<213> ORGANISM: Mus musculus
<220> FEATURE:
<221> NAME/KEY: MISC_FEATURE
<223> OTHER INFORMATION: Full length -- mouse

<400> SEQUENCE: 28

Ser Pro Arg Leu Leu Asp Phe Pro Ala Pro Val Cys Ala Gln Glu Gly
1               5                   10                  15

Leu Ser Cys Arg Val Lys Asn Ser Thr Cys Leu Asp Asp Ser Trp Ile
            20                  25                  30

His Pro Lys Asn Leu Thr Pro Ser Ser Pro Lys Asn Ile Tyr Ile Asn
        35                  40                  45

Leu Ser Val Ser Ser Thr Gln His Gly Glu Leu Val Pro Val Leu His
    50                  55                  60

Val Glu Trp Thr Leu Gln Thr Asp Ala Ser Ile Leu Tyr Leu Glu Gly
65                  70                  75                  80

Ala Glu Leu Ser Val Leu Gln Leu Asn Thr Asn Glu Arg Leu Cys Val
                85                  90                  95

Lys Phe Gln Phe Leu Ser Met Leu Gln His His Arg Lys Arg Trp Arg
            100                 105                 110

Phe Ser Phe Ser His Phe Val Val Asp Pro Gly Gln Glu Tyr Glu Val
        115                 120                 125

Thr Val His His Leu Pro Lys Pro Ile Pro Asp Gly Asp Pro Asn His
    130                 135                 140

Lys Ser Lys Ile Ile Phe Val Pro Asp Cys Glu Asp Ser Lys Met Lys
145                 150                 155                 160

Met Thr Thr Ser Cys Val Ser Ser Gly Ser Leu Trp Asp Pro Asn Ile
                165                 170                 175

Thr Val Glu Thr Leu Asp Thr Gln His Leu Arg Val Asp Phe Thr Leu
            180                 185                 190

Trp Asn Glu Ser Thr Pro Tyr Gln Val Leu Leu Glu Ser Phe Ser Asp
        195                 200                 205

Ser Glu Asn His Ser Cys Phe Asp Val Val Lys Gln Ile Phe Ala Pro
    210                 215                 220

Arg Gln Glu Glu Phe His Gln Arg Ala Asn Val Thr Phe Thr Leu Ser
225                 230                 235                 240

Lys Phe Trp His Cys Cys His His Val Gln Val Gln Pro Phe Phe
                245                 250                 255
```

-continued

Ser Ser Cys Leu Asn Asp Cys Leu Arg His Ala Val Thr Val Pro Cys
        260                 265                 270

Pro Val Ile Ser Asn Thr Thr Val Pro Lys Pro Val Ala Asp Tyr Ile
        275                 280                 285

Pro Leu Trp Glu Pro Arg Ser His
        290                 295

<210> SEQ ID NO 29
<211> LENGTH: 286
<212> TYPE: PRT
<213> ORGANISM: Mus musculus
<220> FEATURE:
<221> NAME/KEY: MISC_FEATURE
<223> OTHER INFORMATION: New End -- mouse

<400> SEQUENCE: 29

Ser Pro Arg Leu Leu Asp Phe Pro Ala Pro Val Cys Ala Gln Glu Gly
1               5                   10                  15

Leu Ser Cys Arg Val Lys Asn Ser Thr Cys Leu Asp Asp Ser Trp Ile
            20                  25                  30

His Pro Lys Asn Leu Thr Pro Ser Ser Pro Lys Asn Ile Tyr Ile Asn
        35                  40                  45

Leu Ser Val Ser Ser Thr Gln His Gly Glu Leu Val Pro Val Leu His
    50                  55                  60

Val Glu Trp Thr Leu Gln Thr Asp Ala Ser Ile Leu Tyr Leu Glu Gly
65                  70                  75                  80

Ala Glu Leu Ser Val Leu Gln Leu Asn Thr Asn Glu Arg Leu Cys Val
                85                  90                  95

Lys Phe Gln Phe Leu Ser Met Leu Gln His His Arg Lys Arg Trp Arg
            100                 105                 110

Phe Ser Phe Ser His Phe Val Val Asp Pro Gly Gln Glu Tyr Glu Val
        115                 120                 125

Thr Val His His Leu Pro Lys Pro Ile Pro Asp Gly Asp Pro Asn His
    130                 135                 140

Lys Ser Lys Ile Ile Phe Val Pro Asp Cys Glu Asp Ser Lys Met Lys
145                 150                 155                 160

Met Thr Thr Ser Cys Val Ser Ser Gly Ser Leu Trp Asp Pro Asn Ile
                165                 170                 175

Thr Val Glu Thr Leu Asp Thr Gln His Leu Arg Val Asp Phe Thr Leu
            180                 185                 190

Trp Asn Glu Ser Thr Pro Tyr Gln Val Leu Leu Glu Ser Phe Ser Asp
        195                 200                 205

Ser Glu Asn His Ser Cys Phe Asp Val Val Lys Gln Ile Phe Ala Pro
    210                 215                 220

Arg Gln Glu Glu Phe His Gln Arg Ala Asn Val Thr Phe Thr Leu Ser
225                 230                 235                 240

Lys Phe His Trp Cys Cys His His Val Gln Val Gln Pro Phe Phe
                245                 250                 255

Ser Ser Cys Leu Asn Asp Cys Leu Arg His Ala Val Thr Val Pro Cys
        260                 265                 270

Pro Val Ile Ser Asn Thr Thr Val Pro Lys Pro Val Ala Asp
        275                 280                 285

<210> SEQ ID NO 30
<211> LENGTH: 252
<212> TYPE: PRT
<213> ORGANISM: Mus musculus
<220> FEATURE:

<221> NAME/KEY: MISC_FEATURE
<223> OTHER INFORMATION: Old End -- mouse

<400> SEQUENCE: 30

Ser Pro Arg Leu Leu Asp Phe Pro Ala Pro Val Cys Ala Gln Glu Gly
1               5                   10                  15

Leu Ser Cys Arg Val Lys Asn Ser Thr Cys Leu Asp Asp Ser Trp Ile
            20                  25                  30

His Pro Lys Asn Leu Thr Pro Ser Pro Lys Asn Ile Tyr Ile Asn
        35                  40                  45

Leu Ser Val Ser Ser Thr Gln His Gly Glu Leu Val Pro Val Leu His
    50                  55                  60

Val Glu Trp Thr Leu Gln Thr Asp Ala Ser Ile Leu Tyr Leu Glu Gly
65                  70                  75                  80

Ala Glu Leu Ser Val Leu Gln Leu Asn Thr Asn Glu Arg Leu Cys Val
                85                  90                  95

Lys Phe Gln Phe Leu Ser Met Leu Gln His His Arg Lys Arg Trp Arg
            100                 105                 110

Phe Ser Phe Ser His Phe Val Val Asp Pro Gly Gln Glu Tyr Glu Val
        115                 120                 125

Thr Val His His Leu Pro Lys Pro Ile Pro Asp Gly Asp Pro Asn His
    130                 135                 140

Lys Ser Lys Ile Ile Phe Val Pro Asp Cys Glu Asp Ser Lys Met Lys
145                 150                 155                 160

Met Thr Thr Ser Cys Val Ser Ser Gly Ser Leu Trp Asp Pro Asn Ile
                165                 170                 175

Thr Val Glu Thr Leu Asp Thr Gln His Leu Arg Val Asp Phe Thr Leu
            180                 185                 190

Trp Asn Glu Ser Thr Pro Tyr Gln Val Leu Leu Glu Ser Phe Ser Asp
        195                 200                 205

Ser Glu Asn His Ser Cys Phe Asp Val Val Lys Gln Ile Phe Ala Pro
    210                 215                 220

Arg Gln Glu Glu Phe His Gln Arg Ala Asn Val Thr Phe Thr Leu Ser
225                 230                 235                 240

Lys Phe His Trp Cys Cys His His His Val Gln Val
                245                 250

<210> SEQ ID NO 31
<211> LENGTH: 99
<212> TYPE: PRT
<213> ORGANISM: Artificial sequence
<220> FEATURE:
<223> OTHER INFORMATION: hIL-17RA-FN2/linker-PLAD

<400> SEQUENCE: 31

Asp Cys Glu His Ala Arg Met Lys Val Thr Thr Pro Cys Met Ser Ser
1               5                   10                  15

Gly Ser Leu Trp Asp Pro Asn Ile Thr Val Glu Thr Leu Glu Ala His
            20                  25                  30

Gln Leu Arg Val Ser Phe Thr Leu Trp Asn Glu Ser Thr His Tyr Gln
        35                  40                  45

Ile Leu Leu Thr Ser Phe Pro His Met Glu Asn His Ser Cys Phe Glu
    50                  55                  60

His Met His His Ile Pro Ala Pro Arg Pro Glu Glu Phe His Gln Arg
65                  70                  75                  80

Ser Asn Val Thr Leu Thr Leu Arg Asn Leu Lys Gly Cys Cys Arg His
                85                  90                  95

Gln Val Gln

<210> SEQ ID NO 32
<211> LENGTH: 78
<212> TYPE: PRT
<213> ORGANISM: Artificial sequence
<220> FEATURE:
<223> OTHER INFORMATION: hIL-17RA-FN2 PLAD

<400> SEQUENCE: 32

```
Pro Asn Ile Thr Val Glu Thr Leu Glu Ala His Gln Leu Arg Val Ser
1               5                   10                  15

Phe Thr Leu Trp Asn Glu Ser Thr His Tyr Gln Ile Leu Leu Thr Ser
            20                  25                  30

Phe Pro His Met Glu Asn His Ser Cys Phe Glu His Met His His Ile
        35                  40                  45

Pro Ala Pro Arg Pro Glu Glu Phe His Gln Arg Ser Asn Val Thr Leu
    50                  55                  60

Thr Leu Arg Asn Leu Lys Gly Cys Cys Arg His Gln Val Gln
65                  70                  75
```

<210> SEQ ID NO 33
<211> LENGTH: 100
<212> TYPE: PRT
<213> ORGANISM: Artificial sequence
<220> FEATURE:
<223> OTHER INFORMATION: mIL-17RA-FN2/linker PLAD

<400> SEQUENCE: 33

```
Asp Cys Glu Asp Ser Lys Met Lys Met Thr Thr Ser Cys Val Ser Ser
1               5                   10                  15

Gly Ser Leu Trp Asp Pro Asn Ile Thr Val Glu Thr Leu Asp Thr Gln
            20                  25                  30

His Leu Arg Val Asp Phe Thr Leu Trp Asn Glu Ser Thr Pro Tyr Gln
        35                  40                  45

Val Leu Leu Glu Ser Phe Ser Asp Ser Glu Asn His Ser Cys Phe Asp
    50                  55                  60

Val Val Lys Gln Ile Phe Ala Pro Arg Gln Glu Glu Phe His Gln Arg
65                  70                  75                  80

Ala Asn Val Thr Phe Thr Leu Ser Lys Phe His Trp Cys Cys His His
                85                  90                  95

His Val Gln Val
            100
```

<210> SEQ ID NO 34
<211> LENGTH: 79
<212> TYPE: PRT
<213> ORGANISM: Artificial sequence
<220> FEATURE:
<223> OTHER INFORMATION: mIL-17RA-FN2 PLAD

<400> SEQUENCE: 34

```
Pro Asn Ile Thr Val Glu Thr Leu Asp Thr Gln His Leu Arg Val Asp
1               5                   10                  15

Phe Thr Leu Trp Asn Glu Ser Thr Pro Tyr Gln Val Leu Leu Glu Ser
            20                  25                  30

Phe Ser Asp Ser Glu Asn His Ser Cys Phe Asp Val Val Lys Gln Ile
        35                  40                  45

Phe Ala Pro Arg Gln Glu Glu Phe His Gln Arg Ala Asn Val Thr Phe
    50                  55                  60
```

Thr Leu Ser Lys Phe His Trp Cys Cys His His Val Gln Val
65                  70              75

<210> SEQ ID NO 35
<211> LENGTH: 99
<212> TYPE: PRT
<213> ORGANISM: Artificial sequence
<220> FEATURE:
<223> OTHER INFORMATION: GEAR construct 3808 - pTT5:IgkL-huIL17RA-
      LinkerPlad-GSS-F-H Residues 152-250 (of mature IL-17R sequence) -
      5 Cys res

<400> SEQUENCE: 35

Asp Cys Glu His Ala Arg Met Lys Val Thr Thr Pro Cys Met Ser Ser
1               5                   10                  15

Gly Ser Leu Trp Asp Pro Asn Ile Thr Val Glu Thr Leu Glu Ala His
            20                  25                  30

Gln Leu Arg Val Ser Phe Thr Leu Trp Asn Glu Ser Thr His Tyr Gln
        35                  40                  45

Ile Leu Leu Thr Ser Phe Pro His Met Glu Asn His Ser Cys Phe Glu
    50                  55                  60

His Met His His Ile Pro Ala Pro Arg Pro Glu Phe His Gln Arg
65                  70                  75                  80

Ser Asn Val Thr Leu Thr Leu Arg Asn Leu Lys Gly Cys Cys Arg His
                85                  90                  95

Gln Val Gln

<210> SEQ ID NO 36
<211> LENGTH: 78
<212> TYPE: PRT
<213> ORGANISM: Artificial sequence
<220> FEATURE:
<223> OTHER INFORMATION: GEAR construct 3808 - pTT5:IgkL-huIL17RA-Plad-
      GSS-F-H Residues 173-250 (of mature IL-17R sequence) - 3 Cys res.

<400> SEQUENCE: 36

Pro Asn Ile Thr Val Glu Thr Leu Glu Ala His Gln Leu Arg Val Ser
1               5                   10                  15

Phe Thr Leu Trp Asn Glu Ser Thr His Tyr Gln Ile Leu Leu Thr Ser
            20                  25                  30

Phe Pro His Met Glu Asn His Ser Cys Phe Glu His Met His His Ile
        35                  40                  45

Pro Ala Pro Arg Pro Glu Phe His Gln Arg Ser Asn Val Thr Leu
    50                  55                  60

Thr Leu Arg Asn Leu Lys Gly Cys Cys Arg His Gln Val Gln
65                  70                  75

<210> SEQ ID NO 37
<211> LENGTH: 119
<212> TYPE: PRT
<213> ORGANISM: Homo sapiens

<400> SEQUENCE: 37

Asp Cys Glu His Ala Arg Met Lys Val Thr Thr Pro Cys Met Ser Ser
1               5                   10                  15

Gly Ser Leu Trp Asp Pro Asn Ile Thr Val Glu Thr Leu Glu Ala His
            20                  25                  30

Gln Leu Arg Val Ser Phe Thr Leu Trp Asn Glu Ser Thr His Tyr Gln
        35                  40                  45

Ile Leu Leu Thr Ser Phe Pro His Met Glu Asn His Ser Cys Phe Glu

```
              50                  55                  60
His Met His His Ile Pro Ala Pro Arg Pro Glu Glu Phe His Gln Arg
 65                  70                  75                  80

Ser Asn Val Thr Leu Thr Leu Arg Asn Leu Lys Gly Cys Cys Arg His
                 85                  90                  95

Gln Val Gln Gly Ser Ser Asp Tyr Lys Asp Asp Asp Lys Gly Ser
            100                 105                 110

Ser His His His His His
            115

<210> SEQ ID NO 38
<211> LENGTH: 97
<212> TYPE: PRT
<213> ORGANISM: Homo sapiens

<400> SEQUENCE: 38

Pro Asn Ile Thr Val Glu Thr Leu Glu Ala His Gln Leu Arg Val Ser
 1               5                  10                  15

Phe Thr Leu Trp Asn Glu Ser Thr His Tyr Gln Ile Leu Leu Thr Ser
                20                  25                  30

Phe Pro His Met Glu Asn His Ser Cys Phe Glu His Met His His Ile
             35                  40                  45

Pro Ala Pro Arg Pro Glu Phe His Gln Arg Ser Asn Val Thr Leu
 50                  55                  60

Thr Leu Arg Asn Leu Lys Gly Cys Cys Arg His Gln Val Gln Gly Ser
 65                  70                  75                  80

Ser Asp Tyr Lys Asp Asp Asp Lys His His His His His His
                 85                  90                  95

His

<210> SEQ ID NO 39
<211> LENGTH: 312
<212> TYPE: PRT
<213> ORGANISM: Homo sapiens

<400> SEQUENCE: 39

Leu Arg Leu Leu Asp His Arg Ala Leu Val Cys Ser Gln Pro Gly Leu
 1               5                  10                  15

Asn Cys Thr Val Lys Asn Ser Thr Cys Leu Asp Asp Ser Trp Ile His
                20                  25                  30

Pro Arg Asn Leu Thr Pro Ser Ser Pro Lys Asp Leu Gln Ile Gln Leu
             35                  40                  45

His Phe Ala His Thr Gln Gln Gly Asp Leu Phe Pro Val Ala His Ile
 50                  55                  60

Glu Trp Thr Leu Gln Thr Asp Ala Ser Ile Leu Tyr Leu Glu Gly Ala
 65                  70                  75                  80

Glu Leu Ser Val Leu Gln Leu Asn Thr Asn Glu Arg Leu Cys Val Arg
                85                  90                  95

Phe Glu Phe Leu Ser Lys Leu Arg His His His Arg Arg Trp Arg Phe
            100                 105                 110

Thr Phe Ser His Phe Val Val Asp Pro Asp Gln Glu Tyr Glu Val Thr
            115                 120                 125

Val His His Leu Pro Lys Pro Ile Pro Asp Gly Asp Pro Asn His Gln
        130                 135                 140

Ser Lys Asn Phe Leu Val Pro Asp Cys Glu His Ala Arg Met Lys Val
145                 150                 155                 160
```

```
Thr Thr Pro Cys Met Ser Ser Gly Ser Leu Trp Asp Pro Asn Ile Thr
            165                 170                 175
Val Glu Thr Leu Glu Ala His Gln Leu Arg Val Ser Phe Thr Leu Trp
        180                 185                 190
Asn Glu Ser Thr His Tyr Gln Ile Leu Leu Thr Ser Phe Pro His Met
    195                 200                 205
Glu Asn His Ser Cys Phe Glu His Met His His Ile Pro Ala Pro Arg
210                 215                 220
Pro Glu Glu Phe His Gln Arg Ser Asn Val Thr Leu Thr Leu Arg Asn
225                 230                 235                 240
Leu Tyr Gly Cys Cys Arg His Gln Val Gln Ile Gln Pro Phe Phe Ser
            245                 250                 255
Ser Cys Leu Asn Asp Cys Leu Arg His Ser Ala Thr Val Ser Cys Pro
        260                 265                 270
Glu Met Pro Asp Thr Pro Glu Pro Ile Pro Asp Tyr Met Pro Leu Trp
    275                 280                 285
Glu Pro Arg Ser Gly Ser Ser Asp Tyr Lys Asp Asp Asp Lys Gly
290                 295                 300
Ser Ser His His His His His His
305                 310

<210> SEQ ID NO 40
<211> LENGTH: 296
<212> TYPE: PRT
<213> ORGANISM: Homo sapiens

<400> SEQUENCE: 40

Ser Pro Arg Leu Leu Asp Phe Pro Ala Pro Val Cys Ala Gln Glu Gly
1               5                   10                  15
Leu Ser Cys Arg Val Lys Asn Ser Thr Cys Leu Asp Asp Ser Trp Ile
            20                  25                  30
His Pro Lys Asn Leu Thr Pro Ser Ser Pro Lys Asn Ile Tyr Ile Asn
        35                  40                  45
Leu Ser Val Ser Ser Thr Gln His Gly Glu Leu Val Pro Val Leu His
    50                  55                  60
Val Glu Trp Thr Leu Gln Thr Asp Ala Ser Ile Leu Tyr Leu Glu Gly
65                  70                  75                  80
Ala Glu Leu Ser Val Leu Gln Leu Asn Thr Asn Glu Arg Leu Cys Val
            85                  90                  95
Lys Phe Gln Phe Leu Ser Met Leu Gln His His Arg Lys Arg Trp Arg
        100                 105                 110
Phe Ser Phe Ser His Phe Val Val Asp Pro Gly Gln Glu Tyr Glu Val
    115                 120                 125
Thr Val His His Leu Pro Lys Pro Ile Pro Asp Gly Asp Pro Asn His
130                 135                 140
Lys Ser Lys Ile Ile Phe Val Pro Asp Cys Glu Asp Ser Lys Met Lys
145                 150                 155                 160
Met Thr Thr Ser Cys Val Ser Ser Gly Ser Leu Trp Asp Pro Asn Ile
            165                 170                 175
Thr Val Glu Thr Leu Asp Thr Gln His Leu Arg Val Asp Phe Thr Leu
        180                 185                 190
Trp Asn Glu Ser Thr Pro Tyr Gln Val Leu Leu Glu Ser Phe Ser Asp
    195                 200                 205
Ser Glu Asn His Ser Cys Phe Asp Val Val Lys Gln Ile Phe Ala Pro
210                 215                 220
```

-continued

```
Arg Gln Glu Glu Phe His Gln Arg Ala Asn Val Thr Phe Thr Leu Ser
225                 230                 235                 240

Lys Phe His Trp Cys Cys His His His Val Gln Val Gln Pro Phe Phe
                245                 250                 255

Ser Ser Cys Leu Asn Asp Cys Leu Arg His Ala Val Thr Val Pro Cys
            260                 265                 270

Pro Val Ile Ser Asn Thr Thr Val Pro Lys Pro Val Ala Asp Tyr Ile
            275                 280             285

Pro Leu Trp Glu Pro Arg Ser His
    290                 295

<210> SEQ ID NO 41
<211> LENGTH: 19
<212> TYPE: PRT
<213> ORGANISM: Artificial Sequence
<220> FEATURE:
<223> OTHER INFORMATION: C-terminal tag

<400> SEQUENCE: 41

Gly Ser Ser Asp Tyr Lys Asp Asp Asp Lys His His His His His
1               5                   10                  15

His His His
```

PRE-LIGAND ASSEMBLY DOMAIN OF THE IL-17 RECEPTOR

CROSS-REFERENCE TO RELATED APPLICATIONS

This patent application claims the benefit of U.S. Provisional Patent Application No. 60/925,367, filed on Apr. 20, 2007.

BACKGROUND OF THE INVENTION

Anti-cytokine receptor drugs have had a tremendous clinical impact on autoimmune disease, as evidenced by the effectiveness of IL-1β and TNFα blockade for rheumatoid arthritis and psoriasis. However, since not all patients respond to these treatments, new strategies are still needed. A fundamental understanding of receptor structure and subunit interactions is a key for developing novel therapeutics. In this regard, IL-17 and the closely related cytokine IL-17F are the defining cytokines of a newly-described subset of Th cells termed "Th17." Th17 cells and IL-17 have both been implicated as causative factors for many autoimmune diseases, including rheumatoid arthritis (RA), colitis and multiple sclerosis/experimental autoimmune encephalomyelitis. The first known IL-17 binding protein, IL17RA, is the founder of a unique receptor superfamily, and there is considerable interest in targeting IL-17 or its receptor as anti-cytokine therapeutics. However, the composition, subunit dynamics and ligand binding contact sites of the IL-17 binding complex are poorly defined. It was previously demonstrated that an IL-17 binding complex contains at least two subunits of IL-17RA, which are pre-assembled in the cell membrane prior to contact with ligand (either IL-17 or IL-17F). The region within IL-17RA that mediates receptor multimerization is unknown. Thus, there is a need to characterize this receptor at a molecular level and to develop methods and compositions for targeting it and/or IL-17.

BRIEF SUMMARY OF THE INVENTION

The invention provides a Pre-Ligand Assembly Domain (PLAD) polypeptide comprising an amino acid sequence of a domain of an IL-17 Receptor (IL-17R) family member, a functional fragment thereof, or an amino acid sequence which is significantly identical to a domain of an IL-17 Receptor (IL-17R) family member, or a functional fragment thereof. The PLAD polypeptides of the invention advantageously inhibit multimerization of a receptor complex comprising an IL-17R family member, which in turn inhibits the signal transduction mediated by an IL-17 ligand and also inhibits the binding of the IL-17 ligand to its receptor complex.

IL-17R signal transduction refers to the effect of extracellular binding of one or more ligands, such as an IL-17 ligand family member, to initiate one or more IL-17R-mediated or IL-17-mediated intracellular activities such as those defined herein.

Also provided by the invention are isolated PLAD-binding polypeptides, e.g., antibodies and avimers, which specifically bind to a PLAD polypeptide as described herein. The PLAD-binding polypeptides also inhibit multimerization of a receptor complex comprising an IL-17R family member and consequently inhibit the IL-17-ligand mediated signal transduction. Further embodiments include PLAD-binding polypeptides that bind an IL-17R family member and inhibit IL-17 ligand binding to its receptor and/or receptor complex.

Related materials including chimeric proteins, fusion proteins, conjugates, nucleic acids, vectors, and host cells are further provided herein.

As IL-17 ligand-mediated signal transduction has been implicated in some diseases, the invention further provides methods of treating an inflammatory or autoimmune disease, in which the inventive PLAD polypeptides, PLAD-binding polypeptides, or related materials are administered to a subject in need thereof.

Methods of inhibiting IL-17-mediated signal transduction, methods of inhibiting IL-17 ligand binding, methods of inhibiting multimerization of IL-17R family member-containing complexes, and methods of inhibiting the production of at least one cytokine, chemokine, matrix metalloproteinase, or other molecule associated with IL-17 signal transduction are furthermore provided. The inventive methods comprise contacting cells with a PLAD polypeptide, PLAD-binding polypeptide, or related material.

BRIEF DESCRIPTION OF THE FIGURES

FIG. 1A is a set of computer-generated illustrations of the predicted structure of the IL-17RA extracellular domain (ECD). IL-17RA contains two putative fibronectin-like III (FN) domains: FN1 and FN2. FN2 is located C-terminal to FN1. PHYRE software was used to predict the location of FN domains and linker region (not shown) within the mouse IL-17RA ECD. The analysis predicted β-sheets in both the FN1 and FN2, α-helices in FN2, unstructured loops in FN1 and FN2, and turn structures in FN1. Sequences of each subdomain are shown with the position of the first and last amino acid indicated.

FIG. 1B is a set of schematic diagrams of the FRET and yeast 2-hybrid constructs used in the study of Examples 1 to 6. AD=activation domain, BD=DNA binding domain, YFP=yellow fluorescence protein; CFP=cyan fluorescence protein; FL=full length; TM=transmembrane; IL-17RAΔ=IL-17RA truncated at residue 526. SEFIR is the major signaling domain in the IL-17RA cytoplasmic tail.

Figure 4:
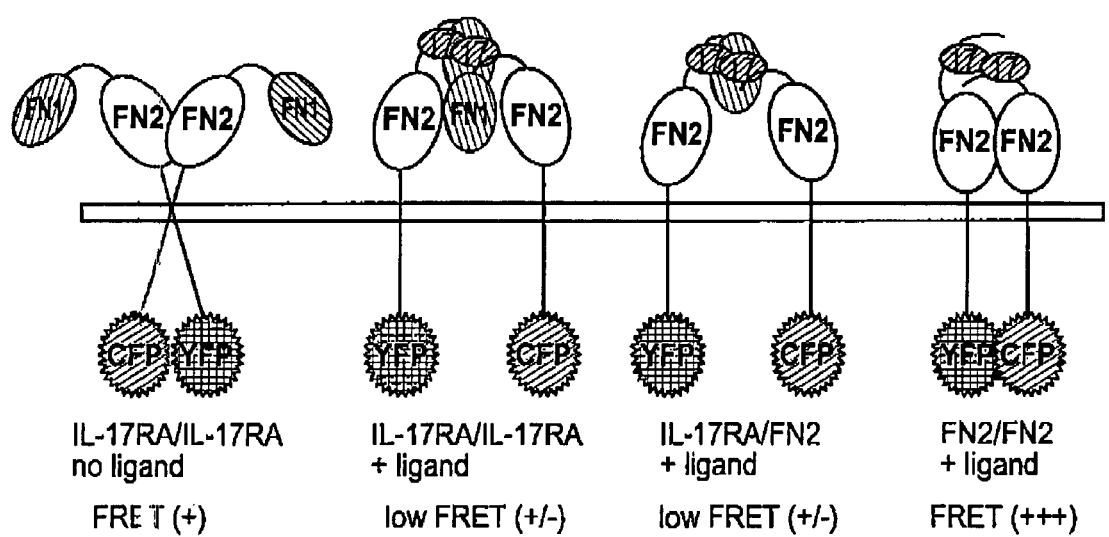

FIG. 4 is a model of IL-17RA subunit reconfiguration. Data from these and prior studies suggest that the cytoplasmic tails of IL-17RA are held in proximity prior to ligand binding, but are separated (or perhaps rotated) in the presence of IL-17. Based on the FRET data, the presence of at least one FN1 domain is sufficient to mediate this ligand-induced subunit reconfiguration. However, in the absence of both FN1 domains, the cytoplasmic tails and their associated fluorophores show an increased association. "17" indicates dimeric IL-17 ligand, which requires the linker region. A possible model to explain these data is shown.

FIGS. 5A to 5C presents the nucleotide and amino acid sequence for murine IL-17RA which is set forth herein as SEQ ID NOs: 18 and 1, respectively.

FIGS. 6A to 6C presents the nucleotide and amino acid sequence for human IL-17RA which are set forth herein as SEQ ID NOs: 24 and 2, respectively.

FIG. 7 illustrates the amino acid sequences of two PLAD polypeptides encoded by the first generation of constructs. The top demonstrates the amino acid sequence of SEQ ID NO: 37, which is a PLAD polypeptide containing the FN2 and linker of human IL-17RA, while the bottom demonstrates the amino acid sequence of SEQ ID NO: 38, which is a PLAD polypeptide containing just the FN2 of human IL-17RA. The spacer/tag is underlined.

Figure 8:
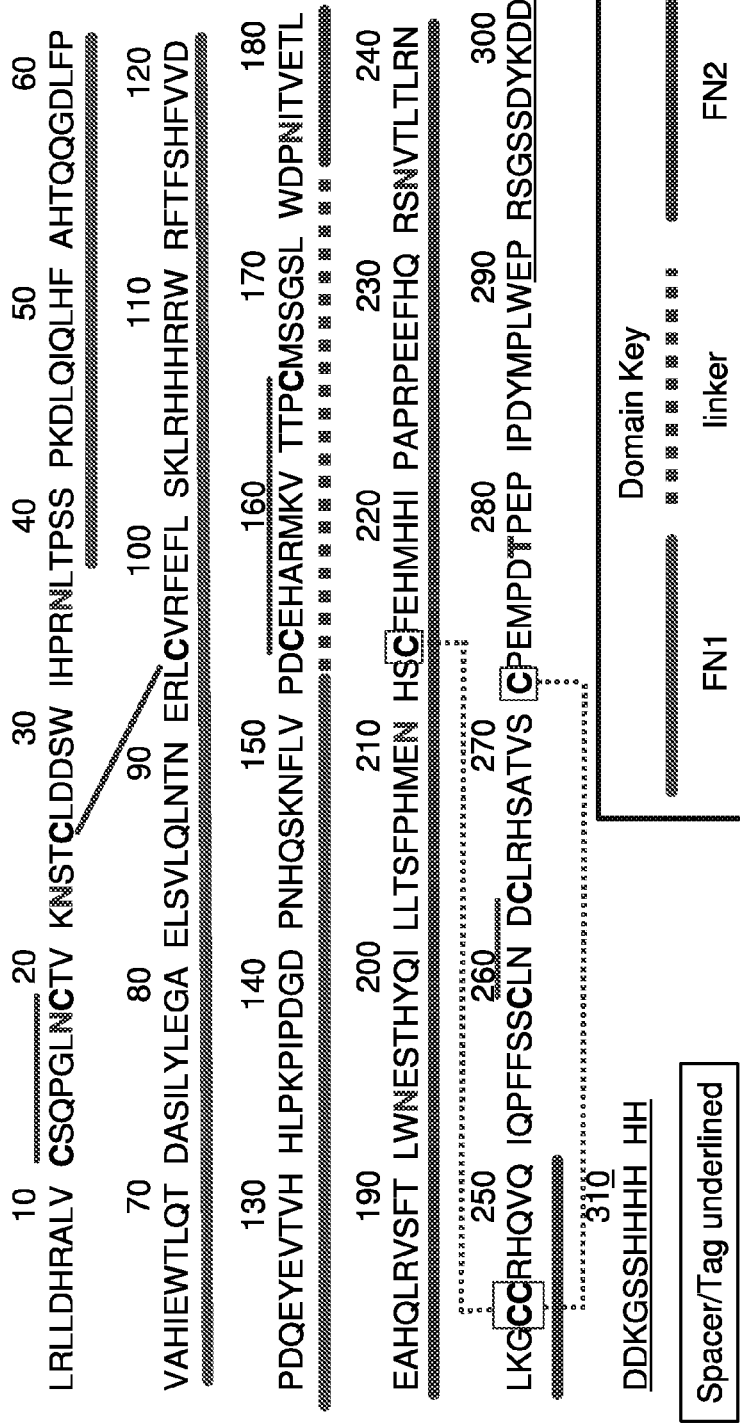

FIG. 8 illustrates the amino acid sequence of SEQ ID NO: 26 which is a human PLAD polypeptide and also shows the disulfide bridges thereof. Narrow dotted lines indicate ambiguous disulfide bridges and narrow solid lines indicate confirmed disulfide bridges.

Figure 9:
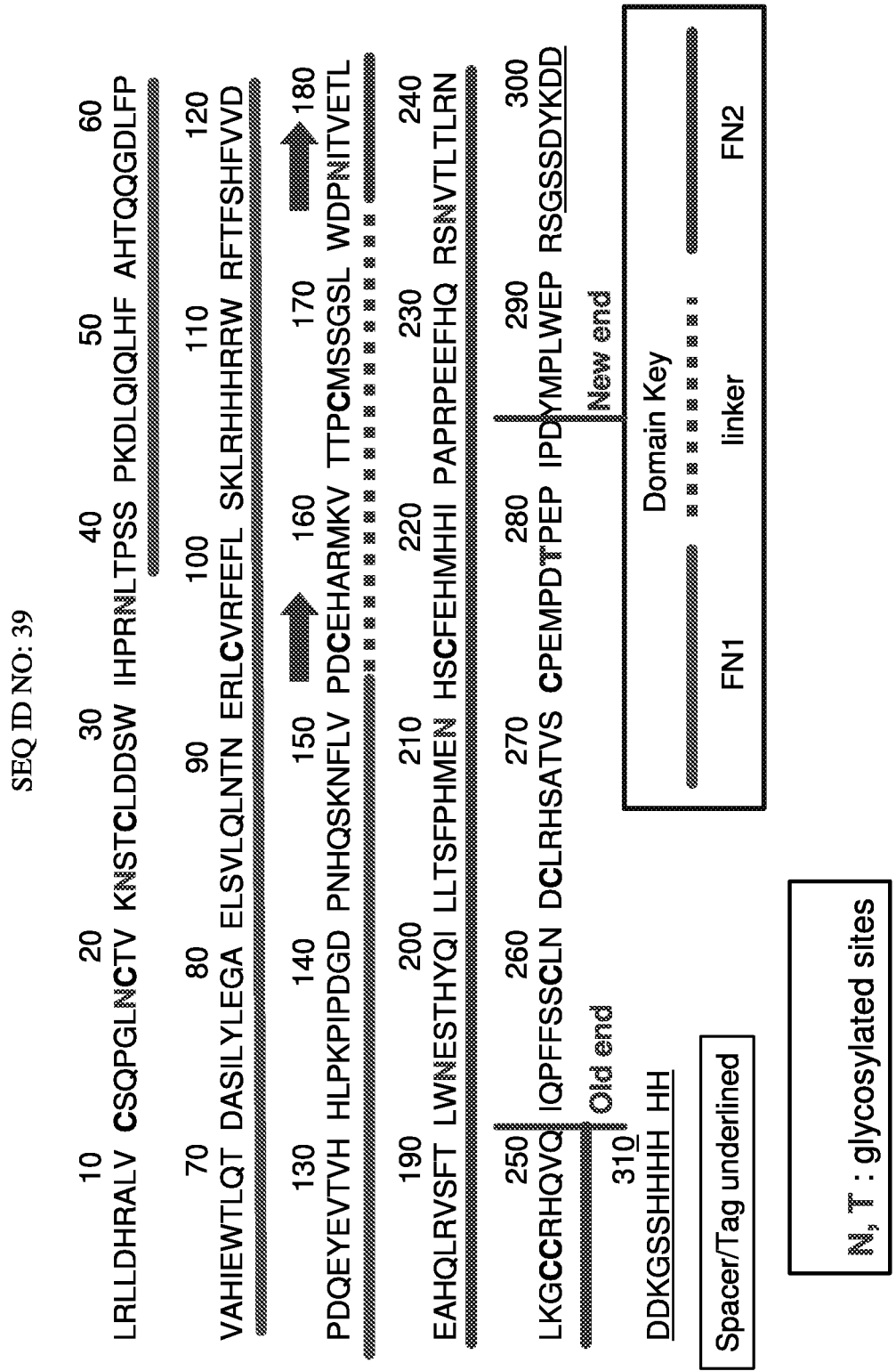

FIG. 9 is a diagram of an amino acid sequence of SEQ ID NO: 39 indicating the differences in sequence between the first and second generations of human PLAD constructs.

FIG. 10 is a diagram of an amino acid sequence of SEQ ID NO: 40 indicating the differences in sequence between the first and second generations of murine PLAD constructs. The amino acid sequence of the IgK leader (SEQ ID NOs: 16) and the C-terminal tag (SEQ ID NO: 41) are also shown.

DETAILED DESCRIPTION OF THE INVENTION

PLAD Polypeptides

The invention provides a Pre-Ligand Assembly Domain (PLAD) polypeptide comprising an amino acid sequence of a domain of an IL-17 Receptor (IL-17R) family member, a functional fragment thereof, or an amino acid sequence which is significantly identical to a domain of an IL-17 Receptor (IL-17R) family member, or a functional fragment thereof. Advantageously, the PLAD polypeptide of the invention inhibits multimerization of a receptor complex comprising an IL-17R family member.

The term "polypeptide" refers to a single chain of (naturally occurring and/or non-naturally occurring) amino acids connected by one or more peptide bonds. The PLAD polypeptide of the invention can comprise any number of amino acids and any amino acid sequence as further discussed herein.

With respect to the invention, the term "multimerization" means the formation of a protein complex (e.g., a receptor complex) comprising two or more polypeptide subunits joined together by covalent or non-covalent means. The multimerization can be the joining of two, three, four, five, six, seven, eight, or more polypeptide subunits. Accordingly, the multimerization can, for instance, be the formation of a dimer, trimer, quatromer, pentamer, hexamer, septamer, or octamer. Further, the multimerization can be the formation of a protein complex of the same polypeptide subunits. In this respect, the multimerization can, for instance, be the formation of a homodimer, homotrimer, homoquatromer, homopentamer, homohexamer, homoseptamer, or homooctamer. Alternatively, the multimerization can be the formation of a protein complex of different polypeptide subunits. In this respect, the multimerization can, for example, be the formation of a heterodimer, heterotrimer, heteroquatromer, heteropentamer, heterohexamer, heteroseptamer, or heterooctamer.

For purposes herein, the IL-17R family member can be any of the receptor subunits having the capacity to multimerize to form a receptor complex which binds to an IL-17 ligand. The IL-17 ligand can be any IL-17 ligand, including, but not limited to IL-17A, IL-17B, IL-17C, IL-17D, IL-17 E, and IL-17F, which IL-17 ligands are known in the art. See, for example, Entrez Gene Identification Nos. 53342, 27189, 112744, 27190, 64806, and 3605. In this respect, the IL-17R family member can be, for example, IL-17 Receptor A (IL-17RA), IL-17 Receptor B (IL-17RB), IL-17 Receptor C (IL-17RC), IL-17 Receptor D (IL-17RD), or IL-17 Receptor E (IL-17RE). Such IL-17R family members are known in the art. See, for example, Entrez Gene Identification Nos. 23765, 16172, 55540, 50905, 84818, 171095, 54756, 171463, 132014, and 57890. Accordingly, the receptor complex referred to herein can comprise any of IL-17RA, IL-17RB, IL-17RC, IL-17RD, IL-17RE, or any combination thereof. In one embodiment of the invention, the receptor complex comprises IL-17RA, IL-17RB, IL-17RC, or any combination thereof. The receptor complex which comprises a combination of one of the foregoing IL-17R family members can be an IL-17RA homodimer, IL-17RB homodimer, IL-17RC homodimer, IL-17RD homodimer, IL-17RE homodimer, IL-17RA/IL-17RB heterodimer, IL-17RA/IL-17RC heterodimer, IL-17RA/IL-17RD heterodimer, IL-17RA/IL-17RE heterodimer, IL-17RB/IL-17RC heterodimer, IL-17RB/IL-17RD heterodimer, IL-17RB/IL-17RE heterodimer, IL-17RC/IL-17RD heterodimer, IL-17RC/IL-17RE heterodimer, or IL-17RD/IL-17RE heterodimer.

In one embodiment, the PLAD polypeptide comprises an amino acid sequence of the C-terminal Fibronectin-III like domain (FN2) of an IL-17R family member, or an amino acid sequence which has significant sequence identity to the amino acid sequence of the FN2 of a mouse or human IL-17R. In one embodiment, the PLAD polypeptide comprises an amino acid sequence of the FN2 of the mouse or human amino acid sequence of IL-17 Receptor A (IL-17RA), or an amino acid sequence which has significant sequence identity to the FN2 of the mouse or human IL-17RA. The amino acid sequences of the mouse and human IL-17RA are known in the art as GenBank Accession Nos. NP_032385 and NP_055154, respectively, and are set forth herein as SEQ ID NOs: 1 and 2, respectively. In this respect, the PLAD polypeptide of the invention can comprise, for example, an amino acid sequence that is at least about 75% identical to the FN2 of SEQ ID NO: 1 or 2, which sequences of FN2 are set forth herein as SEQ ID NO: 3 or 4, respectively. In addition, the PLAD polypeptide of the invention can comprise, for example, an amino acid sequence that is at least about 80% identical to the FN2 of SEQ ID NO: 1 or 2, at least about 90% identical the FN2 of SEQ ID NO: 1 or 2, and/or an amino acid sequence that is at least about 95% identical to the FN2 of SEQ ID NO: 1 or 2, which sequences of FN2 are set forth herein as SEQ ID NO: 3 or 4, respectively.

As the amino acid sequences of several IL-17R family members are known in the art, it should be understood that the PLAD polypeptide of the invention does not comprise the full-length, wild-type amino acid sequence of an IL-17R family member. Rather, the PLAD polypeptide of the invention comprises only a fragment or fragment of the full-length amino acid sequence of an IL-17R family member. Accordingly, the PLAD polypeptide of the invention does not comprise the amino acid sequence of SEQ ID NO: 1 or 2.

The PLAD polypeptide of the invention can optionally further comprise an amino acid sequence of a linker region of an IL-17R. For example, the inventive PLAD polypeptide can comprise the amino acid sequence of a linker region located between the N-terminal Fibronectin-III like domain I (FN1) and FN2 of an IL-17R family member. The linker region can be, for instance, the linker region located between FN1 and FN2 of the mouse or human IL-17RA, which are set forth herein as SEQ ID NOs: 5 and 6, respectively. In this respect, the PLAD polypeptide of the invention can comprise the amino acid sequence of SEQ ID NO: 7 or 8.

Alternatively or additionally, the PLAD polypeptide of the invention can comprise a C-terminal extension, e.g., one or more amino acids added onto the C-terminus of the PLAD polypeptide, which C-terminal extension advantageously allows for the PLAD polypeptide to exist in a desired form, e.g., in a minimally aggregated state. For example, the PLAD polypeptide can comprise a C-terminal extension comprising the amino acid sequence of SEQ ID NO: 9 or 10. Accordingly, the PLAD polypeptide of the invention can comprise the amino acid sequence of any of SEQ ID NOs: 11 to 14.

Alternatively or additionally, the PLAD polypeptide of the invention can comprise an N-terminal extension, e.g., one or more amino acids added onto the N-terminus of the PLAD polypeptide, which N-terminal extension advantageously allows for the PLAD polypeptide to exist in a desired form, e.g., in a correctly folded state. For example, the PLAD polypeptide can comprise an N-terminal extension comprising the amino acid sequence of LWD (SEQ ID NO: 15). In one embodiment of the invention, the PLAD polypeptide comprises LWD (SEQ ID NO: 15) at the N-terminus, when the PLAD polypeptide comprises a proline residue immediately adjacent (C-terminal) to the sequence of SEQ ID NO: 15. In this regard, the PLAD polypeptide of the invention can comprise the amino acid sequence of any of SEQ ID NOs: 3, 4, 11, and 12.

In some embodiments of the invention, the PLAD polypeptide is a secreted polypeptide. In this respect, the PLAD polypeptide of the invention can comprise a secretion signal sequence at the N-terminus of the PLAD polypeptide. The amino acid sequences of suitable secretion signals are known in the art, and include, for example, the secretion signal sequence of any immunoglobulin, e.g., IgG, IgA, IgE, Igκ (which is set forth herein as SEQ ID NO: 16) and the secretion signal sequence of the human IL-17RA (which is set forth herein as SEQ ID NO: 17).

The PLAD polypeptide of the invention can additionally or alternatively comprise other amino acid sequences and/or other components that aid in the manufacture of the PLAD polypeptide. For example, the PLAD polypeptide can comprise an expression tag and/or a purification tag. The expression tag can be any of those known in the art and include, for example, FLAG™, Green Fluorescence Protein (GFP), Yellow Fluorescence Protein (YFP), Cyan Fluorescence Protein (CFP), MYC, and the like. The amino acid sequence of the FLAG™ tag is set forth herein as SEQ ID NO: 19. The purification tag can be, for example, the HIS tag, which comprises 6 His residues (SEQ ID NO: 20). In one embodiment of the invention, the PLAD polypeptide comprises the amino acid sequence of SEQ ID NO: 21, which is the amino acid sequence comprising two short GSS linkers, a FLAG™ tag, and a HIS tag.

In view of the foregoing, the PLAD polypeptide of the invention can comprise any of SEQ ID NOs: 3, 4, 7, 8, 11, 12, 13, 14, 31, 32, 33, 34, 35, and 36 (any of which can optionally further comprise the amino acid sequence of any one or more of SEQ ID NO: 15, 16, and 21).

PLAD-Binding Polypeptides

The invention also provides a PLAD-binding polypeptide which specifically binds to a PLAD polypeptide described herein. These PLAD-binding polypeptides may be antibodies or binding compounds that are not antibodies. In one embodiment, the PLAD-binding polypeptide specifically binds to a region of the PLAD polypeptide, which mediates the multimerization of two or more IL-17R family members. Further embodiments include PLAD-binding polypeptides that specifically bind adjacent to the PLAD polypeptide and sterically inhibit multimerization of two or more IL-17R family members. In one embodiment of the invention, the PLAD-binding polypeptide specifically binds to an epitope within the FN2 of an IL-17R, e.g., a mouse or human IL-17RA (SEQ ID NO: 3 or 4). In another embodiment of the invention, the PLAD-binding polypeptide specifically binds to an epitope within the linker region of an IL-17R, e.g., a mouse or human IL-17RA (SEQ ID NO: 5 or 6). In yet another embodiment of the invention, the PLAD-binding polypeptide specifically binds to the junction between the FN2 and linker of an IL-17R, e.g., a mouse or human IL-17RA. As used herein, the term "epitope" refers to the binding site on a PLAD polypeptide at which a PLAD-binding polypeptide binds. The PLAD-binding polypeptides can bind an IL-17R family member and inhibit IL-17 ligand binding to its receptor and/or receptor complex.

The PLAD-binding polypeptides can have any binding affinity or avidity for its epitope within the PLAD polypeptide, provided that the PLAD-binding polypeptide specifically binds to its target (e.g., PLAD polypeptide). "Specific binding" and related terms, as used herein, refers to the interaction between two or more molecules that occur in a highly selective manner, and which interaction may occur when the molecules of the interaction are present at relatively low concentrations. Specific binding excludes non-specific binding interactions, which generally occur due to a non-specific binding molecule being present at a relatively high concentration. For example, specific binding interactions include those wherein the antigen interacts with its corresponding antibody in a highly selective manner, and does not include interaction of the antigen with the multitude of other antibodies which can be evoked by other antigens. The concept of specific binding vs. non-specific binding is known in the art. See, for example, Mendel and Mendel, *Biochem. J.* 228: 269-272 (1985).

In one aspect of the invention, the PLAD-binding polypeptide has a binding affinity or avidity which is greater than that of the corresponding IL-17R family member binding to its native subunit. For aspect, in the context of a PLAD-binding polypeptide which binds to a PLAD polypeptide which inhibits the multimerization of a receptor complex comprising two IL-17RA subunits (polypeptides), the PLAD-binding polypeptide has an affinity or avidity for the PLAD polypeptide which is greater than the affinity or avidity of the native IL-17RA subunit for another IL-17RA subunit. In this regard, the PLAD-binding polypeptide can be a competitive inhibitor of the native PLAD (or native polypeptide which multimerizes with the IL-17R family member) and thereby inhibits the multimerization of a receptor complex comprising an IL-17R family member.

Antibodies

In one embodiment, the PLAD-binding polypeptide is an antibody, or an antigen-binding fragment thereof. The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. Also, the antibody can have any level of affinity or avidity for the epitope of the inventive PLAD polypeptide. In one embodiment, the antibody is specific for a part of the FN2 domain of the PLAD polypeptides described herein, such that there is minimal cross-reaction with other peptides or proteins (epitopes).

Methods of testing antibodies for the ability to bind to an epitope of the inventive PLAD polypeptide are known in the art and include any antibody-antigen binding assay, such as, for example, radioimmunoassay (RIA), ELISA, Western blot, immunoprecipitation, and competitive inhibition assays (see, e.g., Janeway et al., infra, and U.S. Patent Application Publication No. 2002/0197266 A1).

Suitable methods of making antibodies are known in the art. For instance, standard hybridoma methods are described in, e.g., Harlow and Lane (eds.), Antibodies: A Laboratory Manual, CSH Press (1988), and C A. Janeway et al. (eds.), Immunobiology, 5$^{th}$ Ed., Garland Publishing, New York, N.Y. (2001)). Alternatively, other methods, such as EBV-hybridoma methods (Haskard and Archer, J. Immunol. Methods, 74(2), 361-67 (1984), and Roder et al.$_5$ Methods EnΣymoL, 121, 140-67 (1986)), and bacteriophage vector expression systems (see, e.g., Huse et al., Science, 246, 1275-81 (1989)) are known in the art. Further, methods of producing antibodies hi non-human animals are described in, e.g., U.S. Pat. Nos. 5,545,806, 5,569,825, and 5,714,352, and U.S. Patent Application Publication No. 2002/0197266 A1).

Phage display furthermore can be used to generate the antibody of the invention. In this regard, phage libraries encoding antigen-binding variable (V) domains of antibodies can be generated using standard molecular biology and recombinant DNA techniques (see, e.g., Sambrook et al. (eds.), Molecular Cloning, A Laboratory Manual, 3$^{rd}$ Edition, Cold Spring Harbor Laboratory Press, New York (2001)). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150).

Antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Methods for generating humanized antibodies are well known in the art and are described in detail in, for example, Janeway et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in U.S. Pat. No. 5,639,641 and Pedersen et al., J. MoI. Biol, 235, 959-973 (1994).

The invention also provides antigen binding fragments of any of the antibodies described herein. The antigen binding fragment can be any fragment that has at least one antigen binding site, such as Fab, F(ab')$_2$, dsFv, sFv, diabodies, and triabodies.

A single-chain variable region fragment (sFv) antibody fragment, which consists of a truncated Fab fragment comprising the variable (V) domain of an antibody heavy chain linked to a V domain of a light antibody chain via a synthetic peptide, can be generated using routine recombinant DNA technology techniques (see, e.g., Janeway et al., supra). Similarly, disulfide-stabilized variable region fragments (dsFv) can be prepared by recombinant DNA technology (see, e.g., Reiter et al., Protein Engineering, 7, 697-704 (1994)). Antibody fragments of the invention, however, are not limited to these exemplary types of antibody fragments.

Also, the antibody, or antigen binding fragment thereof, can be modified to comprise a detectable label, such as, for instance, a radioisotope, a fluorophore (e.g., fluorescein isothiocyanate (FITC)$_5$ phycoerythrin (PE)), an enzyme (e.g., alkaline phosphatase, horseradish peroxidase), and element particles (e.g., gold particles).

The inventive antibodies and antigen binding fragments thereof are useful in detecting expression of the inventive PLAD polypeptide in which the epitope that is specifically bound by the antibody or antigen binding fragment thereof is found. Both qualitative and quantitative analyses can be performed on cells expressing the inventive PLAD polypeptide using the inventive antibodies or antigen binding fragments thereof. Such analyses include any type of immunoassay, including, for example, Western blots, immunofluorescence, immunostaining, immunoprecipitation, ELISA, radioimmunoassay, etc. Further uses of the inventive antibodies and antigen binding fragments are discussed below.

Alternative Scaffolds

Embodiments of PLAD-binding polypeptides include scaffolds having one or more domains that have the capacity to bind to PLAD proteins and act as an antagonist (or agonist). Examples of scaffold proteins that are envisioned include: fibronectin, neocarzinostatin CBM4-2, lipocalins, T-cell receptor, protein-A domain (protein Z), Im9, TPR proteins, zinc finger domains, pVIII, avian pancreatic polypeptide, GCN4, WW domain, Src homology domain 3, PDZ domains, TEM-1 Beta-lactamase, thioredoxin, staphylococcal nuclease, PHD-finger domains, CL-2, BPTI, APPI, HPSTI, ecotin, LACI-D1, LDTI, MTI-II, scorpion toxins, instect defensin-A peptide, EETI-II, Min-23, CBD, PBP, cytochrome b-562, Ldl receptor domains, gamma-crystallin, ubiquitin, transferring, and/or C-type lectin-like domains. Particular examples are described more fully below.

Further embodiments of PLAD-binding polypeptides include random peptides having the capacity to bind to PLAD and act as an antagonist (or agonist). Such peptides may be generated by any known method in the art, such as by phage display and screened for their capacity to bind PLAD, and in some embodiments, antagonize either IL-17R complex multimerization or IL-17 ligand binding. These peptides may be incorporated into various protein scaffolds as are known in the art, such as but not limited to peptibodies (see U.S. Pat. No. 7,138,370).

Avimers

Alternatively, the PLAD-binding polypeptide of the invention can be an avimer. As used herein, the term "avimer"

refers to a multimeric binding protein or peptide engineered using in vitro exon shuffling and phage display. Methods of making avimers are known in the art. See, for example, Silverman, *Nature Biotechnology* 23: 1556-1561 (2005); U.S. Patent Application Publication Nos. 2005/0053973, 2005/0089932, and 2005/0164301.

Affibodies

Alternatively, the PLAD-binding polypeptide of the invention can be an affibody. As used herein the term "affibody" refers to a scaffold protein, having a common frame of amino acids determining the overall fold or tertiary structure, but with each member characterized by a unique amino acid composition in an exposed binding surface determining binding specificity and affinity for a certain target. Affibodies represent a new class of affinity proteins based on a 58-amino acid residue protein domain, derived from one of the IgG binding domains of staphylococcal protein A, and combine small size (about 6.5 kDa) with high affinity and specificity. Suitable methods of making affibodies are known in the art. See, for example, Orlova et al., *Cancer Biother. & Radiopharm.* 22: 573-584 (2007); International Patent Application Publication No. WO 2006/092338; WO 2007/065635; and WO 2005/075507.

Chimeric Proteins

The invention further provides a chimeric protein comprising two or more of a PLAD polypeptide, a PLAD-binding polypeptide, and a heterologous polypeptide. By "protein" is meant a molecule comprising one or more polypeptide chains. The chimeric protein of the invention can comprise, for example, 1, 2, 3, 4, 5, or more polypeptide chains covalently or non-covalently joined together. For example, the chimeric protein can comprise a single polypeptide chain comprising two or more polypeptides fused together. The chimeric protein can optionally comprise one or more linkers which join the two or more polypeptides together. By "heterologous" is meant a polypeptide which is not normally or naturally found adjacent to a PLAD polypeptide or PLAD-binding polypeptide.

For example, the chimeric protein of the invention can comprise a PLAD polypeptide and a PLAD-binding polypeptide. Additionally or alternatively, the chimeric protein of the invention can comprise a heterologous polypeptide which is neither a PLAD polypeptide nor a PLAD-binding polypeptide (a non-PLAD/PLAD-binding polypeptide). For instance, the non-PLAD/PLAD-binding polypeptide can comprise an amino acid sequence encoding an immunoglobulin or a fragment thereof.

The heterologous polypeptide, e.g., the non-PLAD/PLAD-binding polypeptide, can exist as a separate polypeptide of the chimeric protein, or can exist as a polypeptide, which is expressed in frame (in tandem) with one of the inventive polypeptides described herein. The non-PLAD/PLAD-binding polypeptide can encode any peptidic or proteinaceous molecule, or a fragment thereof, including, but not limited to an immunoglobulin, or a fragment thereof, a scaffold protein, CD3, CD4, CD8, an MHC molecule, etc. For purposes herein, examples of the immunoglobulin, or fragment thereof, include a heavy chain, a light chain, a variable or constant region of a heavy or light chain, a single chain variable fragment (scFv), or an Fc, Fab, or F(ab)$_2$' fragment of an antibody, etc.

The chimeric protein can comprise one or more copies of the inventive PLAD polypeptide and/or PLAD-binding polypeptide and/or one or more copies of the heterologous polypeptide, e.g., non-PLAD/PLAD-binding polypeptide. For instance, the chimeric protein can comprise 1, 2, 3, 4, 5, or more, copies of the inventive polypeptide and/or of the heterologous polypeptide. Suitable methods of making chimeric proteins are known in the art, and include, for example, recombinant methods. See, for instance, Choi et al., *Mol. Biotechnol.* 31, 193-202 (2005).

In one embodiment of the invention, the chimeric protein has an increased half-life and/or increased solubility as compared to the PLAD polypeptide or PLAD-binding polypeptide which is part of the chimeric protein. For example, the chimeric protein can comprise an Fc region of an immunoglobulin or a fragment of a Fc region of an immunoglobulin.

Functional Variants

Included in the scope of the invention are functional variants of the inventive PLAD polypeptides, PLAD-binding polypeptides, and chimeric proteins, as well as chimeric proteins of the functional variants of the PLAD polypeptides and/or PLAD-binding polypeptides as described herein. The term "functional variant" as used herein refers to a PLAD polypeptide, PLAD-binding polypeptide, or a chimeric protein, having substantial or significant sequence identity or similarity to a parent PLAD polypeptide, parent PLAD-binding polypeptide, or parent chimeric protein, which functional variant retains the biological activity of the polypeptide of which it is a variant. Functional variants encompass, for example, those variants of the PLAD polypeptide, PLAD-binding polypeptide, or chimeric protein described herein that retain the biological function (e.g., the specific binding to a PLAD of an IL-17 receptor, e.g., IL-17RA, the specific inhibition of the multimerization of a receptor complex comprising an IL-17R family member, the specific inhibition of IL-17-mediated signaling) to a similar extent, the same extent, or to a higher extent, as the parent polypeptide (e.g., parent PLAD polypeptide, parent PLAD-binding polypeptide, or parent chimeric protein). In reference to the parent PLAD polypeptide, parent PLAD-binding polypeptide, or parent chimeric protein, the functional variant can, for instance, be at least about 30%, 50%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or more identical in amino acid sequence to the parent PLAD polypeptide, parent PLAD-binding polypeptide, or parent chimeric protein.

The functional variant can comprise any amino acid sequence provided that the amino acid sequence has significant sequence identity to the amino acid sequence of the parent polypeptide (PLAD or PLAD-binding polypeptide, chimeric protein). In one embodiment of the invention, the functional variant has an amino acid sequence that is at least about 75% identical to the amino acid sequence of the parent polypeptide. In one embodiment of the invention, the functional variant has an amino acid sequence that is at least about 80% identical to the amino acid sequence of the parent polypeptide. In one embodiment of the invention, the functional variant has an amino acid sequence that is at least about 90% identical to the amino acid sequence of the parent polypeptide.

The amino acid sequence of the functional variant can comprise, for example, the amino acid sequence of the parent polypeptide with at least one conservative amino acid substitution. Conservative amino acid substitutions are known in the art, and include amino acid substitutions in which one amino acid having certain physical and/or chemical properties is exchanged for another amino acid that has the same chemical or physical properties. For instance, the conservative ammo acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

Alternatively or additionally, the functional variants can comprise the amino acid sequence of the parent polypeptide with at least one non-conservative amino acid substitution. In this case, it is preferable for the non-conservative amino acid substitution to not interfere with or inhibit the biological activity of the functional variant. In one aspect of the invention, the non-conservative amino acid substitution enhances the biological activity of the functional variant, such that the biological activity of the functional variant is increased as compared to the parent polypeptide.

The amino acid substitution(s) can be within any region of the amino acid sequence of the parent polypeptide or protein. For example, the amino acid substitution(s) can be located within the region of the amino acid sequence which encodes the FN1 of the parent polypeptide. It is understood that the amino acid substitution(s) do not significantly decrease the biological function of the functional variant.

Functional Fragments

Included in the scope of the invention is a functional fragment of an inventive PLAD polypeptide, inventive PLAD-binding polypeptide, or inventive chimeric protein. The functional fragment can comprise any fragment comprising contiguous amino acids of the inventive PLAD polypeptide, inventive PLAD-binding polypeptide, or inventive chimeric protein of which it is a part, provided that the functional fragment retains at least some of the biological function of the parent polypeptide (PLAD or PLAD binding) or parent chimeric protein. The term "functional fragment" when used in reference to a polypeptide or protein refers to any part or fragment of the polypeptide or protein of the invention, which part or fragment retains the biological activity of the polypeptide or protein of which it is a part (the parent polypeptide). Functional fragments encompass, for example, those parts of a polypeptide or protein that retain the ability to, e.g., specifically bind to a PLAD of an IL-17 receptor, specifically inhibit IL-17-mediated signaling, specifically inhibit multimerization of a receptor complex comprising an IL-17 receptor, e.g., IL-17A, to a similar extent, the same extent, or to a higher extent, as the parent polypeptide or protein. In reference to the parent polypeptide or protein, the functional fragment can comprise, for instance, about 10%, 25%, 30%, 50%, 68%, 80%, 90%, 95%, or more, of the parent polypeptide.

The functional fragment can comprise additional amino acids at the amino or carboxy terminus of the fragment, or at both termini, which additional amino acids are not found in the amino acid sequence of the parent polypeptide or parent protein. In one embodiment, the additional amino acids do not interfere with the biological function of the functional fragment. In one embodiment, the additional amino acids enhance the biological activity, as compared to the biological activity of the parent polypeptide or parent protein.

The polypeptides (PLAD or PLAD-binding) or proteins of the invention (including functional fragments and functional variants), can be of any length, i.e., can comprise any number of amino acids, provided that the polypeptides or proteins, (or functional fragments or functional variants thereof) retain their biological activity. For example, the polypeptide or protein can be about 50 to about 5000 amino acids long, such as 50, 70, 75, 100, 125, 150, 175, 200, 300, 400, 500, 600, 700, 800, 900, 1000 or more amino acids in length. In this regard, the polypeptides of the invention also include oligopeptides.

Modified Polypeptides

The polypeptides (PLAD and PLAD-binding) and chimeric proteins of the invention (including functional fragments and functional variants) can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylammomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The polypeptides (PLAD or PLAD-binding) and proteins of the invention (including functional fragments and functional variants) can be glycosylated, amidated, carboxylated, phosphorylated, esterified, N-acylated, cyclized via, e.g., a disulfide bridge, or converted into an acid addition salt, and/or optionally dimerized or polymerized, conjugated, or labeled (e.g., labeled with a detectable label, such as any of those described herein).

When the polypeptides (PLAD or PLAD-binding) or proteins of the invention (including functional fragments and functional variants) are in the form of a salt, and, in one embodiment of the invention, the polypeptides or proteins are in the form of a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids.

Making Polypeptides

The polypeptides and proteins of the invention (including functional fragments and functional variants thereof) can be obtained by methods known in the art. Suitable methods of de novo synthesizing polypeptides and proteins are described in, for example, Chan et al., *Fmoc Solid Phase Peptide Synthesis*, Oxford University Press, Oxford, United Kingdom, 2005; *Peptide and Protein Drug Analysis*, ed. Reid, R., Marcel Dekker, Inc., 2000; *Epitope Mapping*, ed. Westwood et al., Oxford University Press, Oxford, United Kingdom, 2000; and U.S. Pat. No. 5,449,752.

Also, the inventive polypeptides and proteins can be recombinantly produced using the nucleic acids described herein using standard recombinant methods. See, for instance, Sambrook et al., *Molecular Cloning: A Laboratory Manual*, $3^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, NY, 1994.

Further, some of the polypeptides and proteins of the invention (including functional fragments and functional variants thereof) can be isolated and/or purified, in part, from a source, such as a plant, a bacterium, an insect, a mammal, e.g., a rat, a human, etc. Methods of isolation and purification are well-known in the art.

Alternatively, the polypeptides and proteins described herein (including functional fragments and functional variants thereof) can be commercially synthesized by companies, such as Synpep (Dublin, Calif.), Peptide Technologies Corp. (Gaithersburg, Md.), and Multiple Peptide Systems (San Diego, Calif.). In this respect, the inventive polypeptides or proteins can be synthetic, recombinant, isolated, and/or purified.

Transitional Language

The polypeptides or proteins of the invention can consist essentially of the specified amino acid sequence described herein, such that other components of the polypeptide or protein, e.g., other amino acids, do not materially change the biological activity of the polypeptide or protein. In this regard, the inventive polypeptide or protein can, for example, consist essentially of an amino acid sequence selected from the group consisting of SEQ ID NOs: 3, 4, 7, 8, 11, 12, 13, 14, 31, 32, 33, 34, 35, and 36 (any of which can optionally further comprise the amino acid sequence of any one or more of SEQ ID NO: 15, 16, and 21).

Alternatively, the polypeptide can consist of the specified amino acid sequence or sequences described herein. In this regard, the invention provides a polypeptide consisting of an amino acid sequence selected from the group consisting of SEQ ID NOs: 3, 4, 7, 8, 11, 12, 13, 14, 31, 32, 33, 34, 35, and 36 (any of which can optionally further comprise the amino acid sequence of any one or more of SEQ ID NO: 15, 16, and 21).

Nucleic Acids

Further provided by the invention is a nucleic acid comprising a nucleotide sequence encoding any of the PLAD polypeptides, PLAD-binding polypeptides, and chimeric proteins described herein (including functional fragments and functional variants thereof). By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered inter-nucleotide linkage, such as a phosphoroamidate linkage or a phosphorothioate linkage, instead of the phosphodiester found between the nucleotides of an unmodified oligonucleotide. In one embodiment, the nucleic acid does not comprise any insertions, deletions, inversions, and/or substitutions. However, it may be suitable in some instances, as discussed herein, for the nucleic acid to comprise one or more insertions, deletions, inversions, and/or substitutions.

In one embodiment of the invention, the nucleic acid comprises, consists essentially of, or consists of a nucleotide sequence that encodes a polypeptide having the amino acid sequence of any of SEQ ID NOs: 3, 4, 7, 8, 11, 12, 13, 14, 31, 32, 33, 34, 35, and 36 (any of which can optionally further comprise the amino acid sequence of any one or more of SEQ ID NO: 15, 16, and 21). The nucleotide sequence alternatively can comprise, consist essentially of, or consist of a nucleotide sequence which is degenerate to any of SEQ ID NOs: 3, 4, 7, 8, 11, 12, 13, 14, 31, 32, 33, 34, 35, and 36 (any of which can optionally further comprise the amino acid sequence of any one or more of SEQ ID NO: 15, 16, and 21).

In one aspect of the invention, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids of the invention can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridme, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, N-substituted adenine, 7-methylguanine, 5-methylammomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouratil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The nucleic acids of the invention includes a nucleic acid comprising a nucleotide sequence which hybridizes under moderately or highly stringent conditions as defined herein with the fully complementary sequence of a nucleotide sequence encoding a polypeptide having the amino acid sequence of any of SEQ ID NOs: 3, 4, 7, 8, 11, 12, 13, 14, 31, 32, 33, 34, 35, and 36 (any of which can optionally further comprise the amino acid sequence of any one or more of SEQ ID NO: 15, 16, and 21), or a functional fragment or functional variant thereof.

The term "highly stringent conditions" refers to those conditions that are designed to permit hybridization of DNA strands whose sequences are highly complementary, and to exclude hybridization of significantly mismatched DNAs. Hybridization stringency is principally determined by temperature, ionic strength, and the concentration of denaturing agents such as formamide. Examples of "highly stringent conditions" for hybridization and washing are 0.015M sodium chloride, 0.0015M sodium citrate at 65-68° C. or 0.015M sodium chloride, 0.0015M sodium citrate, and 50% formamide at 42° C. See Sambrook, Fritsch & Maniatis, Molecular Cloning: A Laboratory Manual, $2^{nd}$ Ed., Cold Spring Harbor Laboratory, (Cold Spring Harbor, N.Y. 1989); Anderson et al., Nucleic Acid Hybridisation: a practical approach, Ch. 4, IRL Press Limited (Oxford, England).

More stringent conditions (such as higher temperature, lower ionic strength, higher formamide, or other denaturing agent) may also be used, however, the rate of hybridization will be affected. Other agents may be included in the hybridization and washing buffers for the purpose of reducing nonspecific and/or background hybridization. Examples are 0.1% bovine serum albumin, 0.1% polyvinyl-pyrrolidone, 0.1% sodium pyrophosphate, 0.1% sodium dodecylsulfate (NaDodSO4 or SDS), ficoll, Denhardt's solution, sonicated salmon sperm DNA (or other non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4, however, at typical ionic strength conditions, the rate of hybridization is nearly independent of pH. See Anderson et al., Nucleic Acid Hybridisation: a Practical Approach, Ch. 4, IRL Press Limited (Oxford, England).

Factors affecting the stability of a DNA duplex include base composition, length, and degree of base pair mismatch. Hybridization conditions can be adjusted by one skilled in the art in order to accommodate these variables and allow DNAs of different sequence relatedness to form hybrids. The melting temperature of a perfectly matched DNA duplex can be estimated by the following equation:

$$T_m (°C.) = 81.5 + 16.6(\log [Na+]) + 0.41(\%G+C) - 600/N - 0.72(\%\text{formamide})$$

where N is the length of the duplex formed, [Na+] is the molar concentration of the sodium ion in the hybridization or washing solution, % G+C is the percentage of (guanine+cytosine) bases in the hybrid. For imperfectly matched hybrids, the melting temperature is reduced by approximately 1° C. for each 1% mismatch.

The term "moderately stringent conditions" refers to conditions under which a DNA duplex with a greater degree of base pair mismatching than could occur under "highly stringent conditions" is able to form. Examples of typical "moderately stringent conditions" are 0.015M sodium chloride, 0.0015M sodium citrate at 50-65° C. or 0.015M sodium chloride, 0.0015M sodium citrate, and 20% formamide at 37-50° C. By way of example, a "moderately stringent" condition of 50° C. in 0.015 M sodium ion will allow about a 21% mismatch.

It will be appreciated by those skilled in the art that there is no absolute distinction between "highly" and "moderately" stringent conditions. For example, at 0.015M sodium ion (no formamide), the melting temperature of perfectly matched long DNA is about 71° C. With a wash at 65° C. (at the same ionic strength), this would allow for approximately a 6% mismatch. To capture more distantly related sequences, one skilled in the art can simply lower the temperature or raise the ionic strength.

A good estimate of the melting temperature in 1M NaCl* for oligonucleotide probes up to about 20 nt is given by:

$$Tm = 2° C. \text{ per A-T base pair} + 4° C. \text{ per G-C base pair}$$

*The sodium ion concentration in 6× salt sodium citrate (SSC) is 1M. See Suggs et al., Developmental Biology Using Purified Genes, p. 683, Brown and Fox (eds.) (1981).

High stringency washing conditions for oligonucleotides are usually at a temperature of 0-5° C. below the Tm of the oligonucleotide in 6×SSC, 0.1% SDS.

Primers

Also provided by the invention is a primer nucleic acid comprising a nucleotide sequence which is complementary or hybridizes under stringent conditions to a fragment of the nucleotide sequence encoding any of the PLAD polypeptides, PLAD-binding polypeptides, and chimeric proteins described herein (including functional fragments and functional variants thereof). The inventive primer nucleic acid can be modified to comprise a detectable label, such as, for instance, a radioisotope, a fluorophore, and an element particle. The inventive primer nucleic acid is useful in detecting the nucleic acid which encodes the polypeptide or protein. Both qualitative and quantitative analyses can be performed on cells comprising the inventive nucleic acid which encodes the polypeptide. Such analyses include, for example, any type of PCR-based assay or hybridization assay, e.g., Southern blot, Northern blot.

Vectors

The nucleic acids of the invention can be incorporated into a vector. In this regard, the invention provides a vector comprising any of the nucleic acids of the invention. For purposes herein, the term "vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive vectors can comprise any type of nucleotides, including, but not limited to DNA and RNA, which can be single-stranded or double-stranded, synthesized or obtained in part from natural sources, and which can contain natural, non-natural or altered nucleotides. The vectors can comprise naturally-occurring or non-naturally-occurring internucleotide linkages, or both types of linkages. In one aspect, the altered nucleotides or non-naturally occurring internucleotide linkages do not hinder the transcription or replication of the vector.

The vector of the invention can be any suitable recombinant expression vector, and can be used to transform or transfect any suitable host. Suitable vectors include those designed for propagation and expansion or for expression or both, such as plasmids and viruses. The vector can be selected from the group consisting of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT1 1, λZapII (Stratagene), λEMBL4, and λNM1 149, also can be used. Examples of plant expression vectors include pBIO1, pBI101.2, pBI101.3, pBI121 and pBIN19 (Clontech). Examples of animal expression vectors include pEUK-C1, pMAM and pMAMneo (Clontech). In one aspect, the recombinant expression vector is a viral vector, e.g., a retroviral vector.

The vectors of the invention can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColE1, 2μ plasmid, λ, SV40, bovine papilloma virus, and the like.

In one aspect, the inventive vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based.

The vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The vector can comprise a native or non-native promoter operably linked to the nucleotide sequence encoding the PLAD polypeptide, PLAD-binding polypeptide, or chimeric protein (including functional fragments and functional variants thereof), or to the nucleotide sequence which is complementary to or which hybridizes to the nucleotide sequence encoding the polypeptide. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

The inventive vectors can be designed for either transient expression, for stable expression, or for both. Also, the vectors can be made for constitutive expression or for inducible expression. Further, the vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, *Suicide Gene Therapy: Methods and Reviews*, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

Host Cells

The invention further provides a host cell comprising any of the vectors described herein. As used herein, the term "host cell" refers to any type of cell that can contain the inventive vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α *E. coli* cells, Chinese hamster ovarian cells, monkey VERO cells, COS cells, HEK293 cells, and the like. For purposes of amplifying or replicating the vector, the host cell is, in one aspect, a prokaryotic cell, e.g., a DH5α cell. For purposes of producing a recombinant polypeptide the host cell is, in one aspect, a mammalian cell. In one aspect, the host cell is a human cell. The host cell can be of any cell type, can originate from any type of tissue, and can be of any developmental stage.

Also provided by the invention is a population of cells comprising at least one host cell described herein. The population of cells can be a heterogeneous population comprising the host cell comprising any of the vectors described, in addition to at least one other cell, e.g., a host cell (e.g., a T cell), which does not comprise any of the vectors, or a cell other than a T cell, e.g., a B cell, a macrophage, a neutrophil, an erythrocyte, a hepatocyte, an endothelial cell, an epithelial cells, a muscle cell, a brain cell, etc. Alternatively, the population of cells can be a substantially homogeneous population, in which the population comprises mainly of host cells (e.g., consisting essentially of) comprising the vector. The population also can be a clonal population of cells, in which all cells of the population are clones of a single host cell comprising a vector, such that all cells of the population comprise the vector. In one embodiment of the invention, the population of cells is a clonal population comprising host cells comprising a vector as described herein.

Isolated or Purified

The inventive PLAD polypeptides, PLAD-binding polypeptides, chimeric proteins (including functional fragments and functional variants thereof), nucleic acids, vectors, host cells (including populations thereof), can be isolated and/or purified. The term "isolated" as used herein means having been removed from its natural environment and includes varying ranges of purity. The term "purified" as used herein means having been increased in purity, wherein "purity" is a relative term, and not to be necessarily construed as absolute purity. For example, the purity can be at least about 50%, can be greater than 60%, 70%, 75, 80%, 85%, 90%, 91%, 92%, 93%, 94%, 95%, 96%, 97%, 98%, 99%, or can be nearly 100%.

Conjugates

Included in the scope of the invention are conjugates, e.g., bioconjugates, comprising any of the inventive PLAD or PLAD-binding polypeptides and chimeric proteins (including any of the functional fragments or variants thereof), nucleic acids, vectors, host cells, or populations of host cells described herein. Conjugates, as well as methods of synthesizing conjugates in general, are known in the art (See, for instance, Hudecz, F., *Methods Mol. Biol*, 298: 209-223 (2005) and Kirin et al., *Inorg Chem.*, 44(15): 5405-5415 (2005)).

The conjugate of the invention comprises a second component which can be any component provided that it does not interfere with the function of the inventive PLAD or PLAD-binding polypeptides and chimeric proteins (including any of the functional fragments or variants thereof), nucleic acids, vectors, host cells, or populations of host cells described herein. The second component can be directly or indirectly linked or conjugated to the PLAD or PLAD-binding polypeptides and chimeric proteins (including any of the functional fragments or variants thereof), nucleic acids, vectors, host cells, or populations of host cells described herein. In this regard, the conjugate of the invention can comprise a linker which links or bridges the PLAD or PLAD-binding polypeptides and chimeric proteins (including any of the functional fragments or variants thereof), nucleic acids, vectors, host cells, or populations of host cells described herein to the second component.

In one embodiment of the invention, the conjugate comprises a polymer. The polymer can comprise one or more of the following polymers: polyamides, polycarbonates, polyalkylenes and derivatives thereof including, polyalkylene glycols, polyalkylene oxides, polyalkylene terepthalates, polymers of acrylic and methacrylic esters, including poly (methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate), polyvinyl polymers including polyvinyl alcohols, polyvinyl ethers, polyvinyl esters, polyvinyl halides, poly(vinyl acetate), and polyvinylpyrrolidone, polyglycolides, polysiloxanes, polyurethanes and co-polymers thereof, celluloses including alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt, polypropylene, polyethylenes including poly (ethylene glycol), poly(ethylene oxide), and poly(ethylene terephthalate), and polystyrene.

The polymer can be a biodegradable polymer, including a synthetic biodegradable polymer (e.g., polymers of lactic acid and glycolic acid, polyanhydrides, poly(ortho)esters, polyurethanes, poly(butic acid), poly(valeric acid), and poly (lactide-cocaprolactone)), and a natural biodegradable polymer (e.g., alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins (e.g., zein and other prolamines and hydrophobic proteins)), as well as any copolymer or mixture thereof. In general, these materials degrade either by enzymatic hydrolysis or exposure to water in vivo, by surface or bulk erosion.

The polymer can be a bioadhesive polymer, such as a bioerodible hydrogel described by H. S. Sawhney, C. P. Pathak and J. A. Hubbell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly (isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

In one embodiment, the polymer is a water-soluble polymer. Suitable water-soluble polymers are known in the art and include, for example, polyvinylpyrrolidone, hydroxypropyl cellulose (HPC; Klucel), hydroxypropyl methylcellulose (HPMC; Methocel), nitrocellulose, hydroxypropyl ethylcellulose, hydroxypropyl butylcellulose, hydroxypropyl pentylcellulose, methyl cellulose, ethylcellulose (Ethocel), hydroxyethyl cellulose, various alkyl celluloses and hydroxyalkyl celluloses, various cellulose ethers, cellulose acetate, carboxymethyl cellulose, sodium carboxymethyl cellulose, calcium carboxymethyl cellulose, vinyl acetate/crotonic acid copolymers, poly-hydroxyalkyl methacrylate, hydroxymethyl methacrylate, methacrylic acid copolymers, polymethacrylic acid, polymethylmethacrylate, maleic anhydride/methyl vinyl ether copolymers, poly vinyl alcohol, sodium and calcium polyacrylic acid, polyacrylic acid, acidic carboxy polymers, carboxypolymethylene, carboxyvinyl polymers, polyoxyethylene polyoxypropylene copolymer, polymethylvinylether co-maleic anhydride, carboxymethylamide, potassium methacrylate divinylbenzene co-polymer, polyoxyethyleneglycols, polyethylene oxide, and derivatives, salts, and combinations thereof.

In one embodiment, the water-soluble polymer is a polyethylene glycol (PEG). The PEG can be any of those known in the art, and can be of any molecular weight.

Pharmaceutical Compositions

The inventive PLAD polypeptides, PLAD-binding polypeptides, chimeric proteins, (including functional fragments and variants of any of the foregoing), nucleic acids, vectors, host cells (including populations thereof), and conjugates, all of which are collectively referred to as "inventive PLAD materials" hereinafter, can be formulated into a composition, such as a pharmaceutical composition. In this regard, the invention provides a pharmaceutical composition comprising any of the PLAD polypeptides, PLAD-binding polypeptides, chimeric proteins, functional fragments, functional variants, nucleic acids, vectors, host cells (including populations thereof), and/or conjugates, and a pharmaceutically acceptable carrier. The inventive pharmaceutical compositions containing any of the inventive PLAD materials can comprise more than one inventive PLAD material, e.g., a PLAD polypeptide and a PLAD polypeptide-encoding nucleic acid, or two or more different PLAD polypeptides. Alternatively, the pharmaceutical composition can comprise an inventive PLAD material in combination with another pharmaceutically active agent or drug, as further described herein.

Combination Formulations

For example, the pharmaceutical composition described herein can comprise an inventive PLAD material in combination (pre-treatment, post-treatment, or concurrent treatment) with any of one or more TNF inhibitors for the treatment or prevention of the diseases and disorders recited herein, such as but not limited to, all forms of soluble TNF receptors including Etanercept (such as ENBREL®), as well as all forms of monomeric or multimeric p75 and/or p55 TNF receptor molecules and fragments thereof; anti-human TNF antibodies, such as but not limited to, Infliximab (such as REMICADE®), and D2E7 (such as HUMIRA®), and the like. Such TNF inhibitors include compounds and proteins which block in vivo synthesis or extracellular release of TNF.

In a specific embodiment, the pharmaceutical composition described herein can comprise an inventive PLAD material in combination (pre-treatment, post-treatment, or concurrent treatment) with any of one or more of the following TNF inhibitors: TNF binding proteins (soluble TNF receptor type-I and soluble TNF receptor type-II ("sTNFRs"), as defined herein), anti-TNF antibodies, granulocyte colony stimulating factor; thalidomide; BN 50730; tenidap; E 5531; tiapafant PCA 4248; nimesulide; panavir; rolipram; RP 73401; peptide T; MDL 201,449A; (1R,3S)-Cis-1-[9-(2,6-diaminopurinyl)]-3-hydroxy-4-cyclopentene hydrochloride; (1R,3R)-trans-1-(9-(2,6-diamino)purine]-3-acetoxycyclopentane; (1R,3R)-trans-1-[9-adenyl)-3-azidocyclopentane hydrochloride and (1R,3R)-trans-1-(6-hydroxy-purin-9-yl)-3-azidocyclo-pentane. TNF binding proteins are disclosed in the art (EP 308 378, EP 422 339, GB 2 218 101, EP 393 438, WO 90/13575, EP 398 327, EP 412 486, WO 91/03553, EP 418 014, JP 127,800/1991, EP 433 900, U.S. Pat. No. 5,136, 021, GB 2 246 569, EP 464 533, WO 92/01002, WO 92/13095, WO 92/16221, EP 512 528, EP 526 905, WO 93/07863, EP 568 928, WO 93/21946, WO 93/19777, EP 417 563, WO 94/06476, and PCT International Application No. PCT/US97/12244).

For example, EP 393 438 and EP 422 339 teach the amino acid and nucleic acid sequences of a soluble TNF receptor type I (also known as "sTNFR-I" or "30 kDa TNF inhibitor") and a soluble TNF receptor type II (also known as "sTNFR-II" or "40 kDa TNF inhibitor"), collectively termed "sTNFRs", as well as modified forms thereof (e.g., fragments, functional derivatives and variants). EP 393 438 and EP 422 339 also disclose methods for isolating the genes responsible for coding the inhibitors, cloning the gene in suitable vectors and cell types and expressing the gene to produce the inhibitors. Additionally, polyvalent forms (i.e., molecules comprising more than one active moiety) of sTNFR-I and sTNFR-II have also been disclosed. In one embodiment, the polyvalent form may be constructed by chemically coupling at least one TNF inhibitor and another moiety with any clinically acceptable linker, for example polyethylene glycol (WO 92/16221 and WO 95/34326), by a peptide linker (Neve et al. (1996), Cytokine, 8(5):365-370, by chemically coupling to biotin and then binding to avidin (WO 91/03553) and, finally, by combining chimeric antibody molecules (U.S. Pat. No. 5,116, 964, WO 89/09622, WO 91/16437 and EP 315062.

Anti-TNF antibodies include the MAK 195F Fab antibody (Holler et al. (1993), 1st International Symposium on Cytokines in Bone Marrow Transplantation, 147); CDP 571 anti-TNF monoclonal antibody (Rankin et al. (1995), *British Journal of Rheumatology*, 34:334-342); BAY X 1351 murine anti-tumor necrosis factor monoclonal antibody (Kieft et al. (1995), 7th European Congress of Clinical Microbiology and Infectious Diseases, page 9); CenTNF cA2 anti-TNF monoclonal antibody (Elliott et al. (1994), *Lancet*, 344:1125-1127 and Elliott et al. (1994), *Lancet*, 344:1105-1110).

The pharmaceutical composition described herein can comprise an inventive PLAD material in combination with all forms of IL-1 inhibitors, such as but not limited to, kineret (for example ANAKINRA®). Interleukin-1 receptor antagonist (IL-1ra) is a human protein that acts as a natural inhibitor of interleukin-1. Interleukin-1 receptor antagonists, as well as the methods of making and methods of using thereof, are described in U.S. Pat. No. 5,075,222; WO 91/08285; WO 91/17184; AU 9173636; WO 92/16221; WO 93/21946; WO 94/06457; WO 94/21275; FR 2706772; WO 94/21235; DE 4219626; WO 94/20517; WO 96/22793 and WO 97/28828. The proteins include glycosylated as well as non-glycosylated IL-1 receptor antagonists. Specifically, three forms of IL-1ra (IL-1raα, IL-1raβ and IL-1rax), each being encoded by the same DNA coding sequence and variants thereof, are disclosed and described in U.S. Pat. No. 5,075,222. Methods for producing IL-1 inhibitors, particularly IL-1ras, are also disclosed in the U.S. Pat. No. 5,075,222. An additional class of interleukin-1 inhibitors includes compounds capable of specifically preventing activation of cellular receptors to IL-1. Such compounds include IL-1 binding proteins, such as soluble receptors and monoclonal antibodies. Such compounds also include monoclonal antibodies to the receptors. A further class of interleukin-1 inhibitors includes compounds and proteins that block in vivo synthesis and/or extracellular release of IL-1. Such compounds include agents that affect transcription of IL-1 genes or processing of IL-1 pre-proteins.

The pharmaceutical composition described herein can comprise an inventive PLAD material in combination with all forms of CD28 inhibitors, such as but not limited to, abatacept (for example ORENCIA®).

The pharmaceutical composition described herein can comprise an inventive PLAD material in combination with all forms of IL-6 and/or IL-6 receptor inhibitors, such as but not limited to, abatacept (for example ACTEMRA®).

The pharmaceutical composition described herein can comprise an inventive PLAD material in combination with one or more cytokines, lymphokines, hematopoietic factor(s), and/or an anti-inflammatory agent.

Treatment of the diseases and disorders recited herein can include the use of first line drugs for control of pain and inflammation in combination (pretreatment, post-treatment, or concurrent treatment) with treatment with one or more of the inventive PLAD materials provided herein. These drugs are classified as non-steroidal, anti-inflammatory drugs (NSAIDs). Secondary treatments include corticosteroids, slow acting antirheumatic drugs (SAARDs), or disease modifying (DM) drugs. Information regarding the following compounds can be found in The Merck Manual of Diagnosis and Therapy, Sixteenth Edition, Merck, Sharp & Dohme Research Laboratories, Merck & Co., Rahway, N.J. (1992) and in Pharmaprojects, PJB Publications Ltd.

In a specific embodiment, the pharmaceutical composition described herein can comprise an inventive PLAD material in combination with any of one or more NSAIDs for the treatment of the diseases and disorders recited herein. NSAIDs owe their anti-inflammatory action, at least in part, to the inhibition of prostaglandin synthesis (Goodman and Gilman in "The Pharmacological Basis of Therapeutics," MacMillan 7th Edition (1985)). NSAIDs can be characterized into at least nine groups: (1) salicylic acid derivatives; (2) propionic acid derivatives; (3) acetic acid derivatives; (4) fenamic acid derivatives; (5) carboxylic acid derivatives; (6) butyric acid derivatives; (7) oxicams; (8) pyrazoles and (9) pyrazolones.

In another specific embodiment, the pharmaceutical composition described herein can comprise an inventive PLAD material in combination (pretreatment, post-treatment, or concurrent treatment) with any of one or more salicylic acid derivatives, prodrug esters or pharmaceutically acceptable salts thereof. Such salicylic acid derivatives, prodrug esters and pharmaceutically acceptable salts thereof comprise: acetaminosalol, aloxiprin, aspirin, benorylate, bromosaligenin, calcium acetylsalicylate, choline magnesium trisalicylate, magnesium salicylate, choline salicylate, diflusinal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide O-acetic acid, salsalate, sodium salicylate and sulfasalazine. Structurally related salicylic acid derivatives having similar analgesic and anti-inflammatory properties are also intended to be encompassed by this group.

In an additional specific embodiment, the pharmaceutical composition described herein can comprise an inventive PLAD material in combination (pretreatment, post-treatment, or concurrent treatment) with any of one or more propionic acid derivatives, prodrug esters or pharmaceutically acceptable salts thereof. The propionic acid derivatives, prodrug esters, and pharmaceutically acceptable salts thereof comprise: alminoprofen, benoxaprofen, bucloxic acid, carprofen, dexindoprofen, fenoprofen, flunoxaprofen, fluprofen, flurbiprofen, furcloprofen, ibuprofen, ibuprofen aluminum, ibuproxam, indoprofen, isoprofen, ketoprofen, loxoprofen, miroprofen, naproxen, naproxen sodium, oxaprozin, piketoprofen, pimeprofen, pirprofen, pranoprofen, protizinic acid, pyridoxiprofen, suprofen, tiaprofenic acid and tioxaprofen. Structurally related propionic acid derivatives having similar analgesic and anti-inflammatory properties are also intended to be encompassed by this group.

In yet another specific embodiment, the pharmaceutical composition described herein can comprise an inventive PLAD material in combination (pretreatment, post-treatment, or concurrent treatment) with any of one or more acetic acid derivatives, prodrug esters or pharmaceutically acceptable salts thereof. The acetic acid derivatives, prodrug esters, and pharmaceutically acceptable salts thereof comprise: acemetacin, alclofenac, amfenac, bufexamac, cinmetacin, clopirac, delmetacin, diclofenac potassium, diclofenac sodium, etodolac, felbinac, fenclofenac, fenclorac, fenclozic acid, fentiazac, furofenac, glucametacin, ibufenac, indomethacin, isofezolac, isoxepac, lonazolac, metiazinic acid, oxametacin, oxpinac, pimetacin, proglumetacin, sulindac, talmetacin, tiaramide, tiopinac, tolmetin, tolmetin sodium, zidometacin and zomepirac. Structurally related acetic acid derivatives having similar analgesic and anti-inflammatory properties are also intended to be encompassed by this group.

In another specific embodiment, the pharmaceutical composition described herein can comprise an inventive PLAD material in combination (pretreatment, post-treatment, or concurrent treatment) with any of one or more fenamic acid derivatives, prodrug esters or pharmaceutically acceptable salts thereof. The fenamic acid derivatives, prodrug esters and pharmaceutically acceptable salts thereof comprise: enfenamic acid, etofenamate, flufenamic acid, isonixin, meclofenamic acid, meclofenamate sodium, medofenamic acid, mefenamic acid, niflumic acid, talniflumate, terofenamate, tolfenamic acid and ufenamate. Structurally related fenamic acid derivatives having similar analgesic and anti-inflammatory properties are also intended to be encompassed by this group.

In an additional specific embodiment, the pharmaceutical composition described herein can comprise an inventive PLAD material in combination (pretreatment, post-treatment, or concurrent treatment) with any of one or more carboxylic acid derivatives, prodrug esters or pharmaceutically acceptable salts thereof. The carboxylic acid derivatives, prodrug esters, and pharmaceutically acceptable salts thereof which can be used comprise: clidanac, diflunisal, flufenisal, inoridine, ketorolac and tinoridine. Structurally related carboxylic acid derivatives having similar analgesic and anti-inflammatory properties are also intended to be encompassed by this group.

In yet another specific embodiment, the pharmaceutical composition described herein can comprise an inventive PLAD material in combination (pretreatment, post-treatment, or concurrent treatment) with any of one or more butyric acid derivatives, prodrug esters or pharmaceutically acceptable salts thereof. The butyric acid derivatives, prodrug esters, and pharmaceutically acceptable salts thereof comprise: bumadizon, butibufen, fenbufen and xenbucin. Structurally related butyric acid derivatives having similar analgesic and anti-inflammatory properties are also intended to be encompassed by this group.

In another specific embodiment, the pharmaceutical composition described herein can comprise an inventive PLAD material in combination (pretreatment, post-treatment, or concurrent treatment) with any of one or more oxicams, prodrug esters, or pharmaceutically acceptable salts thereof. The oxicams, prodrug esters, and pharmaceutically acceptable salts thereof comprise: droxicam, enolicam, isoxicam, piroxicam, sudoxicam, tenoxicam and 4-hydroxyl-1,2-benzothiazine 1,1-dioxide 4-(N-phenyl)-carboxamide. Structurally related oxicams having similar analgesic and anti-inflammatory properties are also intended to be encompassed by this group.

In still another specific embodiment, the pharmaceutical composition described herein can comprise an inventive PLAD material in combination (pretreatment, post-treatment, or concurrent treatment) with any of one or more pyrazoles, prodrug esters, or pharmaceutically acceptable salts thereof. The pyrazoles, prodrug esters, and pharmaceutically acceptable salts thereof which may be used comprise: difenamizole and epirizole. Structurally related pyrazoles having similar analgesic and anti-inflammatory properties are also intended to be encompassed by this group.

In an additional specific embodiment, the pharmaceutical composition described herein can comprise an inventive PLAD material in combination (pretreatment, post-treatment or, concurrent treatment) with any of one or more pyrazolones, prodrug esters, or pharmaceutically acceptable salts thereof. The pyrazolones, prodrug esters and pharmaceutically acceptable salts thereof which may be used comprise: apazone, azapropazone, benzpiperylon, feprazone, mofebutazone, morazone, oxyphenbutazone, phenylbutazone, pipebuzone, propylphenazone, ramifenazone, suxibuzone and thiazolinobutazone. Structurally related pyrazalones having similar analgesic and anti-inflammatory properties are also intended to be encompassed by this group.

In another specific embodiment, the pharmaceutical composition described herein can comprise an inventive PLAD material in combination (pretreatment, post-treatment, or concurrent treatment) with any of one or more of the following NSAIDs: E-acetamidocaproic acid, S-adenosyl-methionine, 3-amino-4-hydroxybutyric acid, amixetrine, anitrazafen, antrafenine, bendazac, bendazac lysinate, benzydamine, beprozin, broperamole, bucolome, bufezolac, ciproquazone, cloximate, dazidamine, deboxamet, detomidine, difenpiramide, difenpyramide, difisalamine, ditazol, emorfazone, fanetizole mesylate, fenflumizole, floctafenine, flumizole, flunixin, fluproquazone, fopirtoline, fosfosal, guaimesal, guaiazolene, isonixirn, lefetamine HCl, leflunomide, lofemizole, lotifazole, lysin clonixinate, meseclazone, nabumetone, nictindole, nimesulide, orgotein, orpanoxin, oxaceprol, oxapadol, paranyline, perisoxal, perisoxal citrate, pifoxime, piproxen, pirazolac, pirfenidone, proquazone, proxazole, thielavin B, tiflamizole, timegadine, tolectin, tolpadol, tryptamid and those designated by company code number such as 480156S, AA861, AD1590, AFP802, AFP860, AI77B, AP504, AU8001, BPPC, BW540C, CHINOIN 127, CN100, EB382, EL508, F1044, FK-506, GV3658, ITF182, KCNTEI6090, KME4, LA2851, MR714, MR897, MY309, ONO3144, PR823, PV102, PV108, R830, RS2131, SCR152, SH440, SIR133, SPAS510, SQ27239, ST281, SY6001, TA60, TAI-901 (4-benzoyl-1-indancarboxylic acid), TVX2706, U60257, UR2301 and WY41770. Structurally related NSAIDs having similar analgesic and anti-inflammatory properties to the NSAIDs are also intended to be encompassed by this group.

In still another specific embodiment, the pharmaceutical composition described herein can comprise an inventive PLAD material in combination (pretreatment, post-treatment or concurrent treatment) with any of one or more corticosteroids, prodrug esters or pharmaceutically acceptable salts thereof for the treatment of the diseases and disorders recited herein, including acute and chronic inflammation such as rheumatic diseases, graft versus host disease and multiple sclerosis. Corticosteroids, prodrug esters and pharmaceutically acceptable salts thereof include hydrocortisone and compounds which are derived from hydrocortisone, such as 21-acetoxypregnenolone, alclomerasone, algestone, amcinonide, beclomethasone, betamethasone, betamethasone valerate, budesonide, chloroprednisone, clobetasol, clobetasol propionate, clobetasone, clobetasone butyrate, clocortolone, cloprednol, corticosterone, cortisone, cortivazol, deflazacon, desonide, desoximerasone, dexamethasone, diflorasone, diflucortolone, difluprednate, enoxolone, fluazacort, flucloronide, flumethasone, flumethasone pivalate, flucinolone acetonide, flunisolide, fluocinonide, fluorocinolone acetonide, fluocortin butyl, fluocortolone, fluocortolone hexanoate, diflucortolone valerate, fluorometholone, fluperolone acetate, fluprednidene acetate, fluprednisolone, flurandenolide, formocortal, halcinonide, halometasone, halopredone acetate, hydro-cortamate, hydrocortisone, hydrocortisone acetate, hydro-cortisone butyrate, hydrocortisone phosphate, hydrocortisone 21-sodium succinate, hydrocortisone tebutate, mazipredone, medrysone, meprednisone, methylprednisolone, mometasone furoate, paramethasone, prednicarbate, prednisolone, prednisolone 21-diedryaminoacetate, prednisolone sodium phosphate, prednisolone sodium succinate, prednisolone sodium 21-m-sulfobenzoate, prednisolone sodium 21-stearoglycolate, prednisolone tebutate, prednisolone 21-trimethylacetate, prednisone, prednival, prednylidene, prednylidene 21-diethylaminoacetate, tixocortol, triamcinolone, triamcinolone acetonide, triamcinolone benetonide and triamcinolone hexacetonide. Structurally related corticosteroids having similar analgesic and anti-inflammatory properties are also intended to be encompassed by this group.

In another specific embodiment, the pharmaceutical composition described herein can comprise an inventive PLAD material in combination (pretreatment, post-treatment, or concurrent treatment) with any of one or more slow-acting antirheumatic drugs (SAARDs) or disease modifying antirheumatic drugs (DMARDS), prodrug esters, or pharmaceutically acceptable salts thereof for the treatment of the diseases and disorders recited herein, including acute and chronic inflammation such as rheumatic diseases, graft versus host disease and multiple sclerosis. SAARDs or DMARDS, prodrug esters and pharmaceutically acceptable salts thereof comprise: allocupreide sodium, auranofin, aurothioglucose, aurothioglycanide, azathioprine, brequinar sodium, bucillamine, calcium 3-aurothio-2-propanol-1-sulfonate, chlorambucil, chloroquine, clobuzarit, cuproxoline, cyclophosphamide, cyclosporin, dapsone, 15-deoxyspergualin, diacerein, glucosamine, gold salts (e.g., cycloquine gold salt, gold sodium thiomalate, gold sodium thiosulfate), hydroxychloroquine, hydroxychloroquine sulfate, hydroxyurea, kebuzone, levamisole, lobenzarit, melittin, 6-mercaptopurine, methotrexate, mizoribine, mycophenolate mofetil, myoral, nitrogen mustard, D-penicillamine, pyridinol imidazoles such as SKNF86002 and SB203580, rapamycin, thiols, thymopoietin and vincristine. Structurally related SAARDs or DMARDs having similar analgesic and anti-inflammatory properties are also intended to be encompassed by this group.

In another specific embodiment, the pharmaceutical composition described herein can comprise an inventive PLAD material in combination (pretreatment, post-treatment, or concurrent treatment) with any of one or more COX2 inhibitors, prodrug esters or pharmaceutically acceptable salts thereof for the treatment of the diseases and disorders recited herein, including acute and chronic inflammation. Examples of COX2 inhibitors, prodrug esters or pharmaceutically acceptable salts thereof include, for example, celecoxib. Structurally related COX2 inhibitors having similar analgesic and anti-inflammatory properties are also intended to be encompassed by this group. Examples of COX-2 selective inhibitors include but not limited to etoricoxib, valdecoxib, celecoxib, licofelone, lumiracoxib, rofecoxib, and the like.

In still another specific embodiment, the pharmaceutical composition described herein can comprise an inventive PLAD material in combination (pretreatment, post-treatment, or concurrent treatment) with any of one or more antimicrobials, prodrug esters or pharmaceutically acceptable salts thereof for the treatment of the diseases and disorders recited herein, including acute and chronic inflammation. Antimicrobials include, for example, the broad classes of penicillins, cephalosporins and other beta-lactams, aminoglycosides, azoles, quinolones, macrolides, rifamycins, tetracyclines, sulfonamides, lincosamides and polymyxins. The penicillins include, but are not limited to penicillin G, penicillin V, methicillin, nafcillin, oxacillin, cloxacillin, dicloxacillin, floxacillin, ampicillin, ampicillin/sulbactam, amoxicillin, amoxicillin/clavulanate, hetacillin, cyclacillin, bacampicillin, carbenicillin, carbenicillin indanyl, ticarcillin, ticarcillin/clavulanate, azlocillin, mezlocillin, peperacillin, and mecillinam. The cephalosporins and other beta-lactams include, but are not limited to cephalothin, cephapirin, cephalexin, cephradine, cefazolin, cefadroxil, cefaclor, cefamandole, cefotetan, cefoxitin, ceruroxime, cefonicid, ceforadine, cefixime, cefotaxime, moxalactam, ceftizoxime, cetriaxone, cephoperazone, ceftazidime, imipenem and aztreonam. The aminoglycosides include, but are not limited to streptomycin, gentamicin, tobramycin, amikacin, netilmicin, kanamycin and neomycin. The azoles include, but are not limited to fluconazole. The quinolones include, but are not limited to nalidixic acid, norfloxacin, enoxacin, ciprofloxacin, ofloxacin, sparfloxacin and temafloxacin. The macrolides include, but are not limited to erythomycin, spiramycin and azithromycin. The rifamycins include, but are not limited to rifampin. The tetracyclines include, but are not limited to spicycline, chlortetracycline, clomocycline, demeclocycline, deoxycycline, guamecycline, lymecycline, meclocycline, methacycline, minocycline, oxytetracycline, penimepicycline, pipacycline, rolitetracycline, sancycline, senociclin and tetracycline. The sulfonamides include, but are not limited to sulfanilamide, sulfamethoxazole, sulfacetamide, sulfadiazine, sulfisoxazole and co-trimoxazole (trimethoprim/sulfamethoxazole). The lincosamides include, but are not limited to clindamycin and lincomycin. The polymyxins (polypeptides) include, but are not limited to polymyxin B and colistin.

Carriers and Formulations

With respect to inventive pharmaceutical compositions, the pharmaceutically acceptable carrier can be any of those conventionally used and is limited only by chemico-physical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. In one embodiment, the pharmaceutically acceptable carrier be one which is chemically inert to the active agent(s) and one which has no detrimental side effects or toxicity under the conditions of use.

The choice of carrier will be determined in part by the particular inventive PLAD material, as well as by the particular method used to administer the inventive PLAD material. Accordingly, there are a variety of suitable formulations of the pharmaceutical composition of the invention. The following formulations for oral, aerosol, parenteral, subcutaneous, intravenous, intramuscular, intraarterial, intrathecal, interperitoneal, rectal, and vaginal administration are exemplary and are in no way limiting. More than one route can be used to administer the inventive PLAD materials, and in certain instances, a particular route can provide a more immediate and more effective response than another route.

Topical formulations are well-known to those of skill in the art. Such formulations are particularly suitable in the context of the invention for application to the skin. The topical formulation can be a cream, ointment, patch, solution, aerosol spray, paste, film, and the like.

Formulations suitable for oral administration can consist of (a) liquid solutions, such as an effective amount of the inventive PLAD material dissolved in diluents, such as water, saline, or juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the inventive PLAD material in a flavor, usually sucrose and acacia or tragacanth, as well as pastilles comprising the inventive PLAD material in an inert base, such as gelatin and glycerin, or sucrose and acacia, emulsions, gels, and the like containing, in addition to, such excipients as are known in the art.

The inventive PLAD material, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The inventive PLAD material can be administered in a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-1,3-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5% to about 25% by weight of the inventive PLAD material in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Injectable formulations are in accordance with the invention. The requirements for effective pharmaceutical carriers for injectable compositions are well-known to those of ordinary skill in the art (see, e.g., *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Toissel, 4th ed., pages 622-630 (1986)). In one aspect, when administering cells, the cells are administered via injection, e.g., intravenous injection.

Additionally, the inventive PLAD materials, or compositions comprising such inventive PLAD materials, can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

It will be appreciated by one of skill in the art that, in addition to the above-described pharmaceutical compositions, the inventive PLAD materials of the invention can be formulated as inclusion complexes, such as cyclodextrin inclusion complexes, or liposomes.

Dose

For purposes of the invention, the amount or dose of the inventive PLAD material administered should be sufficient to effect, e.g., a therapeutic or prophylactic response, in the subject or animal over a reasonable time frame. For example, the dose of the inventive PLAD material should be sufficient to bind to a cancer antigen, or detect, treat or prevent cancer in a period of from about 1 to 4 weeks or longer, e.g., 5 to 20 or more weeks, from the time of administration. In certain embodiments, the time period could be even longer. The dose will be determined by the efficacy of the particular inventive PLAD material and the condition of the animal (e.g., human), as well as the body weight of the animal (e.g., human) to be treated.

Many assays for determining an administered dose are known in the art. For purposes of the invention, an assay, which comprises comparing the extent to which pulmonary inflammation (PI) or airway hyperresponsiveness (AHR) is inhibited in a mammal upon administration of a given dose of a PLAD pharmaceutical composition to the mammal among a set of mammals of which is each given a different dose of the pharmaceutical composition, could be used to determine a starting dose to be administered to a mammal. The extent to which AHR, PI, or both is inhibited can be assayed by methods known in the art, including, for instance, the methods described in Hammelmann et al., *Am. J. Respiratory & Critical Care Med.* 156: 766-775 (1997); Chen and Schuster, *Mol. Pharmaceutics.* 3: 488-495 (2006); and Kim et al., *Am. J. Physiol. Lung Cell Mol. Physiol.* 284: L503-:509 (2004).

The dose of the inventive PLAD material also will be determined by the existence, nature and extent of any adverse side effects that might accompany the administration of a particular inventive PLAD material. Typically, the attending physician will decide the dosage of the inventive PLAD material with which to treat each individual patient, taking into consideration a variety of factors, such as age, body weight, general health, diet, sex, inventive PLAD material to be administered, route of administration, and the severity of the condition being treated. By way of example and not intending to limit the invention, the dose of the inventive PLAD material can be about 0.0001 to about 1 g/kg body weight of the subject being treated/day, from about 0.0001 to about 0.001 g/kg body weight/day, or about 0.01 mg to about 1 g/kg body weight/day.

Targeted Forms

One of ordinary skill in the art will readily appreciate that the inventive PLAD materials of the invention can be modified in any number of ways, such that the therapeutic or prophylactic efficacy of the inventive PLAD materials is increased through the modification. For instance, the inventive PLAD materials can be conjugated either directly or indirectly through a linker to a targeting moiety. The practice of conjugating compounds, e.g., inventive PLAD materials, to targeting moieties is known in the art. See, for instance, Wadhwa et al., J Drug Targeting, 3, 111-127 (1995) and U.S. Pat. No. 5,087,616. The term "targeting moiety" as used herein, refers to any molecule or agent that specifically recognizes and binds to a cell-surface receptor, such that the targeting moiety directs the delivery of the inventive PLAD materials to a population of cells on which surface the receptor is expressed. Targeting moieties include, but are not limited to, antibodies, or fragments thereof, peptides, hormones, growth factors, cytokines, and any other natural or non-natural ligands, which bind to cell surface receptors (e.g., Epithelial Growth Factor Receptor (EGFR), T-cell receptor (TCR), B-cell receptor (BCR), CD28, Platelet-derived Growth Factor Receptor (PDGF), nicotinic acetylcholine receptor (nAChR), etc.). The term "linker" as used in context of a targeting moiety, refers to any agent or molecule that bridges the inventive PLAD materials to the targeting moiety. One of ordinary skill in the art recognizes that sites on the inventive PLAD materials, which are not necessary for the function of the inventive PLAD materials, are ideal sites for attaching a linker and/or a targeting moiety, provided that the linker and/ or targeting moiety, once attached to the inventive PLAD materials, do(es) not interfere with the function of the inventive PLAD materials.

Depot

Alternatively, the inventive PLAD materials can be modified into a depot form, such that the manner in which the inventive PLAD materials is released into the body to which it is administered is controlled with respect to time and location within the body (see, for example, U.S. Pat. No. 4,450, 150). Depot forms of inventive PLAD materials can be, for example, an implantable composition comprising the inventive PLAD materials and a porous or non-porous material, such as a polymer, wherein the inventive PLAD materials is encapsulated by or diffused throughout the material and/or degradation of the non-porous material. The depot is then implanted into the desired location within the body and the inventive PLAD materials are released from the implant at a predetermined rate.

Use

Without being bound to any particular theory, the inventive PLAD polypeptides and PLAD-binding polypeptides are believed to inhibit the multimerization of a receptor complex comprising an IL-17 receptor family member, e.g., inhibits IL-17RA homodimerization, which multimerization is necessary for IL-17-mediated signaling (signal transduction initiated by the binding of an IL-17 ligand to a receptor complex comprising an IL-17R family member). Also, the inventive PLAD polypeptides and PLAD-binding polypeptides are further believed to inhibit the binding of an IL-17 ligand to receptor complex comprising an IL-17R family member, which in turn inhibits IL-17-mediated signaling.

In this regard, the invention provides a method for inhibiting multimerization of a receptor complex comprising an IL-17 receptor (IL-17R) family member in a cell. The method comprises contacting the cell with any of the above described PLAD polypeptides, PLAD-binding polypeptides, a chimeric proteins, nucleic acids, vectors, host cells, or conjugates, or a combination thereof, in an amount effective to inhibit multimerization of the receptor complex in the cell.

The invention also provides a method of inhibiting the binding of an IL-17 ligand to a receptor complex comprising an IL-17R family member in a cell. The method comprises contacting the cell with any of the above described PLAD polypeptides, PLAD-binding polypeptides, a chimeric proteins, nucleic acids, vectors, host cells, or conjugates, or a combination thereof, in an amount effective to inhibit binding of the IL-17 ligand to the receptor complex in the cell.

The invention furthermore provides a method of inhibiting signal transduction initiated by an IL-17 ligand binding to a receptor complex comprising an IL-17 receptor (IL-17R) family member expressed on the surface of a cell. The method comprises contacting the cell with any of the above described PLAD polypeptides, PLAD-binding polypeptides, chimeric proteins, nucleic acids, vectors, host cells, or conjugates, or a combination thereof, in an amount effective to inhibit the signal transduction in the cell.

With regard to the foregoing methods, the IL-17 ligand can be any of the IL-17 ligands described herein. Also, the receptor complex can comprise any of the IL-17R family members described herein. In one aspect, the receptor complex comprises IL-17RA, IL-17RB, IL-17C, or any combination thereof.

IL-17-mediated signaling has been known to lead to the production of certain cytokines, chemokines, matrix metalloproteinases (MMPs), and other molecules associated with IL-17-mediated signal transduction. In this regard, the invention further provides a method of inhibiting the production of at least one cytokine, chemokine, matrix metalloproteinase, or other molecule associated with IL-17-mediated signal transduction in a cell. The method comprises contacting the cell with any of the above described PLAD polypeptides, PLAD-binding polypeptides, chimeric proteins, nucleic acids, vectors, host cells, or conjugates, or a combination thereof, in an amount effective to inhibit the production of the cytokine, chemokine, matrix metalloproteinase, or other molecule associated with IL-17-mediated signal transduction. In one embodiment, the cytokine, chemokine, matrix metalloproteinase, or other molecule associated with IL-17-mediated signal transduction can be any of IL-6, IL-8, CXCL1, CXCL2, GM-CSF, G-CSF, M-CSF, IL-1â, TNFα, RANK-L, LIF, PGE2, IL-12, MMP3, MMP9, GROcc, NO, and C-telopeptide.

IL-17-mediated signaling also has been implicated in a number of diseases. For example, increased levels of the IL-17A ligand and/or involvement of IL-17A ligand-mediated signals in disease pathogenesis have been demonstrated in a variety of conditions and diseases. Kolls and Linden, 2004, supra; Miossec, 2003, *P. Arthritis Rheum.* 48:594-601); International Patent Application Publication No. WO 2005/ 063290; Cannetti et al., 2003, *J. Immunol.* 171:1009-1015; Charles et al., 1999, *J. Immunol.* 163: 1521-1528; Cunnane et al., 2000, *Online J. Rheumatol.* 27:58-63; Yoshimoto, 1998, *J. Immunol.* 161: 3400-3407), (International Patent Application Publication No. WO 2005/063290), (Niederau, 1997, Online NLM), (International Patent Application Publication No. WO 2004/002519), (Tsutsui et al., 2000, supra), (Konishi et al., 2002, *Proc. Natl. Acad. Sci. U.S.A.* 99:11340-11345), Ziolkowska et al., 2000, supra); (Chabaud, 2001, *Arth & Rheumatism*, 44:1293). Thus, IL-17RA is said to influence the pathology of these and other diseases or conditions described herein.

It is accordingly contemplated that the inventive PLAD materials (e.g., inventive PLAD polypeptides, PLAD-binding polypeptides, chimeric proteins, functional variants, functional fragments, nucleic acids, vectors, host cells, populations of cells, and conjugates) or pharmaceutical compositions comprising the same can be used in methods of treating a disease which is associated with IL-17-mediated signaling. In this regard, the invention provides a method of treating a disease in a subject, comprising administering to the subject any of the pharmaceutical compositions described herein in an amount effective to treat the disease in the host.

With regard to the inventive treating method, the disease can be any disease which is associated with IL-17-mediated signaling. The IL-17 can be any IL-17 molecule known in the art, including, those described herein (e.g., IL-17A, IL-17B, IL-17C, IL-17D, IL-17E, and IL-17F). The disease associated with IL-17-mediated signaling can be any disease, condition, or pathology whose onset in a patient is caused or exacerbated by IL-17-mediated signaling. The severity of the disease, condition, or pathology also can be increased or decreased by the modulating the IL-17-mediated signaling.

In this regard, the disease can be an inflammatory disease or an autoimmune disease. For purposes herein, "autoimmune disease" refers to a disease in which the body produces an immunogenic (i.e., immune system) response to some constituent of its own tissue. In other words, the immune system loses its ability to recognize some tissue or system within the body as "self and targets and attacks it as if it were foreign. Autoimmune diseases can be classified into those in which predominantly one organ is affected (e.g., hemolytic anemia and anti-immune thyroiditis), and those in which the autoimmune disease process is diffused through many tissues (e.g., systemic lupus erythematosus). For example, multiple sclerosis is thought to be caused by T cells attacking the sheaths that surround the nerve fibers of the brain and spinal cord. This results in loss of coordination, weakness, and blurred vision. Autoimmune diseases are known in the art and include, for instance, Hashimoto's thyroiditis, Grave's disease, lupus, multiple sclerosis, rheumatic arthritis, hemolytic anemia, anti-immune thyroiditis, systemic lupus erythematosus, celiac disease, Crohn's disease, colitis, diabetes, scleroderma, psoriasis, and the like.

Also, the disease can be inflammation, cartilage inflammation, and/or bone degradation, arthritis, rheumatoid arthritis, juvenile arthritis, juvenile rheumatoid arthritis, pauciarticular juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reter's Syndrome, SEA Syndrome (Seronegativity, Enthesopathy, Arthropathy Syndrome), juvenile dermatomyositis, juvenile psoriatic arthritis, juvenile scleroderma, juvenile systemic lupus erythematosus, juvenile vasculitis, pauciarticular rheumatoid arthritis, polyarticular rheumatoid arthritis, systemic onset rheumatoid arthritis, ankylosing spondylitis, enteropathic arthritis, reactive arthritis, Reter's Syndrome, SEA Syndrome (Seronegativity, Enthesopathy, Arthropathy Syndrome), dermatomyositis, psoriatic arthritis, scleroderma, systemic lupus erythematosus, vasculitis, myolitis, polymyolitis, dermatomyolitis, osteoarthritis, polyarteritis nodossa, Wegener's granulomatosis, arteritis, ploymyalgia rheumatica, sarcoidosis, scleroderma, sclerosis, primary biliary sclerosis, sclerosing cholangitis, Sjogren's syndrome, psoriasis, plaque psoriasis, guttate psoriasis, inverse psoriasis, pustular psoriasis, erythrodermic psoriasis, dermatitis, atopic dermatitis, atherosclerosis, lupus, Still's disease, Systemic Lupus Erythematosus (SLE), myasthenia gravis, inflammatory bowel disease (IBD), Crohn's disease, ulcerative colitis, celiac disease, multiple schlerosis (MS), asthma, COPD, Guillain-Barre disease, Type I diabetes mellitus, Graves' disease, Addison's disease, Raynaud's phenomenon, autoimmune hepatitis, GVHD, and the like.

Alternatively, as IL-17 has been implicated in the worsening of certain infectious diseases (Rutitzsky, *J. Immunol.* 180: 2486-2495 (2008); and Romani et al., *J. Immunol.* 180: 5157-5162 (2008)) the disease which can be treated can be an infectious disease. For purposes herein, "infectious disease" means a disease that can be transmitted from person to person or from organism to organism, and is caused by a microbial agent (e.g., common cold). Infectious diseases are known in the art and include, for example, hepatitis, sexually transmitted diseases (e.g., *Chlamydia*, gonorrhea), tuberculosis, HIV/AIDS5 diphtheria, hepatitis B, hepatitis C, cholera, and influenza. The infectious disease can be schistosomiasis or gastric candidiasis.

With regard to the inventive treating method, the pharmaceutical composition can be administered through any route of administration, including any of those mentioned herein. For example, the pharmaceutical composition can be administered orally, subcutaneously, intravenously, topically, parenterally, vaginally, rectally, etc.

The terms "treat," and "inhibit" as well as words stemming therefrom, as used herein, do not necessarily imply 100% or complete treatment or inhibition. Rather, there are varying degrees of treatment or inhibition of which one of ordinary skill in the art recognizes as having a potential benefit or therapeutic effect. In this respect, the inventive methods can provide any amount or any level of treatment of a disease in a subject. Furthermore, the treatment provided by the inventive method can include treatment of one or more conditions or symptoms of the disease being treated. Also, for purposes herein, "treatment" encompasses delaying the onset of the disease, or a symptom or condition thereof, and includes the prevention of further pathophysiology of the disease. Further in this respect, the inventive methods can provide any amount or any level of inhibition of multimerization of a receptor complex comprising an IL-17R family member, inhibition of IL-17-mediated signal transduction, inhibition of IL-17 ligand binding to its receptor complex comprising an IL-17R family member, or inhibition of the production of a cytokine, chemokine, MMP, or other molecule associated with IL-17 ligand-mediated signaling.

Cell Administration

For purposes of the inventive methods, wherein host cells or populations of cells are administered to the subject, the cells can be cells that are allogeneic or autologous to the subject. In one aspect of the invention, the cells are autologous to the subject.

Subjects

The subject referred to herein can be any subject. In one embodiment of the invention, the subject is a mammal. As used herein, the term "mammal" refers to any mammal, including, but not limited to, mammals of the order Rodentia, such as mice and hamsters, and mammals of the order Logomorpha, such as rabbits. In one aspect, the mammals are from the order Carnivora, including Felines (cats) and Canines (dogs). In one embodiment, the mammals are from the order Artiodactyla, including Bovines (cows) and Swines (pigs) or of the order Perssodactyla, including Equines (horses). In another aspect of the invention, the mammals are of the order Primates, Ceboids, or Simoids (monkeys) or of the order Anthropoids (humans and apes). In one aspect of the invention, mammal is the human.

Diagnostic Uses

The inventive PLAD materials of the invention can be used in diagnostic assays, e.g., binding assays to detect and/or quantify an IL-17R family member or an IL-17 ligand expressed in a tissue or cell, which can be indicative of disease onset, disease progression, or disease regression.

Research Uses

The inventive PLAD materials may be used in research to further investigate the role of an IL-17 ligand and/or an IL-17R family member in, for example, a disease. The inventive PLAD materials may be used to further investigate the role of receptor complexes comprising an IL-17R family member and the role of IL-17-mediated signaling in disease. The inventive PLAD materials may be used, for example, to further investigate the kinetics and other biophysical properties of the interaction between the IL-17R family members during multimerization and/or the interaction between an IL-17 ligand and a receptor complex comprising an IL-17R family member.

In another embodiment, the invention provides for methods of screening for a PLAD binding molecule, such as PLAD binding polypeptides. These methods comprising contacting the PLAD polypeptide of the invention and a test compound, and detecting specific binding of the PLAD polypeptide and the test agent, wherein specific binding of the test agent to the PLAD polypeptide indicates the test compound is a PLAD binding molecule. Test compounds include antibodies known to bind to an IL-17R family member.

Also, a method of screening for an inhibitor of PLAD association, e.g., PLAD multimerization, is provided by the invention. The method comprises contacting a cell expressing a receptor complex comprising an IL-17R family member, or a PLAD-containing fragment thereof, with a test compound and measuring PLAD multimerization. An inhibition of PLAD multimerization indicates that the test compound is an inhibitor of PLAD association. In this way, potential therapeutics for the disease set forth herein could be identified.

With respect to the inhibitory methods described herein, many assays for measuring receptor multimerization, IL-17-mediated signaling, IL-17 receptor complex binding, and IL-17-induced production of a cytokine, chemokine, MMP, or other molecule, are known in the art. See, for example, Examples 1, 3, 4, and 12 and Kramer et al., *J. Immunol.* 179: 6379-6383 (2007) for receptor multimerization assays; Examples 7, 8, 10, 11, and 13 for IL-17-mediated signaling assays; Example 5 for IL-17 receptor complex binding assays; Examples 7 and 8 for assays for IL-17-induced production of a cytokine, chemokine, MMP, or other molecule.

Second Medical Use

All aspects of the inventive PLAD materials described herein may be used in the preparation of a medicament for the treatment of the various conditions and diseases described herein.

The following examples further illustrate the invention but should not be construed as in any way limiting its scope.

EXAMPLES

Example 1

This Example describes the materials and method employed to obtain the results presented in the subsequent Examples. The following abbreviations may be used in the Examples: AD, activation domain; BD, DNA binding domain; ECD, extracellular domain; EPO, erythropoietin; FRET, fluorescence resonance energy transfer; FL, full length; FN, fibronectin III-like; RA, rheumatoid arthritis; Y2H, yeast two hybrid.

Molecular Modeling

Using Feature aligner at SWISS-PROT, the extracellular sequences of murine and human IL-17RA were submitted to PHYRE. PHYRE returns the highest scoring coordinates in PDB format fabricating a 3D model, using a series of algorithms to arrive at a consensus model. Since only the highest scoring domains are returned, other domains were found through resubmission of unscored domains. Coordinates were displayed and manipulated on an sgi Tezro with Accelrys Insight II (2005) software. Coordinates are available for all modeling figures.

Plasmids, Cell Culture, Luciferase Assays and Cytokine Stimulations

IL-17RA constructs were fused to FLAG and enhanced YFP and CFP (BD Clontech). HEK293 cells and IL-17RAKO fibroblasts were maintained in Amem (Sigma, St. Louis Mo.) with 10% FBS (Gemini Products, Woodland Calif.) and antibiotics. Cells were transfected with Fugene 6 (Roche, Indianapolis Ind.) and selected in G418 or Hygromycin B. Recombinant cytokines were obtained from R&D Systems (Minneapolis, Minn.) or Peprotech (Rocky Hill, N.J.) and used at 100 ng/ml (IL-17, IL-17F) or 2 ng/ml (TNFα). Luciferase assays were performed with the mouse 24p3-Luc reporter vector according to standard techniques.

Yeast 2 Hybrid Analyses

The IL-17RA ECD, FN2, FN2/linker and FN1 domains were fused to the Gal4 DNA binding domain (BD) or activation domain (AD) in the Pgbkt7 and Pgadat7 yeast expression plasmids (BD Clontech). *S. cerevisiae* were transformed by standard methods, and growth on Leu-Trp-deficient plates or Leu-Trp-Ade-deficient plates was evaluated by colony counting. CARMA1 (provided by X. Lin, MD Anderson Cancer Center, Houston Tex.) was used a positive control.

Flow Cytometry and FRET

Cells were incubated with M750 or M177 anti-mouse IL-17RA followed by anti-rat PE (BD Pharmigen). To prepare huIL-17.Fc, a cDNA encoding huIL17, N-terminal flag and huFC (IgG1) was amplified by PCR and cloned into the Pdc409 vector. Secreted IL17.Fc was purified from transfected COS cells over a Protein A column and its concentration determined using a human Fc ELISA. For binding, 293 cells were blocked with anti-human IL-17RA (M202) and stained with huIL17.Fc followed by anti-huIgG-APC (Jackson Immunoresearch, West Grove, Pa.). Data were analyzed on a FACSCalibur with Cell Quest software (BD Biosciences). FRET data were obtained from three channel images using the macro of LSM FRET tool software (Zeiss AIM software, per standard techniques). A minimum of 50 regions of interest at the membrane were assessed for each condition. FRET efficiencies were calculated by the NFRET method and significance determined by t-test.

Example 2

To investigate the structure of the IL-17RA extracellular domain (ECD), we used PHYRE, a 3-D modeling program that incorporates multiple structure prediction algorithms to determine secondary and tertiary structures based on comparison to other crystallized proteins. This analysis predicted the presence of two separable fibronectin III-like (FN) domains (termed FN1 and FN2) joined by a non-structured linker. Similar structures were obtained for both murine and human receptors (FIG. 1A and data not shown). Based on this model, deletions in the IL-17RA ECD were made to assess the functional significance of the FN and linker regions (FIG. 1B).

Example 3

To evaluate the role of FN domains in receptor self-association, we first used a yeast two-hybrid (Y2H) approach (Table 1). We could not verify whether a full length IL-17RA ECD interacted with itself, as this construct exhibited constitutive transcriptional activity when fused to the Gal4 activation domain (AD) (data not shown). However, productive association was observed between a full length (FL) IL-17RA ECD and the FN2 domain, but not between FL and FN1 (rows I-K). Consistent with this, the FN2linker or FN2 constructs were capable of self-association (rows O-P), but did not substantially interact with FN1 (rows M-N). FN1 was not capable of self-association (row L). Together, these results indicated that FN2 but not FN1 mediates oligomerization of IL-17RA subunits, and that the inter-FN linker is dispensable.

To obtain the data presented Table 1, full length (FL) IL-17RA or the FN1, FN2/linker or FN2 domains were fused to the yeast Gal4 DNA binding domain (BD) or activation domain (AD) in the pGBKT7 and pGADT7 plasmids. *S. cerevisiae* were transformed with the indicated pairs of plasmids and growth on Leu-Trp-deficient plates (selecting for both plasmids) or Leu-Trp-Ade-deficient plates (selecting for each plasmid and an interaction) was evaluated. CARMA1 was a positive control. FL, full length. FN, fibronectin.

TABLE 1

Homotypic interactions between IL-17RA occur via the FN2linker domain.

| | pGBKT7 (BD construct) | pGADT7 (AD construct) | Growth on - Leu/-Trp | Growth on - Leu/-Trp/-Ade |
|---|---|---|---|---|
| A | none | none | — | — |
| B | FL | AD | ++++ | — |
| C | FN1 | AD | ++++ | — |
| D | FN2linker | AD | ++++ | — |
| E | FN2 | AD | ++++ | |
| F | BD | FN1 | ++++ | +/ |
| G | BD | FN2linker | ++++ | — |
| H | BD | FN2 | ++++ | |
| I | FL | FN1 | ++++ | +/ |
| J | FL | FN2linker | ++++ | ++++ |
| K | FL | FN2 | ++++ | ++++ |
| L | FN1 | FN1 | ++++ | — |
| M | FN1 | FN2linker | ++++ | + |
| N | FN2linker | FN1 | ++++ | +/ |
| O | FN2linker | FN2linker | ++++ | ++++ |
| P | FN2 | FN2 | ++++ | ++++ |
| Q | CARMA1 | CARMA1 | ++++ | ++++ |

Example 4

Figure 2A:
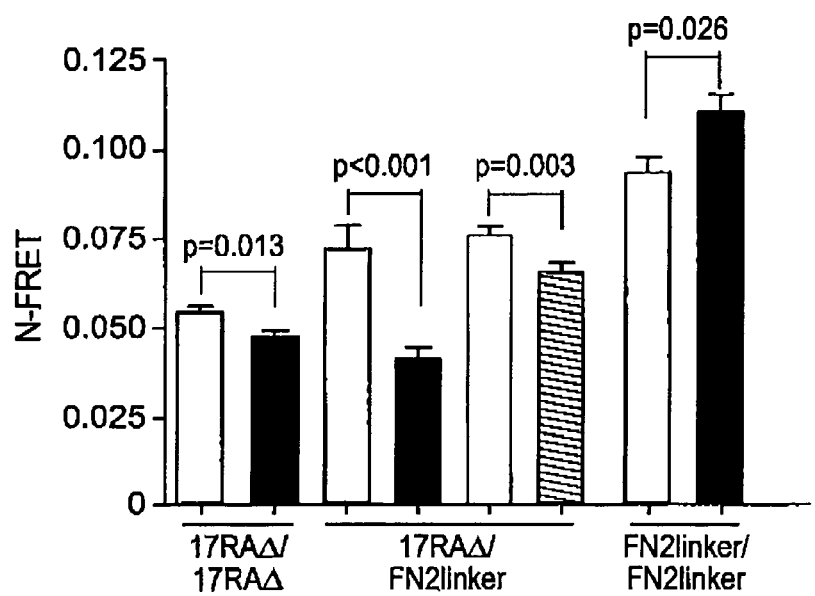
FIG. 2A is a graph of the N-FRET of IL-17-treated (black bars), IL-17F-treated (gray bars), and untreated (white bars) HEK293 cells expressing IL-17RAΔ/CFP or /YFP or IL-17RAΔFN2/CFP or /YFP in the indicated combinations. The FN2linker domain drives ligand-independent association in living cells. HEK293 cells were assayed for FRET in the absence or presence of IL-17 or IL-17F (100 ng/ml for 10 mins).
Figure 2B:
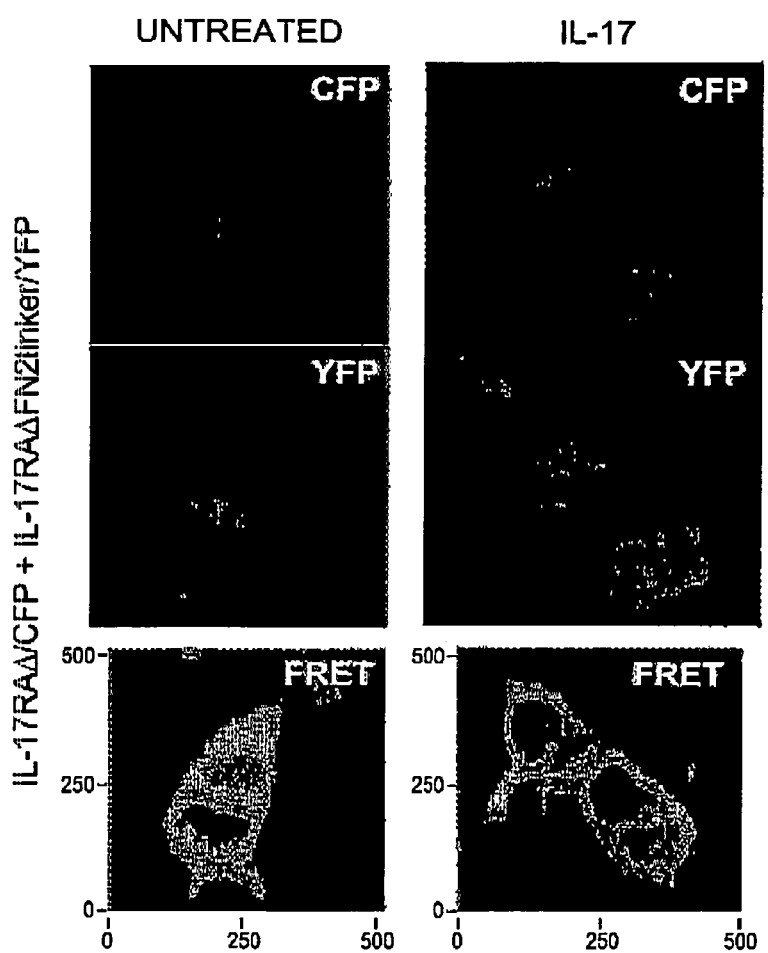
FIG. 2B are representative images of IL-17RAΔ/CFP paired with IL-17RAΔFN2/YFP. CFP (top) and YFP (middle) emission and FRET images (bottom) are shown.

To substantiate the data obtained in Example 3 in a physiological setting, we performed FRET studies in HEK293 cells. For this purpose, a construct encoding the complete IL-17RA ECD and transmembrane (TM) domain was fused to CFP (FIG. 1B; for convenience of expression, the cytoplasmic tail was truncated at residue 525 and termed IL-17RAΔ; in prior studies, the FL and truncated forms of IL-17RA showed identical FRET properties (Kramer, et al. (2006) J Immunol 176, 711-715). IL-17RAΔ/CFP was coexpressed with a construct encoding the FN2/linker region fused to YFP (residues 152-525, termed IL-17RAΔFN2linker) (FIG. 1B). In addition, IL-17RAΔFN2/CFP was co-expressed with IL-17RAΔFN2linker/YFP to determine whether the FN2/linker region is sufficient to mediate IL-17RA self-association. Consistent with our previous findings, co-expression of IL-17RAΔ/CFP with IL-17RAΔ/YFP resulted in significant FRET efficiency, suggesting the presence of a PLAD somewhere in IL-17RA (FIG. 2A). Pairing IL-17RAΔ/CFP with IL-17RAΔFN2linker/YFP also showed FRET (FIG. 2A-B). Moreover, IL-17RAΔFN2linker/CFP co-expressed with IL-17RAΔFN2linker/YFP resulted in a positive FRET signal. Together, these data are consistent with the yeast 2-hybrid results, and indicate that the FN2/linker domain mediates ligand-independent IL-17RA oligomerization. Hence the IL-17RA PLAD appears to lies within this domain.

As also observed previously, addition of IL-17 decreased FRET efficiency when IL-17RAΔ/CFP was paired with IL-17RAΔ/YFP (Kramer, et al. (2006) J Immunol 176, 711-715). A similar decrease in FRET was observed when IL-17RAΔ/CFP was paired with IL-17RAΔFN2linker/YFP and treated with IL-17 or IL17F (FIG. 2A), suggesting that loss of a single FN1 domain does not detectably modify interactions between receptor subunits, at least as visualized by this assay. However, addition of IL-17 to cells co-expressing IL-17RAΔFN2linker/CFP and IL-17RAΔFN2linker/YFP resulted in a reproducible increase in FRET (FIG. 2A). These findings suggest that dynamic interactions between IL-17RA subunits are altered when both FN1 domains are absent.

Figure 3A:
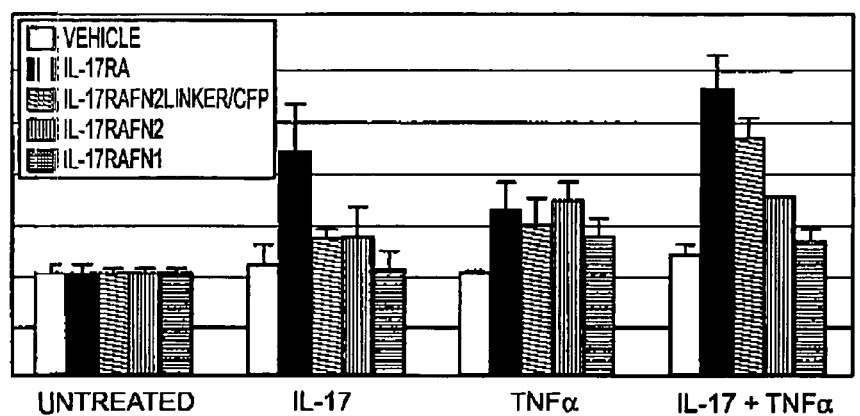
FIG. 3A demonstrates the FN1 domain is dispensable but the inter-FN linker domain is required for IL-17-dependent signal transduction. IL-17RA-deficient fibroblasts were transiently transfected in triplicate with the indicated IL-17R constructs and the 24p3-promoter fused to luciferase. Cells were stimulated with IL-17 (100 ng/ml) and/or TNFα (2 ng/ml), and after 6 h luciferase activity was assessed and normalized to an internal R-Luc control. SD are shown. ‡ p<0.05; *p<0.005. B. IL17RA neutralizing Abs bind to the FN2linker domain. HEK293 cells transfected with IL-17RΔ/CFP (top) or IL-17RAΔFN2linker/CFP (bottom) were incubated with a non-neutralizing (M177) or neutralizing Ab (M750) to murine IL-17RA. Filled histograms are isotype controls. C. The FN2linker domain binds IL-17 very weakly. The indicated cell lines were stained with huIL-17.Fc followed by anti-Fc-APC after blocking endogenous human IL-17RA.

The location of the IL-17 binding site on IL-17RA is unknown. The fact that there was an IL-17-induced change in FRET in cells expressing IL-17RAΔFN2linker (FIG. 2A-B) suggested that this construct retains the ligand binding site. Therefore, to determine requirements for IL-17-mediated signaling, IL-17RAFN2linker and IL-17RAFN1 (which encode full length cytoplasmic tails, FIG. 1B) were co-transfected into IL-17RA-deficient fibroblasts together with an IL-17-responsive 24p3 reporter. IL-17RAFN2linker but not IL-17RAFN1 showed IL-17-inducible activity, both alone or in the presence of TNFα (FIG. 3A). Although the signal was reproducibly weaker than a WT receptor, these data nonetheless indicate that the FN1 domain is not essential for signal transduction. However, the linker region appears to be critical, as IL-17RAFN2 lacking the linker reproducibly fails to mediate detectable signal transduction (FIG. 3A). Therefore, signaling function requires the linker domain but not FN1.

Example 5

Figure 3B:
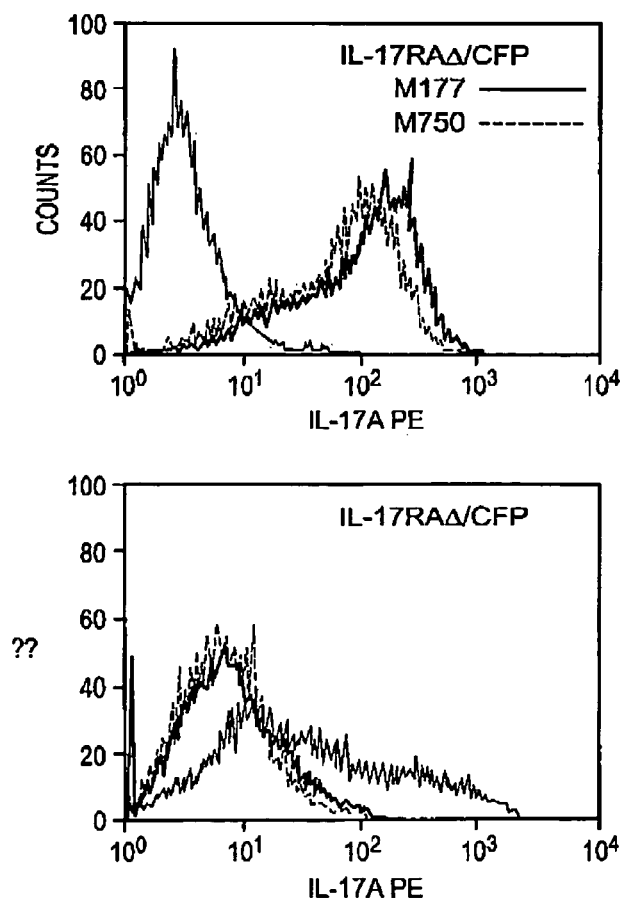
FIG. 3 demonstrates the requirements for signal transduction and ligand binding.

To further evaluate the IL-17 interaction site, cells expressing IL-17RAΔ or IL-17RAΔFN2linker were stained with 2 Abs to murine IL-17RA. As expected, both Abs stained IL-17RAΔ, since the entire ECD is preserved (FIG. 3B, top panel). Strikingly, a neutralizing Ab to IL-17RA (M750) stained cells expressing IL-17RAΔFN2linker, whereas a non-neutralizing antibody (M177) did not (FIG. 3B, bottom panel), also consistent with the presence of an IL-17-binding site within the FN2/linker. Surprisingly, however, when cells expressing the IL-17RAΔFN2linker construct were stained with IL-17 fused to human Fc (IL17.Fc), only a very weak fluorescent signal was observed (FIG. 3C, bottom panel). The FN2 domain construct did not bind IL-17 at all, also consistent with a requirement of the linker for ligand binding. Therefore, the FN1 domain appears to be critical for efficient ligand binding, even though in its absence detectable signaling can be observed in high concentrations of IL-17 (FIG. 3A). Collectively, these data indicate that the PLAD lies within the FN2 region of IL-17RA, whereas ligand binding also requires the linker and FN1 domains. However, despite the ability of IL-17 to bind IL-17RA and signal via the FN2/linker, a receptor complex lacking both FN1 domains is unable to bind IL-17 normally or induce the same apparent conformational alternation that occurs upon ligand binding to an intact IL-17RA ECD (FIG. 2A, FIG. 3) (Kramer, et al. (2006) J Immunol 176, 711-715).

Discussion of the Foregoing Examples

Our results based on yeast two-hybrid studies and FRET microscopy showed that the FN2 region of IL-17RA mediates ligand-independent receptor multimerization, whereas the linker domain and FN1 regions are not essential in this regard (Table 1, FIG. 2). Although FN1 is dispensable for pre-assembly and IL-17 binding, our data indicate a function for this subdomain in mediating conformational alterations in the receptor complex that follow ligand binding. Specifically, an increased FRET signal occurred in cells expressing two IL-17RAΔFN2linker constructs after treatment with IL-17, in contrast to the decreased FRET that occurs in cells expressing at least one intact IL-17RA ECD (FIG. 2A-B, (Kramer, et al. (2006) J Immunol 176, 711-715)). Therefore, a function of FN1 may be to reconfigure the relative positions of IL-17RA subunits in order to permit recruitment of an additional subunit to the complex (modeled in FIG. 3). There is precedent for ligands to induce large movements in the constituent subunits of cytokine receptors (e.g., the EPO receptor) (Remy, et al. (1999) Science 283, 990-993; Livnah, et al. (1999) Science 283, 987-990) as well as in bacterial quorum sensing receptors (Neiditch, et al. (2006) Cell 126, 1095-1108.). Interestingly, only one FN1 domain seems to be required for this event in IL-17RA, since IL-17RAΔ paired with IL-17RAΔFN2 showed the same decrease in FRET as a pairing of two intact IL-17RAΔ receptors (FIG. 2A, FIG. 3).

Receptor re-configuration in the IL-17 receptor complex may involve another subunit, such as IL-17RC, which has been found to be a necessary component of the human IL-17R signaling complex (Toy, et al. (2006) J Immunol 177, 36-39). Alternatively, the FN1 domain may function as a ligand affinity modulator, analogous to the IL-2Rα/CD25 subunit that enhances IL-2 receptor affinity 100-fold (Gaffen, S. L. (2001) Cytokine 14, 63-77)). In this case, the FN1 domain may be critical in settings where concentrations of IL-17 are limiting. Support for this model comes from our finding that IL-17-dependent signaling occurs in the absence of FN1, but is reduced compared to full length IL-17RA (FIG. 3A). Moreover, IL-17 binding to a receptor lacking FN1 was severely compromised (FIG. 3C), indicating that efficient ligand binding involves the FN1 region. While FN1 does not exhibit homomeric interactions (Table 1) and is insufficient for mediating IL-17-dependent signaling (FIG. 3A), it is possible that it interacts instead with IL-17RC or directly with ligand.

Thus, the foregoing Examples show that the FN2/linker domain encodes the IL-17 binding site, which has never before been mapped (FIG. 3), and IL-17-mediated signaling requires the linker domain (FIG. 3A). Interestingly, these data indicate that the PLAD and ligand binding domains are separable. In the TNFR, the PLAD and ligand binding domains are also located on different cysteine-rich domains, but ligand binding is nonetheless dependent on the presence of an intact PLAD.

Example 6

This example demonstrates a method of optimized constructs encoding a soluble PLAD polypeptide.

A first generation of constructs encoding a soluble human or mouse PLAD polypeptide comprising the FN2 of IL-17RA (with and without the linker region) were made using recombinant methods. All constructs were based on a pTT5 vector backbone and encoded the Igκ secretion signal sequence N-terminal to the PLAD polypeptide. Additionally, all constructs encoded C-terminal to the PLAD polypeptide a spacer/tag comprising the amino acid sequence of a GSSlinker followed by a FLAG tag, a second GSS linker, and a 6-His tag (SEQ ID NO: 21). A construct encoding a PLAD polypeptide containing just the FN2 of human IL-17RA encoded the amino acid sequence of SEQ ID NO: 32. A construct encoding a PLAD polypeptide containing the FN2 and the linker of human IL-17RA encoded the amino acid sequence of SEQ ID NO: 31. A construct encoding a PLAD polypeptide containing just the FN2 of mouse IL-17RA encoded the amino acid sequence of SEQ ID NO: 34. A construct encoding a PLAD polypeptide containing the FN2 and the linker of either mouse IL-17RA encoded the amino acid sequence of SEQ ID NO: 33. The constructs were transiently transfected into HK293 cells for expression and analyzed for expression. Expression levels of the PLAD protein was insufficient. It was speculated that the first generation PLAD constructs were in a highly aggregated state.

Mass spectrometry data (as shown pictorially in FIG. 8) demonstrated that an odd number of Cys residues were encoded by the constructs and it was thought that the lack of a disulfide bridge pairing was at least part of the problem for cell expression. Thus, a second generation of PLAD constructs were made which differed from the first generation of PLAD constructs by the addition of a C-terminal extension including three additional Cys residues in the second generation of PLAD constructs. In the PLAD constructs encoding a FN2 or a FN2 and a linker of a human IL-17RA, the constructs additionally encoded C-terminal to the FN2 the amino acid sequence of SEQ ID NO: 10. In the PLAD constructs encoding a FN2 or a FN2 and a linker of a mouse IL-17RA, the construct additionally encoded C-terminal to the FN2 the amino acid sequence of SEQ ID NO: 9. The location of the end of the human IL-17RA amino acid in the first generation of constructs is indicated in FIG. 9 as a vertical line labeled "Old end", whereas the location of the end of the human IL-17RA amino acid in the second generation of constructs is indicated in FIG. 9 as a vertical line labeled "New end." The location of the end of the mouse IL-17RA amino acid in the first generation of constructs is indicated in FIG. 10 as a vertical line labeled "Old end", whereas the location of the end of the mouse IL-17RA amino acid in the second generation of constructs is indicated in FIG. 10 as a vertical line labeled "New end."

The constructs were transiently transfected into HK293 cells for expression and analyzed for expression. The cells expressed the constructs encoding the linker and FN2 of the IL-17RAs. However, the constructs encoding only the FN2 of the IL-17RAs still did not express well. It was speculated that the secretion signal was not cleaved properly and that the Pro residue located at the N-terminus of the FN2 might cause improper folding of the resultant polypeptide.

Accordingly, a third generation of constructs encoding just the FN2 of either the mouse or human IL-17RA was generated. These constructs were the same as those in the second generation, except that each construct encoded LWD (SEQ ID NO: 15) N-terminal to the FN2. The constructs were transiently transfected into HK293 cells for expression and analyzed for expression. The cells expressed all of the constructs of the third generation.

Example 7

This example demonstrates a method of testing the activity of the first generation of PLAD constructs described in Example 6.

Normal human foreskin fibroblasts (HFF), which are adherent cells, were cultured in a T175 flask housed in a 37° C., 10% $CO_2$ incubator until approximately 85% confluency was reached. The cells were washed gently with PBS, and then trypsin was added to release the cells. Once released, cell culture media was added to the cells to inactivate the trypsin. The cells were pelleted by centrifuging at 1000 rpm for 5 minutes. The supernatant was removed and the cells were resuspended in a fixed volume of media. After counting with a hemacytometer, HFF were seeded at 5,000 cells per well in 200 μL culture medium in a 96-well polystyrene tissue culture plate format and let sit for 90 minutes in a 37° C., 10% $CO_2$ incubator. Stimulation factors (described below) were added and the cells were incubated for 24 hours (37° C., 10% $CO_2$) after which the plates were centrifuged for 10 minutes at 1200 rpm and the supernatant collected for immediate analysis.

The cells were incubated for 45 minutes with titrating concentrations of either recombinant human IL-17R PLAD-linker or human IL-17R PLAD (without the linker) ranging from a high of 100 μg/mL to a low of 0.032 μg/mL prior to the addition of IL-17A at 5 ng/ml. The recombinant IL-17 PLAD was made from either the first or second generation of human PLAD constructs described in Example 6 (IL-17R PLAD-GSS-FH and IL-17R PLAD-mod-GSS-FH, respectively), while the recombinant IL-17R PLAD-linker was made from the first generation of human PLAD constructs described in Example 6 (IL-17R PLAD-LINKER-GSS-FH). Assay controls included cells stimulated with 5 ng/mL human IL-17A (known to induce GROα secretion) in the presence or absence of anti-IL-17R M202 antibody. After 24 hours in culture (37° C., 10% $CO_2$), the assay plate was centrifuged at 1000 rpm for 5 minutes and the supernatants were collected for analysis. Supernatant concentrations of the chemokine GROα were measured by ELISA. The GROα ELISA limit of detection was 125 pg/mL.

The results of the study are shown in Table 2.

TABLE 2

| | | | pg/mL GROα |
|---|---|---|---|
| | | No Stim | 14.33 |
| 5 ng/mL huIL-17A | | | 518.64 |
| | M202 (ug/mL) | 100 | 17.79 |
| | | 20 | 18.49 |
| | | 4 | 23.67 |
| | | 0.8 | 38.47 |
| | | 0.16 | 90.72 |
| | | 0.032 | 258.14 |
| | IL-17R PLAD-mod-GSS-FH (ug/mL) | 100 | 410.73 |
| | | 20 | 440.24 |
| | | 4 | 499.06 |
| | | 0.8 | 483.62 |
| | | 0.16 | 485.81 |
| | | 0.032 | 466.96 |
| | IL-17R PLAD-GSS-FH (ug/mL) | 100 | 299.82 |
| | | 20 | 362.59 |
| | | 4 | 420.15 |
| | | 0.8 | 470.62 |
| | | 0.16 | 463.33 |

TABLE 2-continued

| | | pg/mL GROα |
|---|---|---|
| | 0.032 | 459.93 |
| IL-17R PLAD-LINKER-GSS-FH (ug/mL) | 100 | 315.29 |
| | 20 | 309.52 |
| | 4 | 380.71 |
| | 0.8 | 459.66 |
| | 0.16 | 541.33 |
| | 0.032 | 436.93 |

Example 8

This example demonstrates a method of assaying murine PLAD constructs in mouse cells.

ST-2 cells were seeded at 0.8 million cells/well in a 24-well plate and incubated overnight. During the next morning, cells were incubated with PLAD or PLAD/Linker (3, 10, or 30 μg/ml) for 1 hour. As a positive control, M750 & M751 (IL-17 receptor neutralization antibodies) were additionally incubated with cells for 1 hour. IL-17 (10 ng/ml) was added. Supernatants were collected after 24 hours of IL-17 stimulation. IL-6 concentrations were tested using ELISA. The results of the study are shown in Tables 3 and 4.

TABLE 3

| Sample | IL-6 Concentration (pg/ml) |
|---|---|
| Untreated | 235.38365 |
| IL-17A 10 ng/ml | 2424.5794 |
| IL-17A + M750 10 ug/ml | 252.98864 |
| IL-17A + M751 10 ug/ml | 395.93376 |
| IL-17A + muPLAD 30 ug/ml | 2037.9205 |
| IL-17A + muPLAD 10 ug/ml | 2533.1654 |
| IL-17A + muPLAD 3 ug/ml | 2238.4249 |
| IL-17A + muPLAD-L 30 ug/ml | 1884.4837 |
| IL-17A + muPLAD-L 10 ug/ml | 2785.8677 |
| IL-17A + muPLAD-L 3 ug/ml | 2705.0157 |

TABLE 4

| Sample | IL-6 Concentration (pg/ml) |
|---|---|
| IL-17° + TNFa 2 ng/ml | 7217.2337 |
| IL-17A + TNFa + M750 10 ug/ml | 7044.5517 |
| IL-17A + TNFa + M751 10 ug/ml | 7046.0464 |
| IL-17A + TNFa + muPLAD 30 ug/ml | 6976.5459 |
| IL-17A + TNFa + muPLAD 10 ug/ml | 6984.7658 |
| IL-17A + TNFa + muPLAD 3 ug/ml | 6984.0185 |
| IL-17A + TNFa + muPLAD-L 30 ug/ml | 7177.6075 |
| IL-17A + TNFa + muPLAD-L 10 ug/ml | 7044.5517 |
| IL-17A + TNFa + muPLAD-L 3 ug/ml | 7019.1416 |

Example 9

This example demonstrates a method of assaying murine PLAD constructs in mouse cells.

ST-2 cells were seeded at 0.8 million cells/well in a 24-well plate and incubated overnight. During the next morning, cells were incubated with PLAD or PLAD/Linker (3, 10, or 30 µg/ml) for 1 hour. As a positive control, M750 & M751 (IL-17 receptor neutralization antibodies) were additionally incubated with cells for 1 hour. IL-17 (10 ng/ml) was added. Supernatants were collected after 24 hours of IL-17 stimulation. IL-6 concentrations or Groα (KC) concentrations were tested using ELISA.

The results of the IL-6 ELISA are shown in Table 5, while the results of the Groα (KC) ELISA are shown in Table 6.

TABLE 5

| Sample | IL-6 Concentration (pg/ml) |
|---|---|
| Untreated | 34.594026 |
| IL-17A 10 ng/ml | 121.6792 |
| IL-17A + M750 10 ug/ml | 39.110934 |
| IL-17A + M751 10 ug/ml | 31.542154 |
| IL-17A + muPLAD 30 ug/ml | 107.67534 |
| IL-17A + muPLAD 10 ug/ml | 124.59747 |
| IL-17A + muPLAD 3 ug/ml | 155.25775 |
| IL-17A + muPLAD-L 30 ug/ml | 110.04523 |
| IL-17A + muPLAD-L 10 ug/ml | 110.15474 |
| IL-17A + muPLAD-L 3 ug/ml | 182.2215 |

TABLE 6

| Sample | KC Concentration (pg/ml) |
|---|---|
| Untreated | 2008.5805 |
| IL-17A 10 ng/ml | 6135.9218 |
| IL-17A + TNFa 2 ng/ml | 6808.9294 |
| IL-17A + M750 10 ug/ml | 2939.0385 |
| IL-17A + TNFa + M750 10 ug/ml | 6891.7374 |
| TNFa 2 ng/ml | 4347.1317 |
| IL-17A + muPLAD 30 ug/ml | 6099.5637 |
| IL-17A + muPLAD 10 ug/ml | 6128.6495 |
| IL-17A + muPLAD 3 ug/ml | 6194.1139 |
| IL-17A + TNFa + muPLAD 30 ug/ml | 6298.4326 |
| IL-17A + TNFa + muPLAD 10 ug/ml | 6456.2625 |
| IL-17A + TNFa + muPLAD 3 ug/ml | 6152.8921 |
| IL-17A + muPLAD-L 30 ug/ml | 6230.4958 |
| IL-17A + muPLAD-L 10 ug/ml | 5444.3264 |
| IL-17A + muPLAD-L 3 ug/ml | 5976.0148 |
| IL-17A + TNFa + muPLAD-L 30 ug/ml | 5499.8126 |
| IL-17A + TNFa + muPLAD-L 10 ug/ml | 5548.0808 |
| IL-17A + TNFa + muPLAD-L 3 ug/ml | 5746.165 |

Example 10

This example demonstrates a method of testing for inhibition of IL-17A- and IL-17-F-mediated signal transduction in which gene expression is assayed.

Several IL-17-responsive cell lines (ST2, MC3T3-E1, wild type MEF cells) are used to assess the ability of soluble 17RA-PLAD constructs to inhibit IL-17A- and IL-17F-mediated gene expression. Genes to be assessed include IL-6, 24p3, CXCL1, CXCL5, CCL2, CCL7, C/EBPβ and C/EBPδ (Shen et al., *J. Biol. Chem.* 281: 24138-24148 (2006); Shen et al., *J. Leukoc. Biol.* 77: 388-399 (2005)). Cells are incubated with IL-17A, IL-17F in combination with TNFα for various time points (between 2 and 24 h), and conditioned supernatants are collected, as well as whole cell lysates, for mRNA and protein purification. ELISA, Western blotting, and real-time RT-PCR are used to assess expression of the genes listed above. Biologic activity of human and mouse PLAD constructs in IL-17A- and IL-17F-induced chemokine production assay from fibroblasts also is assessed.

Example 11

This example demonstrates a method of testing for inhibition of IL-17A- and IL-17-F-mediated signal transduction in which NF-κB and C/EBP activation are assayed.

The ability of the 17RA-PLAD constructs to inhibit NF-κB and C/EBP activation and DNA binding is tested. Cells are incubated with the soluble PLAD constructs together with ligand for a time period ranging from 0.5 to 4 h. Nuclear extracts are prepared and analyzed by EMSA with specific oligonucleotide probes as described in Shen et al., *J. Biol. Chem.* 281: 24138-24148 (2006).

Example 12

This example demonstrates a method of testing for inhibition of IL-17RA homodimerization and IL-17RC homodimerization.

The ability of the soluble PLAD constructs to prevent IL-17 ligand-induced reduction in FRET in cells expressing IL-17RA/CFP and IL-17RA/YFP is evaluated. Cells expressing IL-17RA/CFP and IL-17RA/YFP are contacted with one of the human or mouse soluble PLAD constructs described herein. FRET studies are carried out as essentially described in Kramer et al., *J. Immunology* 179: 6379-6383 (2007).

Example 13

This example demonstrates a method of testing for inhibition of IL-17RA-mediating signaling in vivo.

The function of the soluble PLAD constructs described herein are tested in vivo using a mouse model of arthritis (e.g., collagen-induced arthritis (CIA) mouse model). CIA mice are made as essentially described in Lubberts et al., *J. Immunol.* 170: 2655-2662 (2003). Varying doses of recombinant 17RA-PLAD constructs are administered to the mice. Knee joints of mice are removed from the mice and analyzed for pathology. The 17RA-PLAD efficacy in reducing arthritis scores compared to those of Enbrel and anti-IL-17 mAbs is assessed.

Additionally, a mouse model of periodontal bone loss is used to test for in vivo activity of the PLAD constructs. Mice treated with the 17RA-PLAD proteins are assessed for the degree of bone loss following *P. gingivalis* infection as essentially described in Yu et al., *Blood*, 109: 3794-3802 (2007).

Soluble PLAD leading to increased bone loss would demonstrate inhibition of IL-17RA in vivo.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed:

1. An isolated polypeptide consisting of the amino acid sequence of SEQ ID NO[s]: 4, 8, or 12.

2. A chimeric protein comprising two or more of the polypeptide of claim 1 and a heterologous polypeptide.

3. The chimeric protein of claim 2, wherein the heterologous polypeptide comprises an Fc region of an immunoglobulin, or a fragment thereof.

4. The isolated polypeptide of claim 1, further comprising a water-soluble polymer, wherein the water-soluble polymer is polyethylene glycol.

5. A composition comprising the polypeptide of claim 1 and a pharmaceutically acceptable carrier.

6. An isolated polypeptide consisting of amino acids LWD at the N-terminus of the amino acid sequence of SEQ ID NO[s]: 4, 8, or 12.

7. An isolated polypeptide consisting of the amino acid sequence of SEQ ID NO: 4, 8, or 12 and (a) a secretion signal peptide at the N-terminus of the polypeptide; or (b) an expression tag, a purification tag, or a combination thereof.

8. The isolated peptide of claim 7, wherein (a) said secretion signal peptide comprises the amino acid sequence of SEQ ID NO: 16 or 17; (b) said expression tag comprises the amino acid sequence of SEQ ID NO: 19; or (c) said purification tag comprises the amino acid sequence of SEQ ID NO: 20.

* * * * *

UNITED STATES PATENT AND TRADEMARK OFFICE
CERTIFICATE OF CORRECTION

| | | |
|---|---|---|
| PATENT NO. | : 8,460,647 B2 | Page 1 of 1 |
| APPLICATION NO. | : 12/595585 | |
| DATED | : June 11, 2013 | |
| INVENTOR(S) | : Gaffen et al. | |

It is certified that error appears in the above-identified patent and that said Letters Patent is hereby corrected as shown below:

On the Title Page "( * ) Notice:" should read:

( * ) Notice:  Subject to any disclaimer, the term of this patent is extended or adjusted under 35 U.S.C. 154(b) by 202 days.

~~This patent is subject to a terminal disclaimer.~~

Signed and Sealed this
Twenty-third Day of September, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,460,647 B2  Page 1 of 1
APPLICATION NO. : 12/595585
DATED : June 11, 2013
INVENTOR(S) : Gaffen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 695 days.

Signed and Sealed this
Eighth Day of September, 2015

Michelle K. Lee
*Director of the United States Patent and Trademark Office*